(12) United States Patent
Dao et al.

(10) Patent No.: US 11,427,549 B2
(45) Date of Patent: Aug. 30, 2022

(54) PYRIMIDINYLOXY BENZO-FUSED COMPOUNDS AS HERBICIDES

(71) Applicant: FMC Corporation, Philadelphia, PA (US)

(72) Inventors: Rachel Tran Dao, Newark, DE (US); Andrew Jon Deangelis, Wilmington, DE (US); John Robbins Debergh, Middletown, DE (US); Eric Allen Marshall, Rising Sun, MD (US)

(73) Assignee: FMC Corporation, Philadelphia, PA (US)

(*) Notice: Subject to any disclaimer, the term of this patent is extended or adjusted under 35 U.S.C. 154(b) by 208 days.

(21) Appl. No.: 16/609,975

(22) PCT Filed: Apr. 27, 2018

(86) PCT No.: PCT/US2018/029689
§ 371 (c)(1),
(2) Date: Oct. 31, 2019

(87) PCT Pub. No.: WO2018/204164
PCT Pub. Date: Nov. 8, 2018

(65) Prior Publication Data
US 2020/0055826 A1   Feb. 20, 2020

Related U.S. Application Data

(60) Provisional application No. 62/500,088, filed on May 2, 2017.

(51) Int. Cl.
| | |
|---|---|
| *A01N 43/54* | (2006.01) |
| *C07D 239/34* | (2006.01) |
| *C07D 403/12* | (2006.01) |
| *C07D 405/12* | (2006.01) |
| *C07D 411/12* | (2006.01) |

(52) U.S. Cl.
CPC .......... *C07D 239/34* (2013.01); *A01N 43/54* (2013.01); *C07D 403/12* (2013.01); *C07D 405/12* (2013.01); *C07D 411/12* (2013.01)

(58) Field of Classification Search
None
See application file for complete search history.

(56) References Cited

U.S. PATENT DOCUMENTS

| | | | |
|---|---|---|---|
| 4,248,619 A | 2/1981 | Serban et al. | |
| 4,371,736 A | 2/1983 | Selby | |
| 4,423,047 A | 12/1983 | Benneche et al. | |
| 4,427,437 A | 1/1984 | Serban et al. | |
| 4,460,588 A | 7/1984 | Serban et al. | |
| 4,863,924 A | 9/1989 | Haga et al. | |
| 5,332,717 A * | 7/1994 | Luthy | A01N 43/66 504/242 |
| 5,962,685 A | 10/1999 | Ueda et al. | |
| 6,268,310 B1 | 7/2001 | Ueda et al. | |
| 7,642,264 B2 | 1/2010 | McArthur et al. | |
| 8,431,607 B2 | 4/2013 | Liu et al. | |
| 9,133,175 B2 | 9/2015 | Alvaro et al. | |
| 9,567,318 B2 | 2/2017 | Chiosis et al. | |
| 9,695,155 B2 | 7/2017 | Sharpe et al. | |
| 9,963,442 B2 | 5/2018 | Satterfield | |
| 10,131,652 B2 | 11/2018 | Deprez | |
| 10,654,840 B2 | 5/2020 | Deprez | |
| 2009/0221547 A1 | 9/2009 | Gao et al. | |
| 2010/0022538 A1 | 1/2010 | Boebel et al. | |

(Continued)

FOREIGN PATENT DOCUMENTS

| | | |
|---|---|---|
| AU | 3916678 | 1/1981 |
| AU | 535637 | 3/1984 |

(Continued)

OTHER PUBLICATIONS

The Agrochemical Handbook, 3rd Edition, Royal Society Of Chemistry,A0835/Aug 91 on Acetochlor (Year: 1991).*
European Patent Office: Notice of Opposition to European Patent, EP3094631 Electronically Available at the European Patent Register Oct. 9, 2019.
Nezu, "Dimethoxypyrimidines as Novel Herbicides, Part 1" Synthesis and Herbicidal Activity of Dimethoxyphenoxyphenoxypyrimidines and Analogues, Pestic. Sci., Jun. 1, 1996, 47, 103-113.

(Continued)

*Primary Examiner* — Alton N Pryor
(74) *Attorney, Agent, or Firm* — Xiaobin Ding; FMC Corporation

(57) ABSTRACT

Disclosed are compounds of Formula (1), including all stereoisomers, N-oxides, and salts thereof (Formula (1)) wherein K, Z, $R^2$, $R^3$ and m are as defined in the disclosure. Also disclosed are compositions containing the compounds, N-oxides and salts, processes for making such compounds, N-oxides, salts and compositions, and methods for controlling undesired vegetation comprising contacting the undesired vegetation or its environment with an effective amount of a compound, N-oxide, salt or composition.

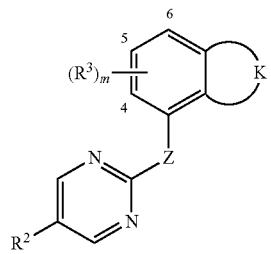

14 Claims, No Drawings

(56) References Cited

U.S. PATENT DOCUMENTS

| | | |
|---|---|---|
| 2017/0190671 A1 | 7/2017 | Reddy et al. |
| 2018/0206497 A1 | 7/2018 | Stevenson et al. |

FOREIGN PATENT DOCUMENTS

| | | |
|---|---|---|
| AU | 535637 B2 | 3/1984 |
| CA | 2290379 | 11/1998 |
| DE | 4438824 | 4/1995 |
| EP | 0008192 | 2/1980 |
| EP | 0410590 | 1/1991 |
| EP | 0665224 | 8/1995 |
| GB | 2237570 | 5/1991 |
| JP | S61236766 | 10/1986 |
| JP | H4108777 | 4/1992 |
| JP | 10251255 | 9/1998 |
| JP | 2012012299 | 1/2012 |
| JP | 5753178 | 7/2015 |
| WO | 8400685 | 3/1984 |
| WO | 940017059 | 8/1994 |
| WO | 19960033994 | 10/1996 |
| WO | 9840379 | 9/1998 |
| WO | 2007095602 | 8/2007 |
| WO | 2008009963 | 1/2008 |
| WO | 2009/029518 | 3/2009 |
| WO | 2011/069951 | 6/2011 |
| WO | 2012076877 | 6/2012 |
| WO | WO2012076877 A1 | 6/2012 |
| WO | 2016/196606 | 12/2016 |
| WO | 20170011288 | 1/2017 |
| WO | WO2017011288 A1 | 1/2017 |

OTHER PUBLICATIONS

Saito, Yoshihiro et al. "Preparation of pyrimidine derivatives as herbicides". XP002735697, retrieved from STN Database accession No. 1992:545339 abstract, CAS-RN 143437-16-5.

Selby et al., "N-Azolyl Phenoxypyrimidine Herbicides: Novel Inhibitors of Carotenoid Biosynthesis Part I"; Synthesis and Chemistry of Agrochemicals VI, ACS Symposium Series 800, Jan. 1, 2002 (Jan. 1, 2002), pp. 74-84, XP001120637, ISBN: 0-8412-3783-2.

Tamaru, "Studies of the New Herbicide KIH-6127. Part II. Synthesis and Herbicidal Activity of 6-Acyl Pyrimidin-2-yl Salicylates and Analogues Against Barnyard Grass", Pestic. Sci., Aug. 1, 1996, 47, 327-335.

International Search Report for corresponding PCT/US2018/029689 dated Jun. 22, 2018.

International Search Report of the International Searching Authority for PCT/US2018/029689 dated Jun. 22, 2018.

* cited by examiner

PYRIMIDINYLOXY BENZO-FUSED COMPOUNDS AS HERBICIDES

FIELD OF THE INVENTION

This disclosure relates to certain pyrimidinyloxy benzo-fused compounds, N-oxides thereof, and salts of the compounds and N-oxides; compositions comprising such compounds, N-oxides and salts; processes for making such compounds, N-oxides, salts and compositions; and methods for using such compounds, N-oxides, salts and compositions to control undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This disclosure relates, in part, to compounds of Formula 1 (including all geometric and stereoisomers), N-oxides of such compounds, and salts of such compounds and N-oxides:

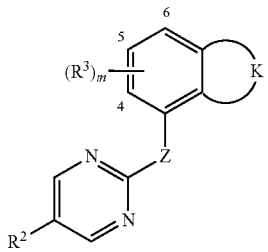

1 wherein
K together with the two contiguous linking carbon atoms forms a 4-, 5- or 6-membered ring selected from the group consisting of K-1, K-2, K-3, K-4, K-5, K-6, K-7, K-8, K-9, K-10, K-11, K-12, K-13, K-14, K-15, K-16 and K-17:

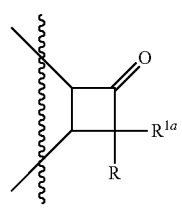

K-1

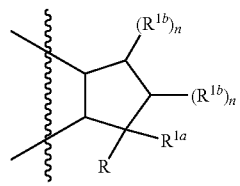

K-2

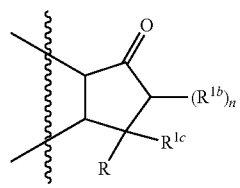

K-3

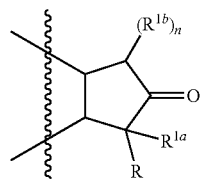

K-4

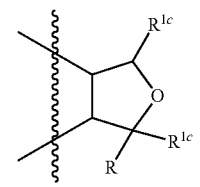

K-5

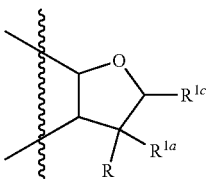

K-6

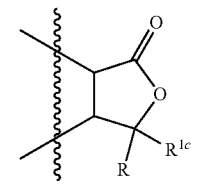

K-7

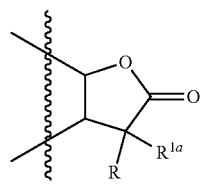

K-8

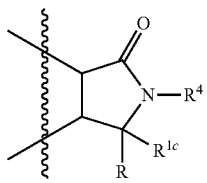

K-9

K-10 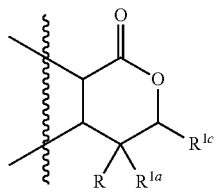

K-11 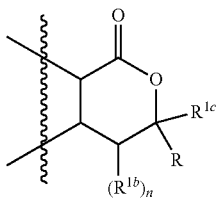

K-12 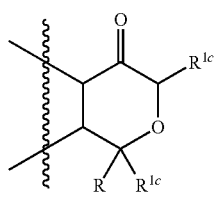

K-13 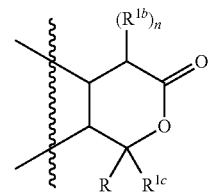

K-14 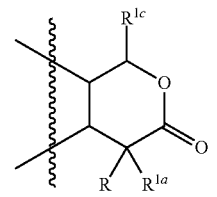

K-15 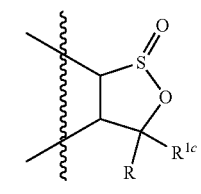

K-16 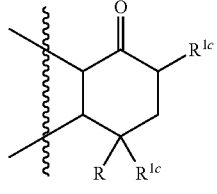

K-17 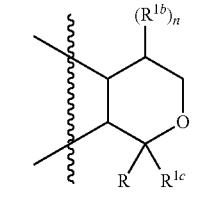

R is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl, $C_2$-$C_6$ haloalkylthioalkyl, benzyl, —N($R^5$)(O$R^6$), —ON($R^{7a}$)($R^{7b}$) or —N($R^5$)N($R^{7a}$)($R^{7b}$);

each $R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano or $S(O)_pR^8$;

each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_pR^8$;

each $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_pR^8$;

$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_qR^9$;

each $R^3$ is independently halogen, cyano, nitro, CHO, C(=O)NH$_2$, C(=S)NH$_2$, SO$_2$NH$_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_4$ alkoxy, $C_3$-$C_4$ alkenyloxy, $C_3$-$C_4$ alkynyloxy, $C_1$-$C_4$ haloalkoxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy or $C_2$-$C_4$ alkylthioalkyl;

m is 0, 1, 2 or 3;
each n is independently selected from 0 and 1;
p is 0, 1 or 2;
q is 0, 1 or 2;
r is 0, 1 or 2;
Z is O or S;
$R^4$ is nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_rR^9$;
$R^5$ is $C_1$-$C_6$ alkyl or $C_1$-$C_6$ haloalkyl;
$R^6$ is H, $C_1$-$C_6$ alkyl, $C_1$-$C_6$ haloalkyl, $C_2$-$C_6$ alkoxyalkyl, $C_2$-$C_6$ haloalkoxyalkyl or $C_2$-$C_6$ cyanoalkyl;
each $R^{7a}$ and $R^{7b}$ is independently H, $C_1$-$C_6$ alkyl or $C_1$-$C_6$ haloalkyl;
$R^8$ is $C_1$-$C_6$ alkyl or $C_1$-$C_6$ haloalkyl; and
$R^9$ is independently $C_1$-$C_6$ alkyl, $C_1$-$C_6$ haloalkyl, $C_1$-$C_6$ alkylamino or $C_2$-$C_{10}$ dialkylamino.

This disclosure also relates, in part, to an agricultural composition (generally herbicidal) comprising such a compound, N-oxide or salt in a herbicidally effective amount and at least one component selected from the group consisting of surfactants, solid diluents and liquid diluents, the composition optionally further comprising at least one additional active ingredient selected from the group consisting of other herbicides and herbicide safeners.

This disclosure also relates, in part, to an herbicidal mixture comprising (a) a compound selected from Formula 1, N-oxides, and salts thereof, and (b) at least one additional active ingredient selected from (b1) through (b16); and salts of compounds of (b1) through (b16), as described below.

This disclosure also relates, in part, to processes for making the above-identified compounds, N-oxides, salts and compositions.

This disclosure also relates, in part, to methods for controlling the growth of undesired vegetation comprising contacting the vegetation or its environment with a herbicidally effective amount of an above-identified compound, N-oxide, salt or composition.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed disclosure. The term "consisting essentially of" occupies a middle ground between "comprising" and "consisting of".

Where applicants have defined a disclosure or a portion thereof with an open-ended term such as "comprising," it should be readily understood that (unless otherwise stated) the description should be interpreted to also describe such a disclosure using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HCCCH_2O$, $CH_3CCCH_2O$ and $CH_3CCCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", "alkenylthio", and the like, are defined analogously to the above examples. "Cyanoalkoxyalkyl" denotes an alkoxyalkyl group substituted with one cyano group.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" (or "halocycloalkylalkyl") denotes cycloalkyl substitution (or halocycloalkyl substitution) on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" (or "halocycloalkylalkoxy") denotes cycloalkyl (or halocycloalkyl, e.g. cycloalkyl substituted with halogen) linked through an oxygen atom to an alkyl chain. Examples of "cycloalkylalkoxy" include cyclopropylmethoxy, cyclopentylethoxy, and other cycloalkyl (or halocycloalkyl) moieties bonded to straight-chain or branched alkoxy groups. The term "cycloamino" denotes a cyclic amine moiety bonded through nitrogen. Examples of "cycloamino" include —N[CH$_2$CH$_2$CH$_2$—] (i.e. azetidine) and —N[CH$_2$CH$_2$CH$_2$CH$_2$—], (i.e. pyrrolidine). The term "cycloalkylthio" denotes cycloalkyl substitution bonded through a sulfer atom. Examples of "cycloalkylthio" include c-Pr(S)— and cyclopentyl(S)—. The term "cycloalkylsulfonyl" denotes cycloalkyl substitution bonded through a sulfonyl moiety. Examples of "cycloalkylsulfonyl" include c-Pr(S=O$_2$)— and cyclopentyl(S=O$_2$)—. The term "cycloalkylcarbonyl" denotes cycloalkyl substitution bonded through a carbonyl moiety. Examples of "cycloalkylcarbonyl" include c-Pr(C=O)— and cyclopentylC(=O)—.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "halocycloalkyl", "haloalkoxy", "haloalkylthio", "haloalkenyl", "haloalkynyl", and the like, are defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CHCH$_2$— and CF$_3$CH$_2$CH=CHCH$_2$—. Examples of "haloalkynyl" include HC≡CCHCl—, CF$_3$C≡C—, CCl$_3$C≡C— and FCH$_2$C≡CCH$_2$—. Examples of "alkoxyhaloalkyl" include CH$_3$OCF$_2$CH$_2$—, CH$_3$CH$_2$OCH$_2$CCl$_2$— and CF$_3$CH$_2$CH$_2$OCH$_2$— as well as branched alkyl derivatives.

The term "haloalkenyloxy" refers to a haloalkenyl group bonded through oxygen. Examples of "haloalkenyloxy" include (Cl)$_2$C=CHCH$_2$O— and CF$_3$CH$_2$CH=CHCH$_2$O—. The term "haloalkylamino" refers to a haloalkyl group bonded through a nitrogen atom (i.e. as a secondary amine). Examples of "haloalkylamino" include CF$_3$NH—, CCl$_3$CH$_2$NH—, HCF$_2$CH$_2$CH$_2$NH— and CF$_3$CH$_2$NH—. The term "haloalkylcarbonyl" refers to a haloalkyl group bonded through a carbonyl moiety. Examples of "haloalkylcarbonyl" include CH$_2$ClC(=O)—, CH$_3$CHClCH$_2$C(=O)— and (CH$_3$)$_2$CCl(=O)—. The term "haloalkylthioalkyl" refers to a haloalkylthio group bonded through an alkyl moiety. Examples of "haloalkylthioalkyl" include CCl$_3$SCH$_2$—, CF$_3$SCH$_2$—, CCl$_3$CH$_2$SCH$_2$— and ClCH$_2$CH$_2$CH$_2$SCH$_2$—. The term "haloalkynyloxy" refers to a haloalkynyl group bonded through an oxygen atom. Examples of "haloalkynyloxy" include HC≡CCHClO—, CF$_3$C≡CO—, CCl$_3$C≡CO— and FCH$_2$C≡CCH$_2$O—. The term "haloalkoxyalkyl" refers to a haloalkoxy group bonded through an alkyl moiety. Examples of "haloalkoxyalkyl" include CF3OCH$_2$—, ClCH$_2$CH$_2$OCH$_2$CH$_2$—, Cl$_3$CCHOCH$_2$— as well as branched alkyl derivatives. The term "halocycloalkylalkoxy" refers to a halocycloalkyl group bonded through an oxygen atom to an alkyl group. Examples of "halocycloalkylalkoxy" include c-Pr(2-Cl)CH$_2$O— and c-Bu(1-Cl)CH$_2$CH$_2$O—. The term "halodialkylamino" indicates two haloalkyl groups bonded through nitrogen. Examples of "halodialkylamino" include (CH$_2$Cl)$_2$N, (CH$_2$CH$_2$Cl)$_2$N— and (CH$_2$CH$_2$Cl)(CH$_2$Br)N—.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers.

"Alkylcarbonyloxy" denotes an alkylcarbonyl moiety linked through an oxygen atom attached to the carbonyl. Examples of "alkylcarbonyloxy" include CH$_3$C(=O)O—, CH$_3$CH$_2$CH$_2$C(=O)O— and (CH$_3$)$_2$CHC(=O)O—.

"Cyanoalkoxy" denotes an alkoxy group substituted with one cyano group. Examples of "cyanoalkoxy" include NCCH$_2$O—, NCCH$_2$CH$_2$O— and CH$_3$CH(CN)CH$_2$O—.

The term "hydroxyalkyl" denotes an alkyl group substituted with one hydroxyl group. Examples of "hydroxyalkyl" include HOCH$_2$—, HOCH$_2$CH$_2$— and CH$_3$CH(OH)CH$_2$—.

The term "nitroalkyl" denotes an alkyl group substituted with one nitro group. Examples of "nitroalkyl" include O$_2$NCH$_2$—, O$_2$NCH$_2$CH$_2$— and CH$_3$CH(NO$_2$)CH$_2$—.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., $(R^3)_m$, where m is 0, 1, 2 or 3. Further, when the subscript indicates a range, e.g. $(R)_{i-j}$, then the number of substituents may be selected from the integers between i and j inclusive. When a group contains a substituent which can be hydrogen (H), for example $R^{1a}$ and $R^6$, then when this substituent is taken as hydrogen, it is recognized that this is equivalent to said group being unsubstituted. When a variable group is shown to be optionally attached to a position, for example $(R^{1b})_n$ and $(R^6)_m$ wherein n and m may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1, (e.g. K) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically, a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above K together with the two contiguous linking carbon atoms forms a 4-, 5- or 6-membered ring selected from the rings in Exhibit 1. Each K ring is substituted with R and optionally substituted with $R^{1a}$ or $R^{1c}$ on the same carbon atom. Each K ring is optionally substituted with $(R^{1b})_n$ or $R^{1c}$ on any other carbon atom of the K ring and optionally substituted with $R^4$ on any nitrogen atom of the K ring. The term "optionally substituted" in connection with the $R^{1a}$, $R^{1b}$, $R^{1c}$ and $R^4$ substituents on these K rings refers to K rings that are unsubstituted with $R^{1a}$, $R^{1b}$, $R^{1c}$ or $R^4$ or have a non-hydrogen $R^{1a}$, $R^{1b}$, $R^{1c}$ and/or $R^4$ substituent. An example of a K ring wherein the K ring is optionally substituted with at least one $(R^{1b})_n$ substituent include the ring systems K-2 to K-4, K-11 and K-13 in Exhibit 1, wherein each n is independent selected from 0 and 1. In ring K-2, two $(R^{1b})_n$ substitutents are shown. Both $R^{1b}$ substituents, if present (i.e. n=1), are independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_p R^8$. As with the carbon atoms in the ring, nitrogen atoms that require substitution to fill their valence are substituted with hydrogen or with $R^4$, e.g. K-9. Although $R^{1a}$ $(R^{1b})_n$ and/or $R^{1c}$ are shown in the structures K-1 to K-15, it is noted that none of them need to be present since they are optional substituents. In the exemplified K rings, the upper left bond is attached through the available linking carbon atom of the phenyl group portion of Formula 1 and the lower left bond is attached through the available linking carbon atom to the Z atom of the phenyl group portion of Formula 1. The wavy line indicates that the K ring is attached to the remainder of Formula 1 as illustrated below.

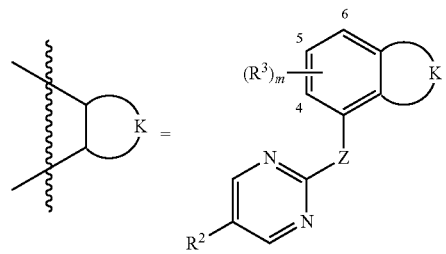

Exhibit 1

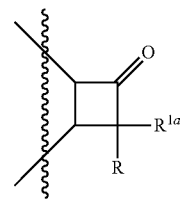

K-1

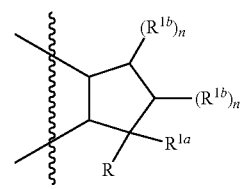

K-2

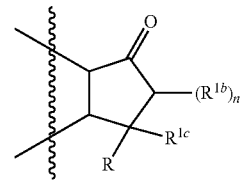

K-3

-continued

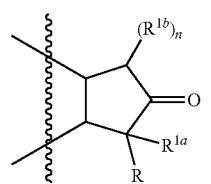
K-4

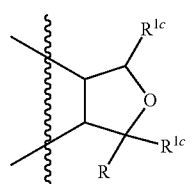
K-5

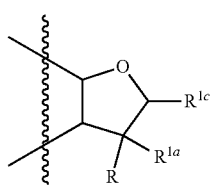
K-6

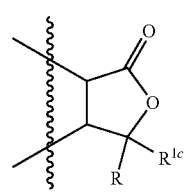
K-7

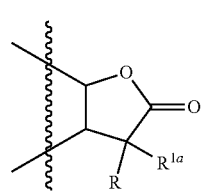
K-8

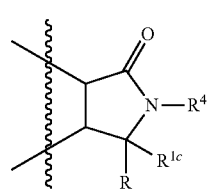
K-9

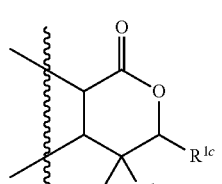
K-10

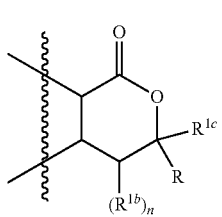
K-11

-continued

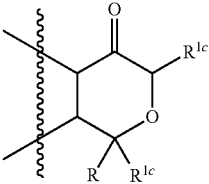
K-12

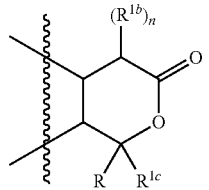
K-13

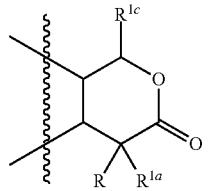
K-14

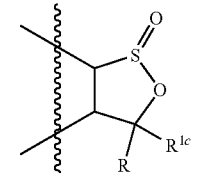
K-15

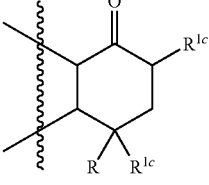
K-16

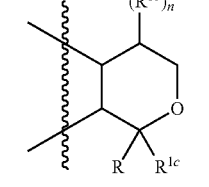
K-17

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this disclosure can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the disclosure may be present as a mixture of stereoisomers, individual stereoisomers or as an optically active form. For a comprehensive discussion of all aspects of stereoisomerism, see Ernest L. Eliel and Samuel H.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present disclosure comprises compounds selected from Formula 1, N-oxides and agriculturally suitable salts thereof.

Embodiments of the present disclosure as described in the Summary of the Invention include (where Formula 1 as used in the following Embodiments includes N-oxides and salts thereof):

Embodiment 1

A compound of Formula 1 including all geometric and stereoisomers, N-oxides, and salts thereof, agricultural compositions containing them and their use as herbicides.

Embodiment 2

A compound of Embodiment 1 wherein K is K-2, K-3, K-4, K-5, K-6, K-7, K-8, K-10, K-11, K-12, K-13, K-14 or K-15.

Embodiment 2a

A compound of Embodiment 2 wherein K is K-2, K-3, K-4, K-5, K-6, K-7, K-8 or K-10.

Embodiment 3

A compound of Embodiment 2a wherein K is K-2, K-3, K-4, K-5, K-6, K-7 or K-8.

Embodiment 4

A compound of Embodiment 3 wherein K is K-3, K-5 or K-7.

Embodiment 5

A compound of Formula 1 or any one of Embodiments 1 through 4 either alone or in combination, wherein R is $C_1$-$C_6$ alkyl or $C_1$-$C_6$ haloalkyl.

Embodiment 6

A compound of Embodiment 5 wherein R is $C_2$-$C_5$ alkyl or $C_2$-$C_5$ haloalkyl.

Embodiment 7

A compound of Embodiment 6 wherein R is $C_3$-$C_4$ alkyl or $C_3$-$C_4$ haloalkyl.

Embodiment 8

A compound of Embodiment 7 wherein R is $C_3$-$C_4$ haloalkyl.

Embodiment 9

A compound of Embodiment 8 wherein R is —$CH_2CH_2CF_3$.

Embodiment 10

A compound of Formula 1 or any one of Embodiments 1 through 9 either alone or in combination, wherein $R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy or cyano.

Embodiment 11

A compound of Embodiment 10, wherein $R^{1a}$ is selected from hydrogen, halogen, $C_1$-$C_2$ alkyl, $C_1$-$C_2$ haloalkyl, hydroxy or cyano.

Embodiment 12

A compound of Embodiment 11 wherein $R^{1a}$ is H, F, OH, $CF_3$ or CN.

Embodiment 13

A compound of Embodiment 12 wherein $R^{1a}$ is H or OH.

Embodiment 14

A compound of Embodiment 13 wherein $R^{1a}$ is H.

Embodiment 15

A compound of Formula 1 or any one of Embodiments 1 through 14 either alone or in combination, wherein n is 0.

Embodiment 16

A compound of Formula 1 or any one of Embodiments 1 through 14 either alone or in combination, wherein n is 1.

Embodiment 17

A compound of Formula 1 or any one of Embodiments 1 through 14 and 16 either alone or in combination, wherein each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano.

Embodiment 18

A compound of Embodiment 17, wherein each $R^{1b}$ is independently selected from halogen, $C_1$-$C_2$ alkyl, $C_1$-$C_2$ haloalkyl, hydroxy and cyano.

Embodiment 19

A compound of Embodiment 18 wherein each $R^{1b}$ is independently selected from halogen, hydroxy, $C_1$-haloalkyl and cyano.

Embodiment 20

A compound of Embodiment 19 wherein each $R^{1b}$ is independently selected from F, OH, $CF_3$ and CN.

Embodiment 21

A compound of Formula 1 or any one of Embodiments 1 through 20 either alone or in combination, wherein $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano.

Embodiment 22

A compound of Embodiment 21 wherein $R^{1c}$ is independently selected from hydrogen, F, $C_1$-$C_2$ alkyl, $C_1$-$C_2$ haloalkyl, hydroxy and cyano.

Embodiment 23

A compound of Embodiment 22 wherein each $R^{1c}$ is independently selected from H, F, OH, $CF_3$ and CN.

Embodiment 24

A compound of Embodiment 23 wherein each $R^{1c}$ is independently selected from H and OH.

Embodiment 25

A compound of Embodiment 24 wherein each $R^{1c}$ is H.

Embodiment 26

A compound of Formula 1 or any one of Embodiments 1 through 25 either alone or in combination, wherein $R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl or $C_3$-$C_6$ cycloalkyl.

Embodiment 27

A compound of Embodiment 26 wherein $R^2$ is halogen, cyano, $C_1$-$C_2$ alkyl or $C_1$-$C_2$ haloalkyl.

Embodiment 28

A compound of Embodiment 27 wherein $R^2$ is halogen, $CH_3$ or $CF_3$.

Embodiment 29

A compound of Embodiment 28 wherein $R^2$ is halogen.

Embodiment 30

A compound of Embodiment 29 wherein $R^2$ is F, Cl, Br or I.

Embodiment 31

A compound of Embodiment 30 wherein $R^2$ is Cl.

Embodiment 32

A compound of Formula 1 or any one of Embodiments 1 through 31 either alone or in combination wherein $R^3$ is independently halogen, cyano, nitro, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_4$ alkoxy, $C_3$-$C_4$ alkenyloxy, $C_3$-$C_4$ alkynyloxy, $C_1$-$C_4$ haloalkoxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy or $C_2$-$C_4$ alkylthioalkyl.

Embodiment 33

A compound of Formula 1 or any one of Embodiments 1 through 32 either alone or in combination, wherein m is 0 or 1.

Embodiment 34

A compound of Embodiment 33 wherein m is 1.

Embodiment 35

A compound of Embodiment 34 wherein $R^3$ is at the 5- or 6-position.

Embodiment 36

A compound of Embodiment 35 wherein $R^3$ is at the 6-position.

Embodiment 37

A compound of any one of Embodiments 32 through 36 either alone or in combination wherein $R^3$ is halogen, cyano, $C_1$-$C_4$ alkyl or $C_1$-$C_4$ haloalkyl.

Embodiment 38

A compound of Embodiment 37 wherein $R^3$ is halogen or cyano.

Embodiment 38A

A compound of Embodiments 34 and 38 wherein $R^3$ is at the 5- or 6-position and is selected from halogen or cyano.

Embodiment 39

A compound of Embodiment 38 wherein $R^3$ is Br, F or cyano.

Embodiment 40

A compound of Formula 1 or any one of Embodiments 1 through 39 either alone or in combination, wherein Z is O.

Embodiments of this disclosure, including Embodiments 1-40 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this disclosure, including Embodiments 1-40 above as well as any other embodiments described herein, and any combination thereof, pertain to the compositions and methods of the present disclosure.

Combinations of Embodiments 1-40 are illustrated by:

Embodiment A

A compound of Formula 1 wherein
K is K-2, K-3, K-4, K-5, K-6, K-7, K-10, K-11, K-12, K-13, K-14 or K-15;
Z is O;
R is $C_1$-$C_6$ alkyl or $C_1$-$C_6$ haloalkyl;
$R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy or cyano;
each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano;
each $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano;
$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl or $C_3$-$C_6$ cycloalkyl;
$R^3$ is halogen, cyano, $C_1$-$C_4$ alkyl or $C_1$-$C_4$ haloalkyl; and
m is 0 or 1.

Embodiment B

A compound of Embodiment A wherein
K is K-2, K-3, K-4, K-5, K-6, K-7, K-8 or K-10;
R is $C_3$-$C_4$ alkyl or $C_3$-$C_4$ haloalkyl;
$R^{1a}$ is hydrogen, halogen, $C_1$-$C_2$ alkyl, $C_1$-$C_2$ haloalkyl, hydroxy or cyano;
each $R^{1b}$ is independently selected from halogen, $C_1$-$C_2$ alkyl, $C_1$-$C_2$ haloalkyl, hydroxy and cyano;
each $R^{1c}$ is independently selected from hydrogen, F, $C_1$-$C_2$ alkyl, $C_1$-$C_2$ haloalkyl, hydroxy and cyano;
$R^2$ is halogen, cyano, $C_1$-$C_2$ alkyl or $C_1$-$C_2$ haloalkyl; and
$R^3$ is at the 5- or 6-position and selected from halogen or cyano.

Embodiment B1

A compound of Embodiment B wherein
K is K-2, K-3, K-4, K-5, K-6, K-7 or K-8;
R is $C_3$-$C_4$ alkyl or $C_3$-$C_4$ haloalkyl;
$R^{1a}$ is hydrogen, halogen, $C_1$-$C_2$ alkyl, $C_1$-$C_2$ haloalkyl, hydroxy or cyano;
each $R^{1b}$ is independently selected from halogen, $C_1$-$C_2$ alkyl, $C_1$-$C_2$ haloalkyl, hydroxy and cyano;
each $R^{1c}$ is independently selected from hydrogen, F, $C_1$-$C_2$ alkyl, $C_1$-$C_2$ haloalkyl, hydroxy and cyano;
$R^2$ is halogen, cyano, $C_1$-$C_2$ alkyl or $C_1$-$C_2$ haloalkyl; and
$R^3$ is at the 5- or 6-position and selected from halogen or cyano.

Embodiment C

A compound of Embodiment B1 wherein
K is K-3, K-5 or K-7;
R is $C_3$-$C_4$ haloalkyl;
$R^{1a}$ is H, F, OH, $CF_3$ or CN;
$R^{1b}$ is independently selected from F, OH, $CF_3$ and CN;
$R^{1c}$ is independently selected from H, F, OH, $CF_3$ and CN;
$R^2$ is halogen; and
$R^3$ is F or cyano.

Embodiment D

A compound of Embodiment C wherein
R is —CH$_2$CH$_2$CF$_3$ or —CH$_2$CH$_2$CH$_2$CF$_3$;
R$^{1a}$ is hydrogen;
each R$^{1c}$ is hydrogen;
R$^2$ is Cl; and
each n is 0.

Specific embodiments include compounds of Formula 1 selected from the group consisting of:
4-[(5-Chloro-2-pyrimidinyl)oxy]-3-(4,4,4-trifluorobutyl)-1 (3H)-isobenzofuranone;
(3S)-4-[(5-Chloro-2-pyrimidinyl)oxy]-3-(4,4,4-trifluorobutyl)-1-(3H)-isobenzofuranone;
(3R)-4-[(5-Chloro-2-pyrimidinyl)oxy]-3-(4,4,4-trifluorobutyl)-1-(3H)-isobenzofuranone;
4-[(5-Chloro-2-pyrimidinyl)oxy]-3-(3,3,3-trifluoropropyl)-1(3H)-isobenzofuranone;
8-[(5-Chloro-2-pyrimidinyl)oxy]-1-(4,4,4-trifluorobutyl)-1H-2-benzopyran-4(3H)-one;
4-[(5-Chloro-2-pyrimidinyl)oxy]-2,3-dihydro-3-(4,4,4-trifluorobutyl)-1H-inden-1-one;
5-Chloro-2-[[1,3-dihydro-3-(4,4,4-trifluorobutyl)-4-isobenzofuranyl]oxy]pyrimidine;
5-Chloro-2-[[1,3-dihydro-3-(3,3,3-trifluoropropyl)-4-isobenzofuranyl]oxy]pyrimidine;
5-Chloro-2-[[2,3-dihydro-3-(4,4,4-trifluorobutyl)-1H-inden-4-yl]oxy]pyrimidine;
4-[(5-Chloro-2-pyrimidinyl)oxy]-2,3-dihydro-3-(4,4,4-trifluorobutyl)-1H-inden-1-ol;
4-[(5-Chloro-2-pyrimidinyl)oxy]-2,3-dihydro-3-(3,3,3-trifluoropropyl)-1H-inden-1-one;
4-[(5-Chloro-2-pyrimidinyl)oxy]-2,3-dihydro-2-methyl-3-(4,4,4-trifluorobutyl)-1H-isoindol-1-one;
4-[(5-Chloro-2-pyrimidinyl)oxy]-2,3-dihydro-3-(4,4,4-trifluorobutyl)-1H-isoindol-1-one;
7-[(5-Chloro-2-pyrimidinyl)oxy]-2,3-dihydro-1-(3,3,3-trifluoropropyl)-1H-inden-1-ol; and
5-Chloro-2-[[1-oxido-3-(4,4,4-trifluorobutyl)-3H-2,1-benzoxathiol-4-yl]oxy]pyrimidine.

Specific embodiments also include compounds of Formula 1 selected from the group consisting of:
5-[(5-Chloro-2-pyrimidinyl)oxy]-3,4-dihydro-4-(4,4,4,-trifluorobutyl)-1H-2benzopyran-1-one;
8-[(5-Chloro-2-pyrimidinyl)oxy]-1,4-dihydro-1-(4,4,4-trifluorobutyl)-3H-2-benzopyran-3-one;
(3S)-4-[(5-Chloro-2-pyrimidinyl)oxy]-3-(3,3,3-trifluoropropyl)-1(3H)-isobenzofuranone;
(3R)-4-[(5-Chloro-2-pyrimidinyl)oxy]-3-(3,3,3-trifluoropropyl)-1(3H)-isobenzofuranone;
5-Chloro-2-[[(3R)-1,3-dihydro-3-(3,3,3-trifluoropropyl)-4-isobenzofuranyl]oxy]-pyrimidine;
5-Chloro-2-[[(3S)-1,3-dihydro-3-(3,3,3-trifluoropropyl)-4-isobenzofuranyl]oxy]-pyrimidine;
2-[(5-Chloro-2-pyrimidinyl)oxy]-8-(4,4,4-trifluorobutyl)bicyclo[4.2.0]octa-1,3,5-trien-7-one;
5-[(5-Chloro-2-pyrimidinyl)oxy]-3,4-dihydro-3-(3,3,3-trifluoropropyl)-1H-2-benzopyran-1-one;
2-[(5-Chloro-2-pyrimidinyl)oxy]-8-(3,3,3-trifluoropropyl)bicyclo[4.2.0]octa-1,3,5-trien-7-one;
5-[(5-Chloro-2-pyrimidinyl)oxy]-3,4-dihydro-4-(3,3,3-trifluoropropyl)-1H-2-benzopyran-1-one;
5-[(5-Chloro-2-pyrimidinyl)oxy]-1,4-dihydro-4-(4,4,4-trifluorobutyl)-3H-2-benzopyran-3-one;
5-Chloro-2-[[3,4-dihydro-1-(4,4,4-trifluorobutyl)-1H-2-benzopyran-8-yl]oxy]pyrimidine;
8-[(5-Chloro-2-pyrimidinyl)oxy]-1,4-dihydro-1-(3,3,3-trifluoropropyl)-3H-2-benzopyran-3-one;
5-[(5-Chloro-2-pyrimidinyl)oxy]-1,4-dihydro-4-(3,3,3-trifluoropropyl)-3H-2-benzopyran-3-one;
5-[(5-Chloro-2-pyrimidinyl)oxy]-3,4-dihydro-4-(4,4,4-trifluorobutyl)-1(2H)-naphthalenone;
5-[(5-Chloro-2-pyrimidinyl)oxy]-3,4-dihydro-3-(5,5,5-trifluoropentyl)-1H-2-benzopyran-1-one;
5-Chloro-2-[[3,4-dihydro-1-(3,3,3-trifluoropropyl)-1H-2-benzopyran-8-yl]oxy]pyrimidine;
5-Chloro-2-[[2,3-dihydro-3-(4,4,4-trifluorobutyl)-4-benzofuranyl]oxy]pyrimidine;
5-[(5-Chloro-2-pyrimidinyl)oxy]-1,4-dihydro-4-(5,5,5-trifluoropentyl)-3H-2-benzopyran-3-one;
8-[(5-Chloro-2-pyrimidinyl)oxy]-1,4-dihydro-1-propyl-3H-2-benzopyran-3-one; and
5-Chloro-2-[[2,3-dihydro-3-(3,3,3-trifluoropropyl)-4-benzofuranyl]oxy]pyrimidine.

This disclosure also relates to a method for controlling undesired vegetation comprising applying to the locus of the vegetation herbicidally effective amounts of the compounds of the disclosure (e.g., as a composition described herein). Of note as embodiments relating to methods of use are those involving the compounds of embodiments described above. Compounds of the disclosure are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present disclosure comprising the compounds of embodiments described above.

This disclosure also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the Q$_B$-binding niche and thus block electron transport from Q$_A$ to Q$_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The Q$_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzene sulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl] sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propan amide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl) carbonyl]-2-(3-methoxyphenyl)-3-(3-methoxypropyl)-4 (3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3, 6-difluorophenyl)-4-hydroxy-1-methyl-1,5-naphthyridin-2 (1H)-one, 7-(3,5-dichloro-4-pyridinyl)-5-(2,2-difluoroethyl)-8-hydroxypyrido[2,3-b]pyrazin-6(5H)-one and 4-(2, 6-diethyl-4-methylphenyl)-5-hydroxy-2,6-dimethyl-3 (2H)-pyridazinone.

HST inhibitors also include compounds of Formulae A and B.

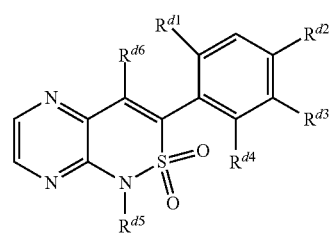

A

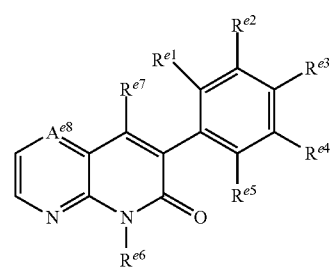

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 54[[(2,6-difluorophenyl)methoxy]methyl]-4,5-dihydro-5-methyl-3-(3-methyl-2-thienyl)isoxazole.

"Other herbicides" (b15) also include a compound of Formula (b15A)

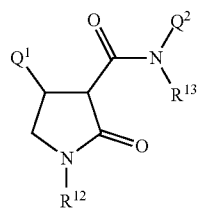

(b15A)

wherein
$R^{12}$ is H, $C_1$-$C_6$ alkyl, $C_1$-$C_6$ haloalkyl or $C_4$-$C_8$ cycloalkyl;

$R^{13}$ is H, $C_1$-$C_6$ alkyl or $C_1$-$C_6$ alkoxy;

$Q^1$ is an optionally substituted ring system selected from the group consisting of phenyl, thienyl, pyridinyl, benzodioxolyl, naphthyl, naphthalenyl, benzofuranyl, furanyl, benzothiophenyl and pyrazolyl, wherein when substituted said ring system is substituted by 1 to 3 $R^{14}$;

$Q^2$ is an optionally substituted ring system selected from the group consisting of phenyl, pyridinyl, benzodioxolyl, pyridinonyl, thiadiazolyl, thiazolyl, and oxazolyl, wherein when substituted said ring system is substituted by 1 to 3 $R^{15}$;

each $R^{14}$ is independently halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, cyano, $C_1$-$C_6$ alkylthio, $C_1$-$C_6$ alkylsulfinyl, $C_1$-$C_6$ alkylsulfonyl, $SF_5$, $NHR^{17}$; or phenyl optionally substituted by 1 to 3 $R^{16}$; or pyrazolyl optionally substituted by 1 to 3 $R^{16}$;

each $R^{15}$ is independently halogen, $C_1$-$C_6$ alkyl, $C_1$-$C_6$ haloalkyl, $C_1$-$C_6$ alkoxy, $C_1$-$C_6$ haloalkoxy, cyano, nitro, $C_1$-$C_6$ alkylthio, $C_1$-$C_6$ alkylsulfinyl, $C_1$-$C_6$ alkylsulfonyl;

each $R^{16}$ is independently halogen, $C_1$-$C_6$ alkyl or $C_1$-$C_6$ haloalkyl;

$R^{17}$ is $C_1$-$C_4$ alkoxycarbonyl.

In one Embodiment wherein "other herbicides" (b15) also include a compound of Formula (b15A), it is preferred that $R^{12}$ is H or $C_1$-$C_6$ alkyl; more preferably $R^{12}$ is H or methyl. Preferably $R^{13}$ is H. Preferably $Q^1$ is either a phenyl ring or a pyridinyl ring, each ring substituted by 1 to 3 $R^{14}$; more preferably $Q^1$ is a phenyl ring substituted by 1 to 2 $R^{14}$. Preferably $Q^2$ is a phenyl ring substituted by 1 to 3 $R^{15}$; more preferably $Q^2$ is a phenyl ring substituted by 1 to 2 $R^{15}$. Preferably each $R^{14}$ is independently halogen, $C_1$-$C_4$ alkyl, $C_1$-$C_3$ haloalkyl, $C_1$-$C_3$ alkoxy or $C_1$-$C_3$ haloalkoxy; more preferably each $R^{14}$ is independently chloro, fluoro, bromo, $C_1$-$C_2$ haloalkyl, $C_1$-$C_2$ haloalkoxy or $C_1$-$C_2$ alkoxy. Preferably each $R^{15}$ is independently halogen, $C_1$-$C_4$ alkyl, $C_1$-$C_3$ haloalkoxy; more preferably each $R^{15}$ is independently chloro, fluoro, bromo, $C_1$-$C_2$ haloalkyl, $C_1$-$C_2$ haloalkoxy or $C_1$-$C_2$ alkoxy. Specifically preferred as "other herbicides" (b15) include any one of the following (b15A-1) through (b15A-15):

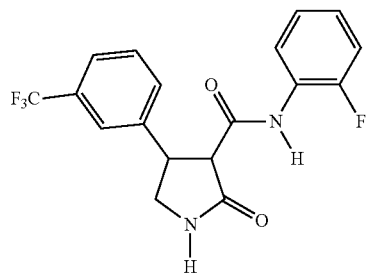

(b15A-1)

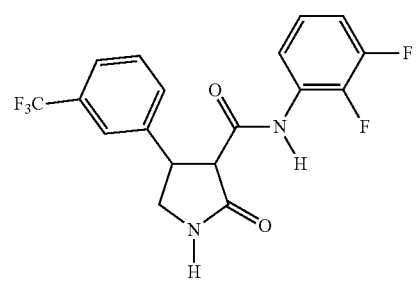

(b15A-2)

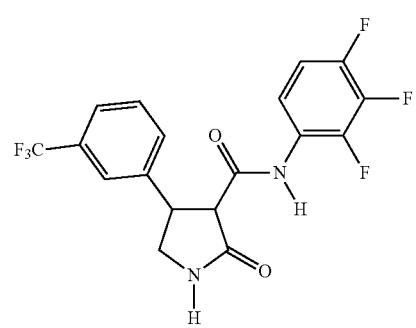

(b15A-3)

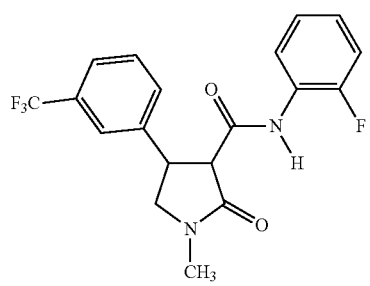

(b15A-4)

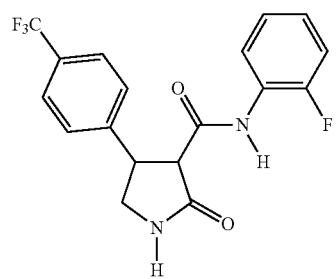

(b15A-5)

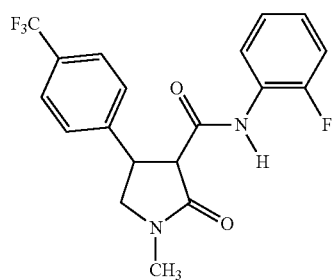
(b15A-6)
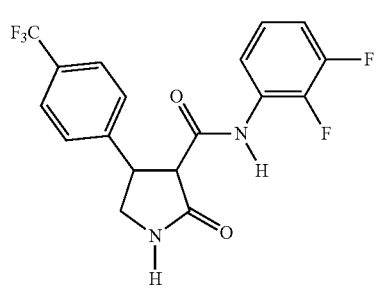
(b15A-7)
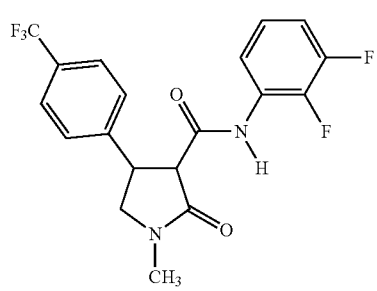
(b15A-8)
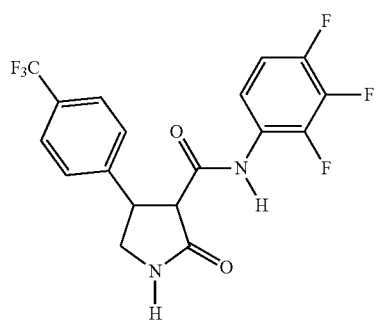
(b15A-9)
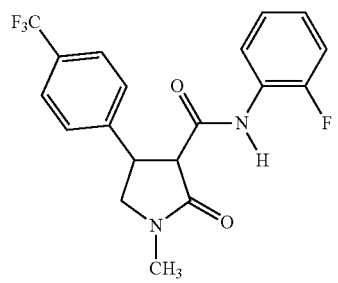
(b15A-10)
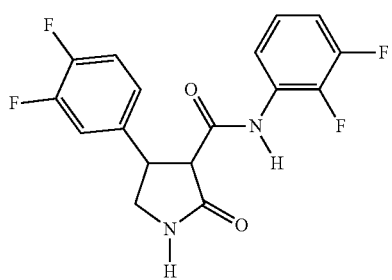
(b15A-11)
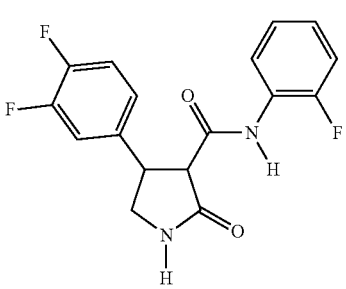
(b15A-12)
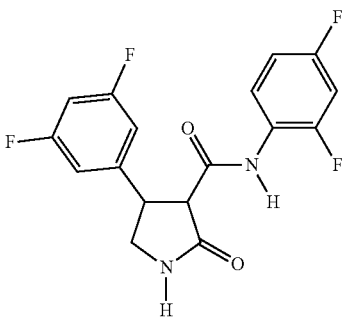
(b15A-13)
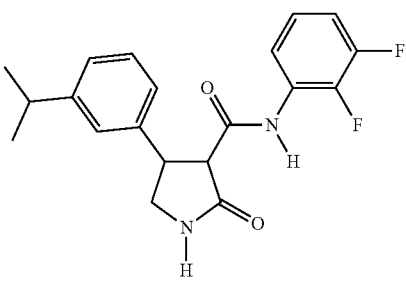
(b15A-14)
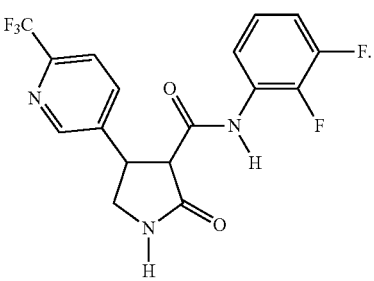
(b15A-15)

"Other herbicides" (b15) also include a compound of Formula (b15B)

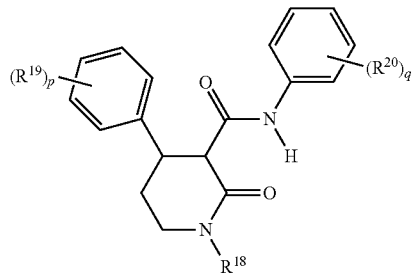
(b15B)

wherein
$R^{18}$ is H, $C_1$-$C_6$ alkyl, $C_1$-$C_6$ haloalkyl or $C_4$-$C_8$ cycloalkyl;
each $R^{19}$ is independently halogen, $C_1$-$C_6$ haloalkyl or $C_1$-$C_6$ haloalkoxy;
p is an integer of 0, 1, 2 or 3;
each $R^{20}$ is independently halogen, $C_1$-$C_6$ haloalkyl or $C_1$-$C_6$ haloalkoxy; and
q is an integer of 0, 1, 2 or 3.

In one Embodiment wherein "other herbicides" (b15) also include a compound of Formula (b15B), it is preferred that $R^{18}$ is H, methyl, ethyl or propyl; more preferably $R^{18}$ is H or methyl; most preferably $R^{18}$ is H. Preferrably each $R^{19}$ is independently chloro, fluoro, $C_1$-$C_3$ haloalkyl or $C_1$-$C_3$ haloalkoxy; more preferably each $R^{19}$ is independently chloro, fluoro, $C_1$ fluoroalkyl (i.e. fluoromethyl, difluoromethyl or trifluoromethyl) or $C_1$ fluoroalkoxy (i.e. trifluoromethoxy, difluoromethoxy or fluoromethoxy). Preferably each $R^{20}$ is independently chloro, fluoro, $C_1$ haloalkyl or $C_1$ haloalkoxy; more preferably each $R^{20}$ is independently chloro, fluoro, $C_1$ fluoroalkyl (i.e. fluoromethyl, difluoromethyl or trifluromethyl) or $C_1$ fluoroalkoxy (i.e. trifluoromethoxy, difluoromethoxy or fluoromethoxy). Specifically preferred as "other herbicides" (b15) include any one of the following (b15B-1) through (b15B-19):

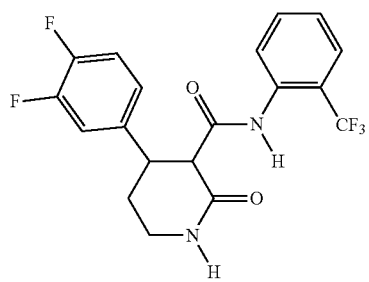
(b15B-1)

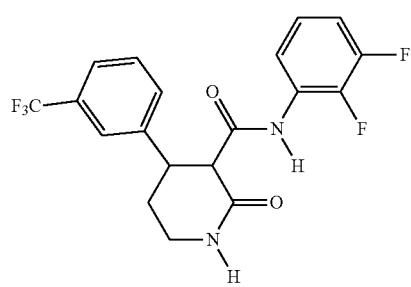
(b15B-2)

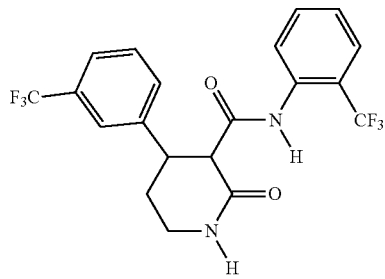
(b15B-3)

(b15B-4)

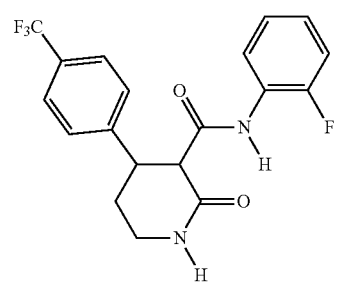
(b15B-5)

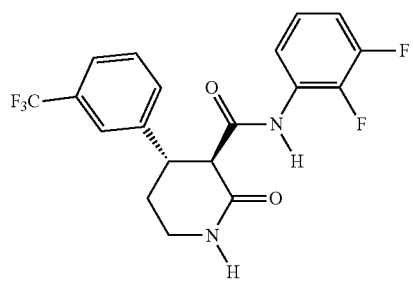
(b15B-6)

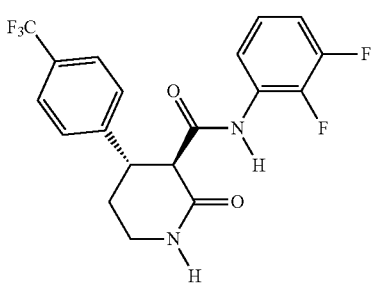
(b15B-7)

-continued
(b15B-8)
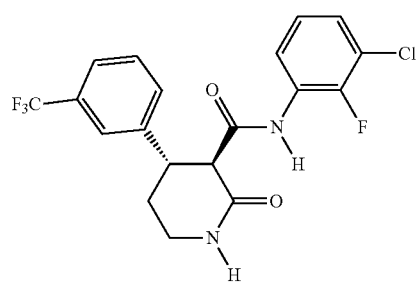
(b15B-9)
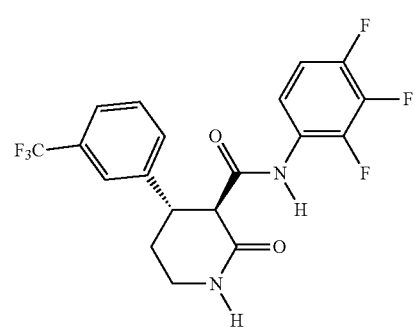
(b15B-10)
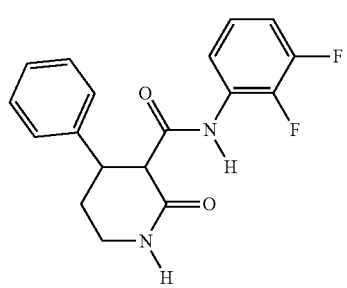
(b15B-11)
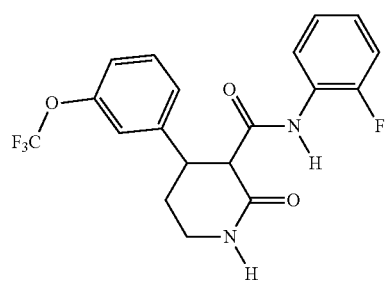
(b15B-12)
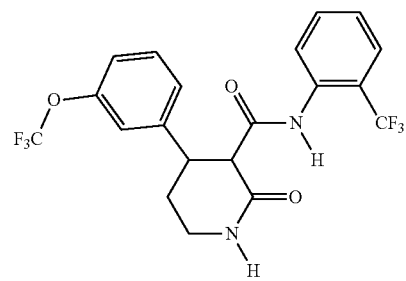
-continued
(b15B-13)
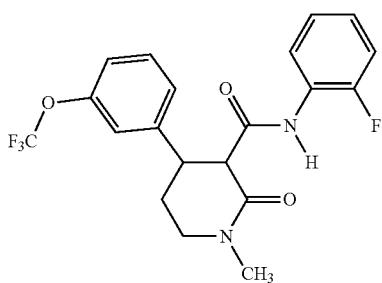
(b15B-14)
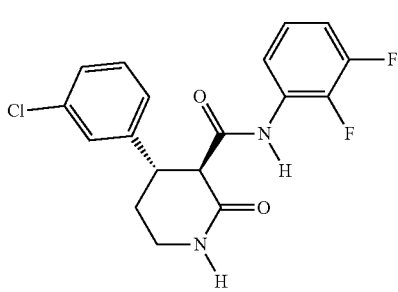
(b15B-15)
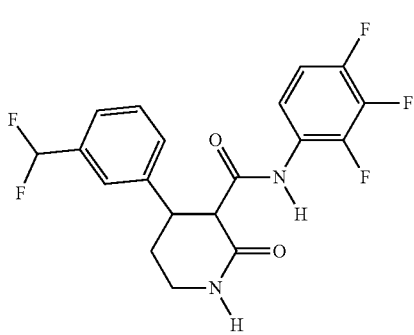
(b15B-16)
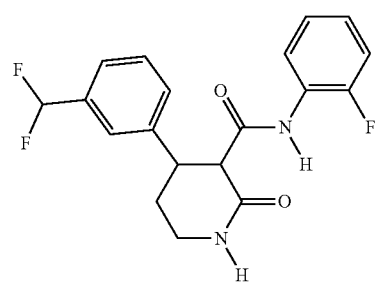
(b15B-17)
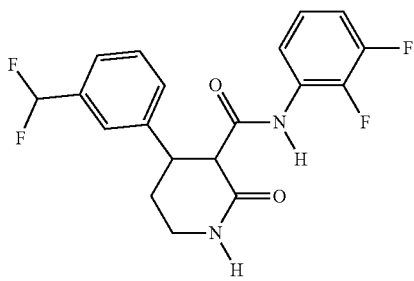

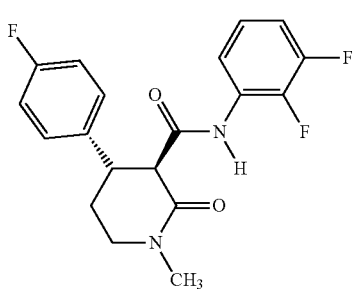

(b15B-18)

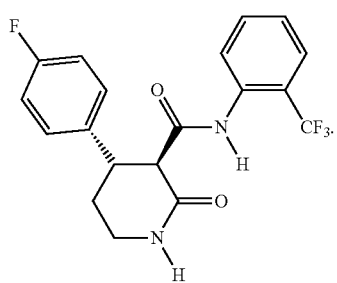

(b15B-19)

Another Embodiment wherein "other herbicides" (b15) also include a compound of Formula (b15C),

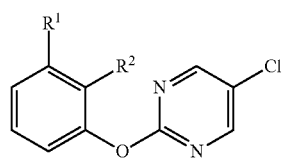

(b15C)

wherein R¹ is Cl, Br or CN; and R² is C(=O)CH$_2$CH$_2$CF$_3$, CH$_2$CH$_2$CH$_2$CH$_2$CF$_3$ or 3-CHF$_2$-isoxazol-5-yl.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[[(methylamino)carbonyl]amino]phenyl]sulfonyl]-benzamide.

Preferred for better control of undesired vegetation (e.g., lower use rate such as from enhanced effects, broader spectrum of weeds controlled, or enhanced crop safety) or for preventing the development of resistant weeds are mixtures of a compound of this invention with a herbicide selected from the group consisting of atrazine, azimsulfuron, beflubutamid, S-beflubutamid, benzisothiazolinone, carfentrazone-ethyl, chlorimuron-ethyl, chlorsulfuron-methyl, clomazone, clopyralid potassium, cloransulam-methyl, 2-[(2,4-dichlorophenyl)methyl]-4,4-dimethyl-isoxazolidinone, 2-[(2,5-dichlorophenyl)methyl]-4,4-dimethyl-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

An embodiment of the present disclosure is a herbicidal mixture comprising (a) a compound of Formula 1, and (b) at least one additional active ingredient selected from (b1) photosystem II inhibitors, (b2) acetohydroxy acid synthase (AHAS) inhibitors, (b4) auxin mimics, (b5) 5-enol-pyruvyl-shikimate-3-phosphate (EPSP) synthase inhibitors, (b7) protoporphyrinogen oxidase (PPO) inhibitors, (b9) very long chain fatty acid (VLCFA) elongase inhibitors and (b12) 4-hydroxyphenyl-pyruvate dioxygenase (HPPD) inhibitors.

The compounds of Formula 1 can be prepared by general methods known in the art of synthetic organic chemistry. One or more of the following methods and variations as described in Schemes 1-11 can be used to prepare the compounds of Formula 1. The definitions of R, $R^{1a}$, $R^{1b}$, $R^2$, $R^3$, $R^4$, Z and K in the compounds of Formulae 1 through 18 below are as defined above in the Summary of the Invention unless otherwise noted. Compounds of Formulae 2a and 4a-4k are subsets of a compound of Formulae 2 and 4, respectively. Substituents for each subset formula are as defined for its parent formula unless otherwise noted.

As shown in Scheme 1 compounds of Formula 1 can be prepared by nucleophilic substitution by reaction of a compound of Formula 2 with a compound of Formula 3 in the presence of a base. Suitable bases include, but are not limited to, carbonate bases, such as cesium carbonate, potassium carbonate and sodium carbonate, and phosphate bases, such as potassium phosphate. A wide variety of solvents are suitable for the reaction including, but not limited to, toluene, acetonitrile, N,N-dimethylformamide, toluene, tetrahydrofuran or isopropyl alcohol. The reaction is conducted at temperatures ranging from −20° C. to the boiling point of the solvent, and typically from 0° C. to 120° C.

Scheme 1

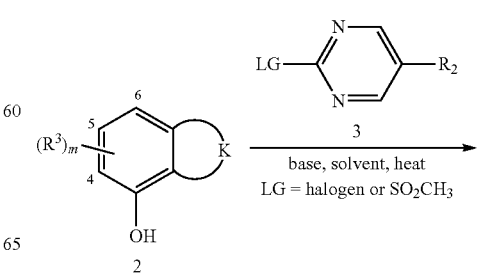

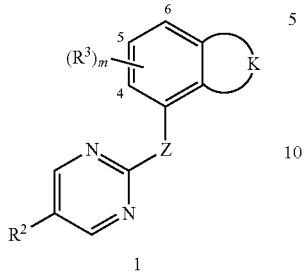

1

As shown in Scheme 2, a compound of Formula 2 can be prepared by deprotection of a compound of Formula 4 (wherein $R^{11}$ is $CH_3$, $C(=O)CH_3$, $CH_2OCH_3$, benzyl or p-methoxybenzyl) with a suitable deprotecting agent. Suitable methoxy (i.e. when $R^{11}$ is $CH_3$) deprotecting reagents such as $BBr_3$, $AlCl_3$ and HBr in acetic acid can be used in the presence of solvents such as toluene, dichloromethane and dichloroethane at a temperature of from −80 to 120° C. Suitable acetoxy (i.e. when $R^{11}$ is $C(=O)CH_3$) deprotecting agents include potassium carbonate, sodium carbonate or sodium hydroxide in methanol or ammonium acetate in aqueous methanol at room temperature as discussed in Das, et al., *Tetrahedron* 2003, 59, 1049-1054 and methods cited therein. Alternatively, a compound of Formula 4 can be combined with Amberlyst 15© in methanol (as discussed in Das, et al. *Tet. Lett.* 2003, 44, 5465-5468) or combined with sodium acetate in ethanol (as discussed in Narender, T., et al. Synthetic Communications 2009, 39(11), 1949-1956) to obtain a compound of Formula 2. A wide variety of benzyl ether deprotection methods are known in the literature. Methods well known to those skilled in the art include the use of Bronsted acids, Lewis acids, transition metals and oxidants. A variety of acetal protecting groups, such as methoxymethyl acetal (i.e when R=is $CH_2OCH_3$), are known in the literature as well. Methoxymethyl acetal deprotection methods well known to those skilled in the art include hydrolysis with aqueous acid, such as aqueous hydrochloric acid, or use of a Lewis acid, such as bromodimethylborane. Such deprotection agents and other useful substituted benzyl ether protecting and acetal groups suitable for use in preparing a compound of Formula 2 can be found in Greene, T. W.; Wuts, P. G. M. Protective Groups in Organic Synthesis, 4th ed.; Wiley: Hoboken, N.J., 1991.

Scheme 2

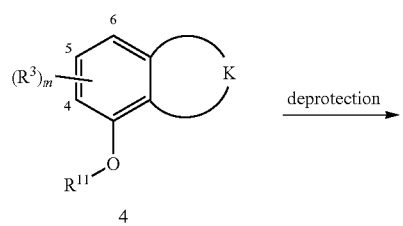

4

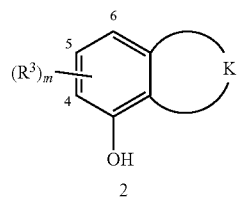

2 where $R^{11}$ is $CH_3$, $COCH_3$, $CH_2OCH_3$, benzyl or para-methoxybenzyl

As shown in Scheme 3, compounds of Formula 4a can be obtained by the metal-halogen exchange of X in Formula 5 and subsequent in situ cyclization of the resulting aryl metal species. A wide variety of methods for metal-halogen exchange are known in the literature. Methods well known to those skilled in the art include metal-halogen exchange with organolithium or organomagnesium reagents. For an example using tert-butyllithium, see *Chemical Science* 2015, 6, 5440-5445.

Scheme 3

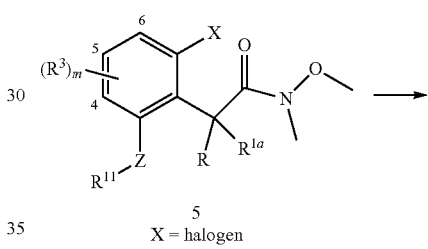

5
X = halogen

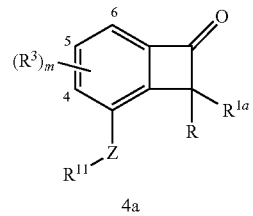

4a

As shown in Scheme 4 a compound of Formula 4c can be prepared through deoxygenation of a compound of Formula 4b. One method utilizes a transition metal catalyst in the presence of a reducing agent and utilizing a number of solvents, including methanol and ethanol. A typical transition metal catalyst is palladium on carbon, and standard reducing agents include hydrogen gas, either at atmospheric or elevated pressure, ammonium formate and silanes (for an example utilizing palladium dichloride and triethyl silane, see *Tet. Let.* 2009, 50, 5930-5932). A second method employs a hydride source in combination with an acid. Typical hydride sources include triethylsilane and sodium borohydride, in combination with Bronsted acids such as trifluoroacetic acid, sulfuric and acetic acid, or Lewis acids such as boron trifluoride etherate. The solvent for these reactions can be the acid alone or as a mixture with a number of other common solvents such as dichloromethane or acetonitrile.

Scheme 4

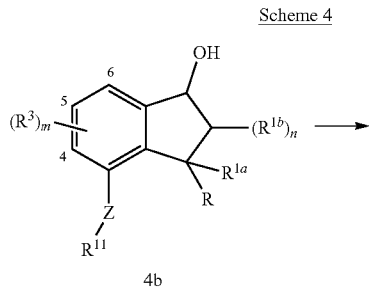

4b

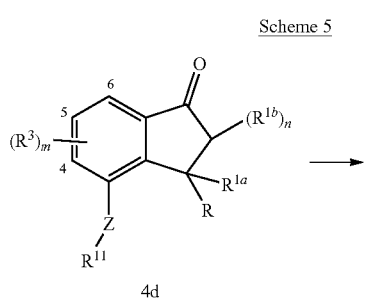

4c

As shown in Scheme 5, benzylic alcohols of Formula 4b can be prepared by reduction of ketones of Formula 4d by a wide variety of methods well known to those skilled in the art. Suitable reducing agents for the reaction include, but are not limited to, sodium borohydride, lithium aluminum hydride, and diisobutylaluminium hydride. A variety of solvents are also suitable for this reaction and include, but are not limited to, methanol, ethanol, dichloromethane, toluene, ether and tetrahydrofuran with typically reaction temperatures ranging from −78° C. to 25° C.

Scheme 5

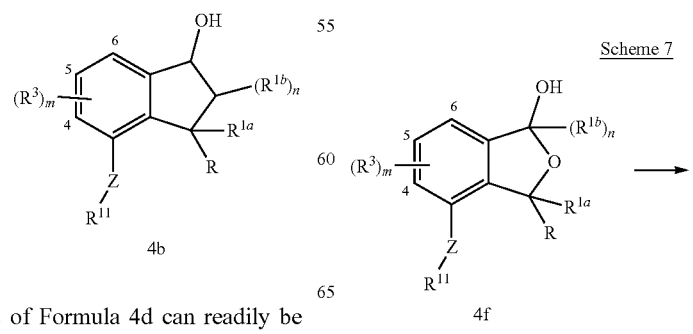

4d

4b

In Scheme 6, compounds of Formula 4d can readily be prepared by alkylation of the dianion of an indanone of Formula 4e. The alkylation can be accomplished using an appropriate base and alkylating reagent. Suitable bases generally include but are not limited to butyllithium and lithium diisopropyl amide (for an example using lithium diisopropyl amide, see *J. O. C.* 1977, 42, 3212-3214). Suitable alkylating agents include, but are not limited to, trialkyloxonium tetrafluoroborates such as trimethyloxonium tetrafluoroborate and triethyloxonium tetrafluoroborate, alkyliodides, alkylbromides, and alkyl sulfonates. Suitable solvents for this reaction generally include, but are not limited to, ethereal solvents such as tetrahydrofuran, diethyl ether and dioxane, and reaction temperatures range from −78° C. to 0° C. as described in synthesis Example 2, Step B.

Scheme 6

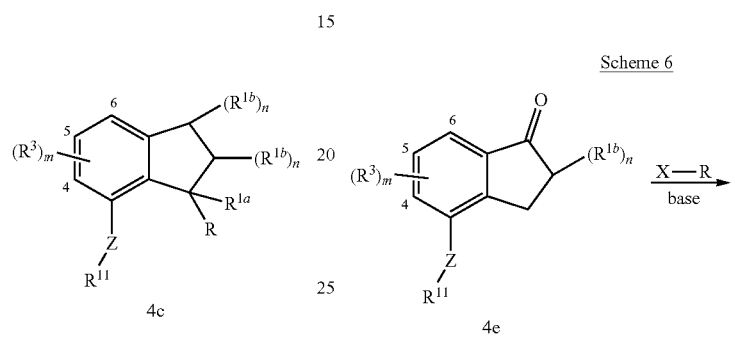

4e

4d

As shown in Scheme 7 a compound of Formula 4g can be prepared through deoxygenation of a compound of Formula 4f. The deoxygenation can typically be accomplished with a hydride source in the presence of a Bronsted or Lewis acid. Typical hydride sources include organosilanes and borohydride reagents (for an example using triethylsilane, see *Synthesis* 2011, 14, 2215-2222, and for an example using sodium borohydride, see JP 2002114770). Typical Bronsted acids include, but are not limited to acedic acid, sulfuric acid, trifluoroacetic acid and trifluoromethylsulfonic acid, and typical Lewis acids include boron trifluoride diethyl etherate and trimethylsilyl triflate. The solvent for these reactions can be the acid alone or as a mixture with a number of other common solvents such as dichloromethane or acetonitrile.

Scheme 7

4f

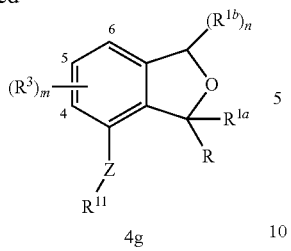

4g

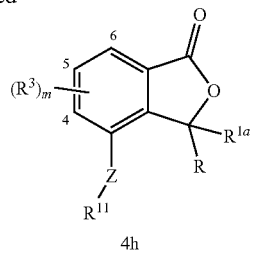

4h

As shown in Scheme 8, compounds of Formula 4f can be prepared reduction of lactones of Formula 4h. The reaction is typically carried out with a suitable metal hydride reductant, which includes, but is not limited to lithium aluminum hydride, diisobutylaluminum hydride, Red-Al, Super hydride and lithium borohydride. A variety of solvents are suitable for the reaction including, but not limited to methylene chloride, benzene, toluene, diethyl ether and tetrahydrofuran. The reaction is conducted at temperatures ranging from −78° C. to the boiling point of the solvent, and typically between −78° C. and 25° C. See *Bioorganic & Medicinal Chemistry Letters* 2007, 17, 3344-3348 for conditions using diisobutylaluminum hydride.

Scheme 8

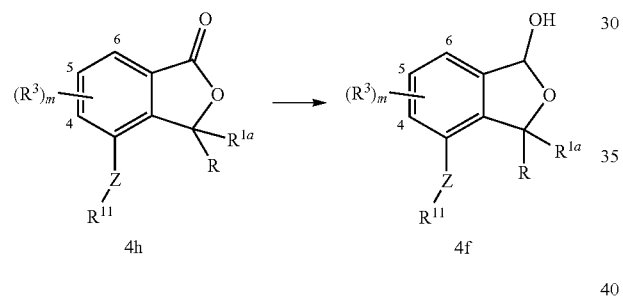

As shown in Scheme 9, a compound of Formula 4h can be prepared by reaction of organometallic reagents, such as organomagnesium or organolithium reagents, with compounds of the Formula 4i. This reaction is typically carried out in an ethereal solvent, such as tetrahydrofuran or diethyl ether, at temperatures ranging from −78° C. to the boiling point of the solvent. An example of this reaction can be found in the *J. O. C.* 2006, 71, 5864 or as described in Step A of synthesis Example 3.

Scheme 9

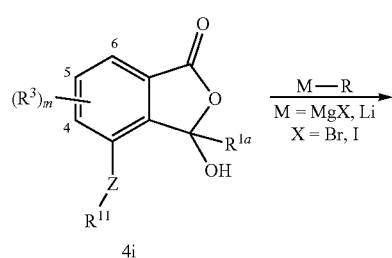

As shown in Scheme 10, a compound of Formula 4j can be prepared by the cyclization of compounds of the Formula 5 in the presence of a suitable transition metal catalyst and base. Suitable transition metals include, but are not limited to, palladium and copper (for an example using palladium acetate, see *J. A. C. S.* 2006, 128, 14242-14243, and for an example using copper iodide, see *Angewandte Chemie, International Edition* 2015, 54, 14447-14451). Suitable bases include, but are not limited to, hydroxides such as sodium and potassium hydroxide, carbonates such as cesium, sodium and potassium carbonate, and sodium hydride. A wide variety of solvents are suitable for the reaction including, but not limited to, toluene, tetrahydrofuran, acetonitrile, acetone, N,N-dimethylformamide, dimethylsulfoxide. The reaction is conducted at temperatures ranging from 25° C. to the boiling point of the solvent.

Scheme 10

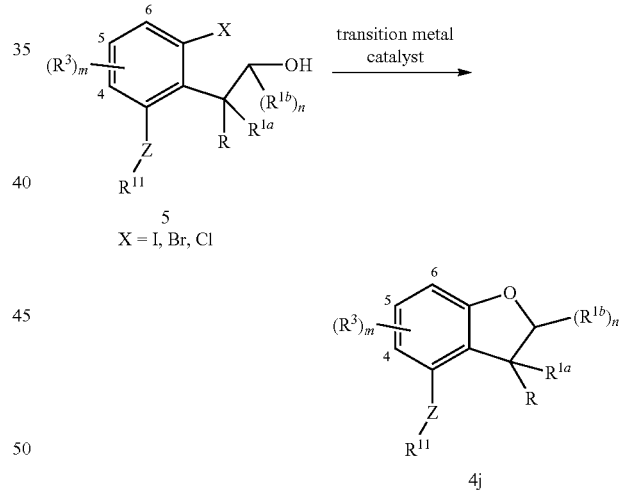

In Scheme 11, compounds of Formula 4k can readily be prepared by alkylation of the dianion of an isoindolinone of Formula 6 with a suitable alkylating agent. The dianion can be generated with an appropriate organometalic base, such as an organolithium or lithium amide bass (for an example using lithium diisopropyl amide, see *Tetrahedron Letters* 1998, 42, 2319-2320). Suitable alkylating agents include, but are not limited to, trialkyloxonium tetrafluoroborates such as trimethyloxonium tetrafluoroborate and triethyloxonium tetrafluoroborate, alkyliodides, alkylbromides, and alkyl sulfonates. Suitable solvents for this reaction generally include, but are not limited to, ethereal solvents such as tetrahydrofuran, diethyl ether and dioxane. Reaction temperatures range from −78° C. to 0° C.

Scheme 11

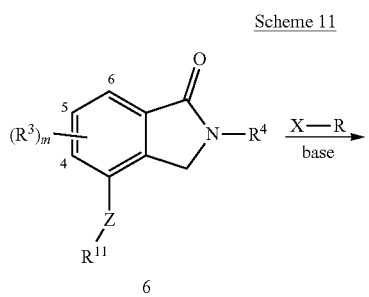

6

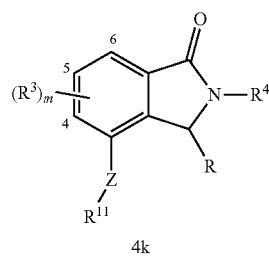

4k

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present disclosure to its fullest extent. The following non-limiting Examples are illustrative of the disclosure. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. Mass spectra (MS) are reported as the molecular weight of the highest isotopic abundance parent ion (M+1) formed by addition of H+(molecular weight of 1) to the molecule, or (M−1) formed by the loss of H+(molecular weight of 1) from the molecule, observed by using liquid chromatography coupled to a mass spectrometer (LCMS) using either atmospheric pressure chemical ionization (AP+) where "amu" stands for unified atomic mass units or electrospray ionization (ES+).

Example 1

Preparation of 5-chloro-2-[[1,3-dihydro-3-(4,4,4-trifluorobutyl)-4-isobenzofuranyl]oxy]-pyrimidine (Compound 7)

Step A: Preparation of 3-(4,4,4-trifluorobutyl)-1,3-dihydroisobenzofuran-4-ol

A solution of 4-hydroxy-3-(4,4,4-trifluorobutyl)-3H-isobenzofuran-1-one (0.200 g, 0.768 mmol, 1.0 eq.) in tetrahydrofuran (THF) (4 mL) was cooled to −78° C. To this was slowly added a 1 M solution of diisobutylaluminium hydride (DIBAL-H) in toluene (1.77 mL, 1.77 mmol, 2.3 eq). The mixture was stirred at −78° C. for 2 h. The ice bath was removed and the reaction was quenched with a saturated aqueous solution of Rochelle salt. The mixture was further diluted with ethyl acetate (8 mL) and stirred at room temperature for 2 h. The organic phase was separated, washed with brine, dried and concentrated in vacuo. The crude residue was dissolved in dichloromethane (4 mL) and treated with triethylsilane (0.491 mL, 3.07 mmol, 4.0 eq.). After 15 min., trifluoroacetic acid (0.235 mL, 3.07 mmol, 4.0 equiv) was added and the mixture was heated at 45° C. for 2 h. The reaction mixture was cooled to room temperature and concentrated onto Celite® diatomaceous earth filter aid. The crude material was purified by column chromatography eluting with 0 to 30% ethyl acetate in hexanes to afford the desired product (45.0 mg, 24%).

$^1$H NMR (500 MHz, CDCl$_3$) δ 7.25-7.12 (m, 1H), 6.87-6.77 (m, 1H), 6.68-6.57 (m, 1H), 5.52-5.39 (m, 1H), 5.20-5.03 (m, 2H), 4.53 (br s, 2H), 2.21-2.08 (m, 3H), 1.96-1.84 (m, 1H), 1.75-1.60 (m, 2H).

Step B: 5-chloro-2-[[1,3-dihydro-3-(4,4,4-trifluorobutyl)-4-isobenzofuranyl]oxy]-pyrimidine To a stirred solution of 3-(4,4,4-trifluorobutyl)-1,3-dihydroisobenzofuran-4-ol (i.e. the product obtained in Step A, 45.0 mg, 0.182 mmol, 1.0 eq.) and 5-chloro-2-methylsulfonyl-pyrimidine (42.0 mg g, 0.218 mmol, 1.2 eq.) in acetonitrile (2 mL) was added potassium carbonate (37.7 mg, 0.273 mmol, 1.5 eq.). The reaction mixture was heated at 60° C. for 2 h. After cooling to room temperature, the mixture was filtered through a pad Celite® diatomaceous earth filter aid.

The filtrate was concentrated in vacuo and the crude material was purified by column chromatography, eluting with 0 to 30% ethyl acetate in hexanes to afford the desired product (51.0 mg, 78%). AP+ 359.1.

Example 2

Preparation of 4-[(5-Chloropyrimidin-2-pyrimidinyl)oxy]-2,3-dihydro-3-(4,4,4-trifluorobutyl)-1H-inden-1-one (Compound 6)

Step A: Preparation of 4-[tert-butyl(dimethyl)silyl]oxyindan-1-one

To a stirred solution of 4-hydroxy-indan-1-one (5.0 g, 33.7 mmol, 1.0 eq.) in N,N-dimethylformamide (112 mL) was added imidazole (5.47 g, 84.2 mmol, 2.5 eq.) and tert-butyldimethylsilyl chloride (6.61 g, 43.8 mmol, 1.3 eq.). The reaction mixture was stirred at room temperature for 18 h. The mixture was diluted with ethyl acetate (250 mL) and washed 3 times with water, then once with brine. The organic phase was dried and concentrated in vacuo. The crude residue was purified by column chromatography, eluting with 0 to 15% ethyl acetate in hexanes to afford the desired product (8.03 g, 91%).

$^1$H NMR (500 MHz, CDCl$_3$) δ 7.38 (d, J=7.6 Hz, 1H), 7.29-7.23 (m, 1H), 7.03-6.96 (m, 1H), 3.07-3.00 (m, 2H), 2.70-2.63 (m, 2H), 1.03 (s, 9H), 0.26 (s, 6H).

Step B: Preparation of 4-[tert-butyl(dimethyl) silyl]oxy-3-(4,4,4-trifluorobutyl)indan-1-one To a stirred solution of diisopropylamine (5.11 mL, 36.5 mmol, 2.37 equiv) in dry tetrahydrofuran (25 mL) at −78° C. was added a 2.5 M solution of n-butyllithium in hexanes (13.4 mL, 33.6 mmol, 2.18 eq.). After 1 h, a solution of 4-[tert-butyl(dimethyl)silyl]oxyindan-1-one (i.e. the product of Step A) in dry tetrahydrofuran (65 mL) was slowly added via addition funnel. The mixture was stirred for 1 h at −78° C. before it was allowed to warm to room temperature and stir for an additional 3 h. The reaction mixture was cooled to −20° C. and a solution of 1-bromo-4,4,4-trifluobutane (2.29 mL, 18.5 mmol, 1.2 eq.) in dry tetrahydrofuran (10 mL) was added rapidly. After 1 h, the reaction was acidified with 1 N HCl and extracted with ethyl acetate (3×). The organics were combined, washed with brine, dried and concentrated in vacuo. The crude residue was purified by column chromatography to afford the desired product (3.45 g, 60%).

$^1$H NMR (500 MHz, CDCl$_3$) δ 7.37-7.34 (m, 1H), 7.28-7.25 (m, 1H), 7.03-7.00 (m, 1H), 3.48-3.35 (m, 1H), 2.88-2.80 (m, 1H), 2.43-2.34 (m, 1H), 2.29-2.16 (m, 1H), 2.13-2.03 (m, 2H), 1.61-0.54 (m, 2H), 1.04 (m, 9H), 0.31 (m, 3H), 0.25 (m, 3H).

Step C: Preparation of 4-hydroxy-3-(4,4,4-trifluorobutyl)indan-1-one

To a stirred solution of 4-[tert-butyl(dimethyl)silyl]oxy-indan-1-one (i.e. the product obtained in Step B, 0.300 g, 0.805 mmol, 1.0 eq.) in 95:5 acetonitrile/water (2 mL) was added 1,8-diazabicyclo(5.4.0)undec-7-ene (DBU) (0.122 g, 0.805 mmol, 1.0 eq.). The reaction was stirred at room temperature until the reaction was complete as indicated by thin layer chromatography (TLC). The reaction was diluted with ethyl acetate, washed with brine and concentrated onto Celite® diatomaceous earth filter aid for purification by column chromatography. The desired product eluted with 0 to 30% ethyl acetate in hexanes (0.179 g, 86%).

$^1$H NMR (500 MHz, CDCl$_3$) δ 7.35 (d, J=7.6 Hz, 1H), 7.29-7.24 (m, 2H), 7.01-6.97 (m, 1H), 5.67 (s, 1H), 3.57-3.49 (m, 1H), 2.93-2.81 (m, 1H), 2.42 (dd, J=19.1, 2.5 Hz, 1H), 2.28-2.19 (m, 1H), 2.18-2.07 (m, 2H), 1.66-1.46 (m, 3H).

Step D: Preparation of 4-[(5-Chloropyrimidin-2-pyrimidinyl)oxy]-2,3-dihydro-3-(4,4,4-trifluorobutyl)-1H-inden-1-one To a stirred solution of 4-hydroxy-3-(4,4,4-trifluorobutyl)indan-1-one (i.e. the product obtained in Step C, 0.179 g, 0.693 mmol, 1.0 eq.) and 2,5-dichloropyrimidine (0.124 g, 0.831 mmol, 1.2 eq.) in acetonitrile (2.5 mL) was added potassium carbonate (0.144 g, 1.04 mmol, 1.5 eq.). The reaction was heated at 60° C. for 4 h. The reaction mixture was cooled to room temperature and filtered through a pad Celite® diatomaceous earth filter aid. The filtrate was concentrated in vacuo and the crude material was purified by column chromatography, eluting with 0 to 30% ethyl acetate in hexanes to afford the desired product (0.183 g, 71%). AP+371.1.

Example 3

Preparation of 4-[(5-Chloro-2-pyrimidinyl)oxy]-3-(4,4,4-trifluorobutyl)-1(3H)-isobenzofuranone (Compound 1)

Step A: Preparation of 3-trifluorobutyl-4-methoxy-3H-isobenzofuran-1-one

A round-bottom flask was charged with Mg turnings (0.292 g, 12.0 mmol, 2.4 eq.), and the vessel was heated with a heat gun under vacuum and backfilled with nitrogen. Anhydrous tetrahydrofuran (12.5 mL) and 5-bromo-1,1,1-trifluoro-pentane (0.35 mL) were then added and the suspension was heated to 80° C. Diisobutylaluminium hydride (DIBAL-H) (0.075 mL, 1.0 M in tetrahydrofuran, 0.075 mmol, 0.015 eq.) was then added at 80° C. to facilitate initiation of Grignard formation. Once the Grignard formation initiated, the remaining 5-bromo-1,1,1-trifluoro-pentane (1.0 mL) was added slowly and the reaction was allowed to reflux for 1 h. After the reaction mixture was allowed to cool to room temperature, a solution of 3-hydroxy-4-methoxy-3H-isobenzofuran-1-one (prepared as described in Dischmann, Mike; Frassetto, Timo; Breuning, M. Andre; Koert, Ulrich Chemistry—A European Journal 2014, 20 (36), pp 11300-11302, 0.901 g, 5.0 mmol, 1.0 eq.) in tetrahydrofuran (12.5 mL) was added. The mixture was again heated to 80° C., stirred at this temperature for 30 min, and subsequently cooled to 0° C., treated with a 10% aqueous solution of HCl and heated to 40° C. After stirring for 1 h at 40° C., the reaction was cooled to room temperature and extracted three times with diethyl ether. The organic portions were combined, washed with brine, dried with MgSO$_4$ and filtered. The filtrate was concentrated and the resulting residue was purified by column chromatography (0-30% ethyl acetate in hexanes) to afford 3-trifluorobutyl-4-methoxy-3H-isobenzofuran-1-one as a colorless solid (1.11 g, 81% yield).

$^1$H NMR (500 MHz, CDCl$_3$) δ 7.46-7.52 (m, 2H), 7.12-7.13 (m, 1H), 5.48-5.50 (m, 1H), 3.93 (s, 3H), 2.34-2.41 (m, 1H), 2.10-2.20 (m, 2H), 1.66-1.84 (m, 3H).

Step B: Preparation of 3-trifluorobutyl-4-hydroxy-3H-isobenzofuran-1-one

To an oven-dried vial was added 3-trifluorobutyl-4-methoxy-3H-isobenzofuran-1-one (0.549 g, 2.00 mmol, 1.0 eq.) and dichloromethane. The resulting solution was cooled to −30° C., and a solution of $BBr_3$ (4.20 mL, 1.0 M in dichloromethane, 4.20 mmol, 2.1 eq.) was added dropwise. After stirring for 1 h at −30° C., the reaction mixture was allowed to warm to room temperature and stir for 2 h at this temperature. The mixture was then diluted with water and extracted three times with dichloromethane. The organic portions were pooled, washed with brine, dried with $MgSO_4$ and filtered. The filtrate was concentrated and the resulting residue was purified with column chromatography (eluting with 20-80% ethyl acetate in hexanes) to afford 3-trifluorobutyl-4-hydroxy-3H-isobenzofuran-1-one as a colorless solid (0.121 g, 23% yield).

$^1$H NMR (500 MHz, DMSO-$d_6$) δ 10.49 (s, 1H), 7.41-7.44 (m, 1H), 7.27-7.33 (m, 1H), 7.12-7.15 (m, 1H), 5.64-5.66 (m, 1H), 2.24-2.43 (m, 3H), 1.69-1.77 (m, 1H), 1.46-1.64 (m, 2H).

Step C: Preparation of 4-[(5-Chloro-2-pyrimidinyl)oxy]-3-(4,4,4-trifluorobutyl)-1(3H)-isobenzofuranone An oven-dried vial was charged with 3-trifluorobutyl-4-hydroxy-3H-isobenzofuran-1-one (i.e. the product of Step B, 106 mg, 0.407 mmol, 1.0 eq.), 2,5-dichloropyrimidine (73 mg, 0.489 mmol, 1.2 eq.), $K_3PO_4$ (173 mg, 0.814 mmol, 2.0 eq.) and toluene (0.82 mL), and the resulting mixture was heated to 110° C. After stirring for 3 h at 110° C., the reaction mixture was cooled to room temperature and concentrated. The residue was purified by column chromatography (eluting with 10-30% ethyl acetate in hexanes) to afford 4-[(5-Chloro-2-pyrimidinyl)oxy]-3-(4,4,4-trifluorobutyl)-1(3H)-isobenzofuranone as a colorless oil (0.130 g, 86% yield).

$^1$H NMR (500 MHz, $CDCl_3$) δ 8.51-8.55 (m, 2H), 7.81-7.87 (m, 1H), 7.61-7.64 (m, 1H), 7.47-7.48 (m, 1H), 5.49-5.51 (m, 1H), 2.17-2.25 (m, 1H), 1.98-2.13 (m, 2H), 1.72-1.81 (m, 1H), 1.61-1.70 (m, 2H).

Step D: Preparation of (3S)-4-[(5-Chloro-2-pyrimidinyl)oxy]-3-(4,4,4-trifluorobutyl)-1(3H)-isobenzofuranone and (3R)-4-[(5-Chloro-2-pyrimidinyl)oxy]-3-(4,4,4-trifluorobutyl)-1(3H)-isobenzofuranone The enantiomers of 4-[(5-Chloro-2-pyrimidinyl)oxy]-3-(4,4,4-trifluorobutyl)-1(3H)-isobenzofuranone were separated by chiral supercritical fluid chromatography using a Lux C2 column. The mobile phase was liquid $CO_2$ and 20 mM ammonia in methanol as the co-solvent at a flow rate of 3 mL/min (2.4 ml/min for $CO_2$+0.6 mL/min for the co-solvent). A 320 mg sample of 4-[(5-Chloro-2-pyrimidinyl)oxy]-3-(4,4,4-trifluorobutyl)-1(3H)-isobenzofuranone was subjected to chiral separation using this method, yielding 120 mg of each enantiomer. The retention times of the enantiomers were 2.22 min and 2.67 min.

By the procedures described herein together with methods known in the art, the following compounds of Tables 1-1 to 15-105 can be prepared. The following abbreviations are used in the Tables which follow: Me means methyl, Et means ethyl, OMe means methoxy and —CN means cyano. Exhibit 2 below is used to describe specific values for variable R in Tables 1-1 to 15-105.

Exhibit 2

| R | R |
|---|---|
| butyl | 3,3,4,4,4-pentafluorobutoxy |
| tert-butyl | 2,2,3,3,3-pentafluoropropoxy |
| ethyl | 3,3,4,4-tetrafluorobutoxy |
| hexyl | 2,2,3,3-tetrafluoropropoxy |
| isobutyl | 3,3,3-trichloropropoxy |
| isopentyl | 4,4,4-trifluorobutoxy |
| methyl | 2,2,2-trifluoroethoxy |
| pentyl | 6,6,6-trifluorohexoxy |
| propyl | 4,4,4-trifluoro-2-methyl-butoxy |
| benzyl | 3,3,3-trifluoropropoxy |
| allyl | 4-bromobut-3-ynoxy |
| 3-buten-1-yl | 4-chlorobut-3-ynoxy |
| 3-methyl-2-buten-1-yl | 3-chloroprop-2-ynoxy |
| 3-methyl-3-buten-1-yl | 4,4-difluorobut-2-ynoxy |
| 4-methyl-3-penten-1-yl | 5,5,5-trifluoropent-2-ynoxy |
| 3-penten-1-yl | 5,5,5-trifluoropent-3-ynoxy |
| 3-butyn-1-yl | cyclobutylmethoxy |
| 4-methyl-2-pentyn-1-yl | cyclohexoxy |
| 3-pentyn-1-yl | cyclopentoxy |
| 2-propyn-1-yl | 2-cyclopropylethoxy |
| 5-hexyn-1-yl | cyclopropylmethoxy |
| 4-pentyn-1-yl | (2-bromo-2-chloro-cyclopropyl)methoxy |
| 3-bromopropyl | (2,2-dibromocyclopropyl)methoxy |
| 3-chlorobutyl | (2,2-dichloro-1-methyl-cyclopropyl)methoxy |
| 3-chloropropyl | (3,3-difluorocyclobutyl)methoxy |
| 4,4-difluorobutyl | 2-(2,2-difluorocyclopropyl)ethoxy |
| 2,2-difluoroethyl | (2,2-difluorocyclopropyl)methoxy |
| 3,3-difluoropropyl | 2-chloroethoxymethyl |
| 3,3,4,4,4-pentafluorobutyl | 2,3-dichloro-5-methoxy-pentyl |
| 2,2,3,3,3-pentafluoropropyl | 3,3-difluoro-5-methoxy-pentyl |
| 3,3,4,4-tetrafluorobutyl | 2-isopropoxyethyl |
| 2,2,3,3-tetrafluoropropyl | 2-methoxyethyl |
| 3,3,3-trichloropropyl | 5-methoxypentyl |
| 4,4,4-trifluorobutyl | 2-methoxypropyl |

-continued

| R | R |
|---|---|
| 2,2,2-trifluoroethyl | 1,1,2,2-tetrafluoroethoxymethyl |
| 6,6,6-trifluorohexyl | 2,2,2-trifluoroethoxymethyl |
| 4,4,4-trifluoro-2-methyl-butyl | 2-(trifluoromethoxy)ethyl |
| 3,3,3-trifluoropropyl | 2-isopropoxyethoxy |
| 4-bromo-3-buten-1-yl | 4-methoxybutoxy |
| 2-chloroallyl | 2-methoxyethoxy |
| 3-chloroallyl | 2-methoxypropoxy |
| 3-chloro-3-buten-1-yl | 4-cyanobutyl |
| 4-chloro-3-buten-1-yl | 3-cyano-1,2-dimethyl-propyl |
| 5,5-difluoro-3-penten-1-yl | 2-cyanoethyl |
| 4,4,4-trifluoro-2-buten-1-yl | 3-cyano-2-methyl-propyl |
| 5,5,5-trifluoro-3-methyl-2-penten-1-yl | cyanomethyl |
| 5,5,5-trifluoro-3-penten-1-yl | 5-cyanopentyl |
| 4-bromo-3-butyn-1-yl | 3-cyanopropyl |
| 3-butyn-1-yl | 4-cyanobutoxy |
| 4-chloro-3-butyn-1-yl | 3-cyano-1,2-dimethyl-propoxy |
| 3-chloro-2-propyn-1-yl | 2-cyanoethoxy |
| 4,4-difluoro-2-butyn-1-yl | cyanomethoxy |
| 5,5,5-trifluoro-1-methyl-2-pentyn-1-yl | 3-cyano-2-methyl-propoxy |
| 5,5,5-trifluoro-2-pentyn-1-yl | 5-cyanopentoxy |
| 5,5,5-trifluoro-3-pentyn-1-yl | 3-cyanopropoxy |
| 2-cyclobutylethyl | 2-(cyanomethoxy)ethyl |
| cyclohexyl | 3-(cyanomethoxy)-2-methyl-propyl |
| cyclopentylmethyl | cyanomethoxymethyl |
| 2-cyclopropylethyl | 1,2-dimethyl-3-nitro-propyl |
| 3-cyclopropylpropyl | 4-hydroxybutyl |
| (2,2-dimethylcyclopropyl)methyl | 3-hydroxy-1,2-dimethyl-propyl |
| (1-methylcyclopropyl)methyl | 2-hydroxyethyl |
| (2-methylcyclopentyl)methyl | 3-hydroxy-2-methyl-propyl |
| (2-bromo-2-chloro-cyclopropyl)methyl | hydroxymethyl |
| (2,2-dibromocyclopropyl)methyl | 5-hydroxypentyl |
| 2-(2,2-dichloro-1-methyl-cyclopropyl)ethyl | 3-hydroxypropyl |
| (2,2-dichloro-1-methyl-cyclopropyl)methyl | 2-methyl-3-nitro-propyl |
| 2-(3,3-difluorocyclobutyl)ethyl | 4-nitrobutyl |
| 2-(2,2-difluorocyclopropyl)ethyl | 2-nitroethyl |
| (2,2-difluorocyclopropyl)methyl | nitromethyl |
| butyl(methyl)amino | 5-nitropentyl |
| dimethylamino | 3-nitropropyl |
| ethyl(propyl)amino | butylthio |
| isopropyl(methyl)amino | tert-butylthio |
| isopropyl(propyl)amino | 1,3-dimethylbutylthio |
| methyl(propyl)amino | 3,3-dimethylbutylthio |
| 2-chloroethyl(2,2,2-trifluoroethyl)amino | ethylthio |
| 3-chloropropyl(methyl)amino | isopentylthio |
| methyl(2,2,2-trifluoroethyl)amino | methylthio |
| methyl(3,3,3-trifluoropropyl)amino | pentylthio |
| butylamino | propylthio |
| 3-chloropropylamino | 3-bromopropylthio |
| isopentylamino | 3-chlorobutylthio |
| propylamino | 3-chloropropylthio |
| 3,3,3-trifluoropropylamino | 2,2-difluoroethylthio |
| butoxy | 3,3,3-trichloropropylthio |
| tert-butoxy | 4,4,4-trifluorobutylthio |
| 1,3-dimethylbutoxy | 2,2,2-trifluoroethylthio |
| 3,3-dimethylbutoxy | 6,6,6-trifluorohexylthio |
| ethoxy | 3,3,3-trifluoropropylthio |
| hexyl | cyclobutylmethylthio |
| isopentyloxy | cyclohexylthio |
| methoxy | cyclopentylthio |
| propoxy | 2-cyclopropylethylthio |
| allyloxy | cyclopropylmethylthio |
| 3-butenoxy | 2-chloroethylthiomethyl |
| 3-methyl-2-butenoxy | 2,3-dichloro-5-methylthio-pentyl |
| 3-methyl-3-butenoxy | 3,3-difluoro-5-methylthio-pentyl |
| 4-methyl-3-pentenoxy | 2-isopropylthioethyl |
| 4-bromo-3-butenoxy | 2-methylthioethyl |
| 2-chloroallyloxy | 5-methylthiopentyl |
| 3-chloroallyloxy | 2-methylthiopropyl |
| 3-chloro-3-butenoxy | 1,1,2,2-tetrafluoroethylthiomethyl |
| 4-chloro-3-butenoxy | 2,2,2-trifluoroethylthiomethyl |
| 5,5-difluoro-3-pentenoxy | 2-(trifluoromethylthio)ethyl |
| 4,4,4-trifluoro-2-butenoxy | bis(2-chloroethyl)aminooxy |
| 5,5,5-trifluoro-3-methyl-2-pentenoxy | cyanomethoxy(methyl)amino |
| 5,5,5-trifluoro-3-pentenoxy | diethylamino(methyl)amino |
| 3-butynoxy | ethoxy(methyl)amino |
| 5-hexynoxy | ethoxy(2,2,2-trifluoroethyl)amino |
| 4-methyl-2-pentynoxy | ethylamino(methyl)amino |

-continued

| R | R |
|---|---|
| 3-pentynoxy | ethylamino(2,2,2-trifluoroethyl)amino |
| 4-pentynoxy | ethyl(methyl)amino-(2,2,2-trifluoroethyl)amino |
| 2-propynoxy | ethyl(3,3,3-trifluoropropyl)amino-methyl-amino |
| 3-bromopropoxy | isobutyl(methyl)aminooxy |
| 3-chlorobutoxy | 2-methoxyethoxy(methyl)amino |
| 3-chloropropoxy | methyl(propyl)aminooxy |
| 4,4-difluorobutoxy | methyl(2,2,2-trifluoroethoxy)amino |
| 2,2-difluoroethoxy | methyl(2,2,2-trifluoroethyl)aminooxy |
| 3,3-difluoropropoxy | methyl(3,3,3-trifluoropropoxy)amino |
|  | methyl(3,3,3-trifluoropropylamino)amino |

TABLE 1-1

1-1

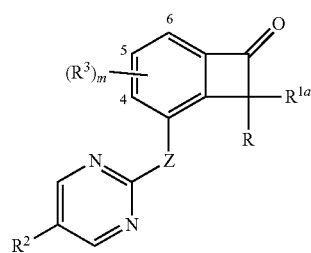

| Table | $R^{1a}$ | $R^2$ | $(R^3)_m$ | Z |
|---|---|---|---|---|
| 1-2 | F | F | H | O |
| 1-3 | OH | F | H | O |
| 1-4 | CN | F | H | O |
| 1-5 | H | Cl | H | O |
| 1-6 | F | Cl | H | O |
| 1-7 | OH | Cl | H | O |
| 1-8 | CN | Cl | H | O |
| 1-9 | H | Br | H | O |
| 1-10 | F | Br | H | O |
| 1-11 | OH | Br | H | O |
| 1-12 | CN | Br | H | O |
| 1-13 | H | $CF_3$ | H | O |
| 1-14 | F | $CF_3$ | H | O |
| 1-15 | OH | $CF_3$ | H | O |
| 1-16 | CN | $CF_3$ | H | O |
| 1-17 | H | $OCH_3$ | H | O |
| 1-18 | F | $OCH_3$ | H | O |
| 1-19 | OH | $OCH_3$ | H | O |
| 1-20 | CN | $OCH_3$ | H | O |
| 1-21 | H | $CH_3$ | H | O |
| 1-22 | F | $CH_3$ | H | O |
| 1-23 | OH | $CH_3$ | H | O |
| 1-24 | CN | $CH_3$ | H | O |
| 1-25 | H | Cl | 4-F | O |
| 1-26 | H | Cl | 5-F | O |
| 1-27 | H | Cl | 6-F | O |
| 1-28 | H | Cl | H | S |

$R^{1a}$=H, $R^2$=F, $(R^3)_m$=H and Z=O, and each value for R is described in Exhibit 2.

The present disclosure also includes Tables 1-2 through 1-28. Each Table is constructed in the same manner as Table 1-1 above, except that the row heading in Table 1-1 (i.e. "$R^{1a}$=H, $R^2$=F, $(R^3)_m$=H and Z=O") is replaced with the respective row heading shown below. For example, the first entry in Table 1-2 is a compound of Formula 1-1 wherein $R^{1a}$ is F, $R^2$ is F, $(R^3)_m$ is H and Z is O and R is butyl. Tables 1-3 through 1-28 are constructed similarly.

TABLE 2-1

1-2

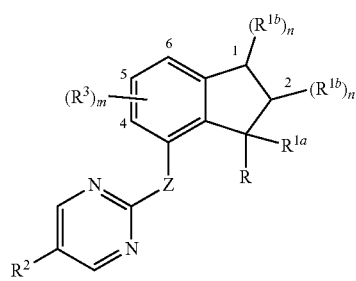

| Table | $R^{1a}$ | $(R^{1b})_n$ | $R^2$ | $(R^3)_m$ | Z |
|---|---|---|---|---|---|
| 2-2 | F | 1-H, 2-H | F | H | O |
| 2-3 | OH | 1-H, 2-H | F | H | O |
| 2-4 | CN | 1-H, 2-H | F | H | O |
| 2-5 | H | 1-H, 2-H | Cl | H | O |
| 2-6 | F | 1-H, 2-H | Cl | H | O |
| 2-7 | OH | 1-H, 2-H | Cl | H | O |
| 2-8 | CN | 1-H, 2-H | Cl | H | O |
| 2-9 | H | 1-H, 2-H | Br | H | O |
| 2-10 | F | 1-H, 2-H | Br | H | O |
| 2-11 | OH | 1-H, 2-H | Br | H | O |
| 2-12 | CN | 1-H, 2-H | Br | H | O |
| 2-13 | H | 1-H, 2-H | $CF_3$ | H | O |
| 2-14 | F | 1-H, 2-H | $CF_3$ | H | O |
| 2-15 | OH | 1-H, 2-H | $CF_3$ | H | O |
| 2-16 | CN | 1-H, 2-H | $CF_3$ | H | O |
| 2-17 | H | 1-H, 2-H | $OCH_3$ | H | O |
| 2-18 | F | 1-H, 2-H | $OCH_3$ | H | O |
| 2-19 | OH | 1-H, 2-H | $OCH_3$ | H | O |
| 2-20 | CN | 1-H, 2-H | $OCH_3$ | H | O |
| 2-21 | H | 1-H, 2-H | $CH_3$ | H | O |
| 2-22 | F | 1-H, 2-H | $CH_3$ | H | O |
| 2-23 | OH | 1-H, 2-H | $CH_3$ | H | O |
| 2-24 | CN | 1-H, 2-H | $CH_3$ | H | O |
| 2-25 | H | 1-H, 2-H | F | 4-F | O |
| 2-26 | F | 1-H, 2-H | F | 4-F | O |
| 2-27 | OH | 1-H, 2-H | F | 4-F | O |
| 2-28 | CN | 1-H, 2-H | F | 4-F | O |
| 2-29 | H | 1-H, 2-H | Cl | 4-F | O |
| 2-30 | F | 1-H, 2-H | Cl | 4-F | O |
| 2-31 | OH | 1-H, 2-H | Cl | 4-F | O |
| 2-32 | CN | 1-H, 2-H | Cl | 4-F | O |
| 2-33 | H | 1-H, 2-H | Br | 4-F | O |
| 2-34 | F | 1-H, 2-H | Br | 4-F | O |
| 2-35 | OH | 1-H, 2-H | Br | 4-F | O |
| 2-36 | CN | 1-H, 2-H | Br | 4-F | O |
| 2-37 | H | 1-H, 2-H | $CF_3$ | 4-F | O |
| 2-38 | F | 1-H, 2-H | $CF_3$ | 4-F | O |
| 2-39 | OH | 1-H, 2-H | $CF_3$ | 4-F | O |
| 2-40 | CN | 1-H, 2-H | $CF_3$ | 4-F | O |
| 2-41 | H | 1-H, 2-H | $OCH_3$ | 4-F | O |
| 2-42 | F | 1-H, 2-H | $OCH_3$ | 4-F | O |
| 2-43 | OH | 1-H, 2-H | $OCH_3$ | 4-F | O |
| 2-44 | CN | 1-H, 2-H | $OCH_3$ | 4-F | O |

TABLE 2-1-continued

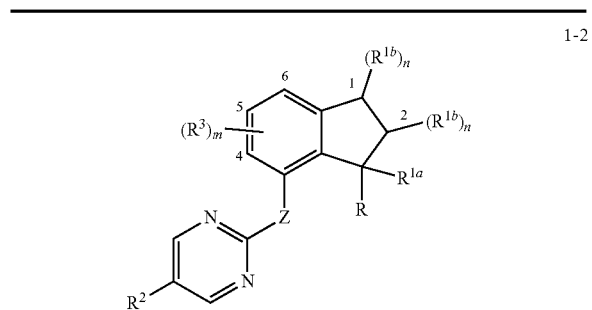

| Table | $R^{1a}$ | $(R^{1b})_n$ | $R^2$ | $(R^3)_m$ | Z |
|---|---|---|---|---|---|
| 2-45 | H | 1-H, 2-H | $CH_3$ | 4-F | O |
| 2-46 | F | 1-H, 2-H | $CH_3$ | 4-F | O |
| 2-47 | OH | 1-H, 2-H | $CH_3$ | 4-F | O |
| 2-48 | CN | 1-H, 2-H | $CH_3$ | 4-F | O |
| 2-49 | H | 1-H, 2-H | F | 5-F | O |
| 2-50 | F | 1-H, 2-H | F | 5-F | O |
| 2-51 | OH | 1-H, 2-H | F | 5-F | O |
| 2-52 | CN | 1-H, 2-H | F | 5-F | O |
| 2-53 | H | 1-H, 2-H | Cl | 5-F | O |
| 2-54 | F | 1-H, 2-H | Cl | 5-F | O |
| 2-55 | OH | 1-H, 2-H | Cl | 5-F | O |
| 2-56 | CN | 1-H, 2-H | Cl | 5-F | O |
| 2-57 | H | 1-H, 2-H | Br | 5-F | O |
| 2-58 | F | 1-H, 2-H | Br | 5-F | O |
| 2-59 | OH | 1-H, 2-H | Br | 5-F | O |
| 2-60 | CN | 1-H, 2-H | Br | 5-F | O |
| 2-61 | H | 1-H, 2-H | $CF_3$ | 5-F | O |
| 2-62 | F | 1-H, 2-H | $CF_3$ | 5-F | O |
| 2-63 | OH | 1-H, 2-H | $CF_3$ | 5-F | O |
| 2-64 | CN | 1-H, 2-H | $CF_3$ | 5-F | O |
| 2-65 | H | 1-H, 2-H | $OCH_3$ | 5-F | O |
| 2-66 | F | 1-H, 2-H | $OCH_3$ | 5-F | O |
| 2-67 | OH | 1-H, 2-H | $OCH_3$ | 5-F | O |
| 2-68 | CN | 1-H, 2-H | $OCH_3$ | 5-F | O |
| 2-69 | H | 1-H, 2-H | $CH_3$ | 5-F | O |
| 2-70 | F | 1-H, 2-H | $CH_3$ | 5-F | O |
| 2-71 | OH | 1-H, 2-H | $CH_3$ | 5-F | O |
| 2-72 | CN | 1-H, 2-H | $CH_3$ | 5-F | O |
| 2-73 | H | 1-H, 2-H | F | 6-F | O |
| 2-74 | F | 1-H, 2-H | F | 6-F | O |
| 2-75 | OH | 1-H, 2-H | F | 6-F | O |
| 2-76 | CN | 1-H, 2-H | F | 6-F | O |
| 2-77 | H | 1-H, 2-H | Cl | 6-F | O |
| 2-78 | F | 1-H, 2-H | Cl | 6-F | O |
| 2-79 | OH | 1-H, 2-H | Cl | 6-F | O |
| 2-80 | CN | 1-H, 2-H | Cl | 6-F | O |
| 2-81 | H | 1-H, 2-H | Br | 6-F | O |
| 2-82 | F | 1-H, 2-H | Br | 6-F | O |
| 2-83 | OH | 1-H, 2-H | Br | 6-F | O |
| 2-84 | CN | 1-H, 2-H | Br | 6-F | O |
| 2-85 | H | 1-H, 2-H | $CF_3$ | 6-F | O |
| 2-86 | F | 1-H, 2-H | $CF_3$ | 6-F | O |
| 2-87 | OH | 1-H, 2-H | $CF_3$ | 6-F | O |
| 2-88 | CN | 1-H, 2-H | $CF_3$ | 6-F | O |
| 2-89 | H | 1-H, 2-H | $OCH_3$ | 6-F | O |
| 2-90 | F | 1-H, 2-H | $OCH_3$ | 6-F | O |
| 2-91 | OH | 1-H, 2-H | $OCH_3$ | 6-F | O |
| 2-92 | CN | 1-H, 2-H | $OCH_3$ | 6-F | O |
| 2-93 | H | 1-H, 2-H | $CH_3$ | 6-F | O |
| 2-94 | F | 1-H, 2-H | $CH_3$ | 6-F | O |
| 2-95 | OH | 1-H, 2-H | $CH_3$ | 6-F | O |
| 2-96 | CN | 1-H, 2-H | $CH_3$ | 6-F | O |
| 2-97 | H | 1-H, 2-H | Cl | H | S |
| 2-98 | F | 1-H, 2-H | Cl | H | S |
| 2-99 | OH | 1-H, 2-H | Cl | H | S |
| 2-100 | CN | 1-H, 2-H | Cl | H | S |
| 2-101 | H | 1-OH, 2-H | F | H | O |
| 2-102 | H | 1-OH, 2-H | Cl | H | O |
| 2-103 | H | 1-OH, 2-H | Br | H | O |
| 2-104 | H | 1-OH, 2-H | $CF_3$ | H | O |
| 2-105 | H | 1-OH, 2-H | $OCH_3$ | H | O |

TABLE 2-1-continued

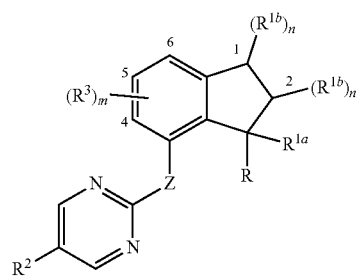

| Table | $R^{1a}$ | $(R^{1b})_n$ | $R^2$ | $(R^3)_m$ | Z |
|---|---|---|---|---|---|
| 2-106 | H | 1-OH, 2-H | $CH_3$ | H | O |
| 2-107 | H | 1-OH, 2-H | Cl | H | O |
| 2-108 | H | 1-CN, 2-H | F | H | O |
| 2-109 | H | 1-CN, 2-H | Cl | H | O |
| 2-110 | H | 1-CN, 2-H | Br | H | O |
| 2-111 | H | 1-CN, 2-H | $CF_3$ | H | O |
| 2-112 | H | 1-CN, 2-H | $OCH_3$ | H | O |
| 2-113 | H | 1-CN, 2-H | $CH_3$ | H | O |
| 2-114 | H | 1-H, 2-OH | F | H | O |
| 2-115 | H | 1-H, 2-OH | Cl | H | O |
| 2-116 | H | 1-H, 2-OH | Br | H | O |
| 2-117 | H | 1-H, 2-OH | $CF_3$ | H | O |
| 2-118 | H | 1-H, 2-OH | $OCH_3$ | H | O |
| 2-119 | H | 1-H, 2-OH | $CH_3$ | H | O |
| 2-120 | H | 1-H, 2-OH | Cl | H | O |
| 2-121 | H | 1-H, 2-CN | F | H | O |
| 2-122 | H | 1-H, 2-CN | Cl | H | O |
| 2-123 | H | 1-H, 2-CN | Br | H | O |
| 2-124 | H | 1-H, 2-CN | $CF_3$ | H | O |
| 2-125 | H | 1-H, 2-CN | $OCH_3$ | H | O |
| 2-126 | H | 1-H, 2-CN | $CH_3$ | H | O |
| 2-127 | H | 1-OH, 2-H | F | 4-F | O |
| 2-128 | H | 1-OH, 2-H | Cl | 4-F | O |
| 2-129 | H | 1-OH, 2-H | Br | 4-F | O |
| 2-130 | H | 1-OH, 2-H | $CF_3$ | 4-F | O |
| 2-131 | H | 1-OH, 2-H | $OCH_3$ | 4-F | O |
| 2-132 | H | 1-OH, 2-H | $CH_3$ | 4-F | O |
| 2-133 | H | 1-OH, 2-H | Cl | 4-F | O |
| 2-134 | H | 1-CN, 2-H | F | 4-F | O |
| 2-135 | H | 1-CN, 2-H | Cl | 4-F | O |
| 2-136 | H | 1-CN, 2-H | Br | 4-F | O |
| 2-137 | H | 1-CN, 2-H | $CF_3$ | 4-F | O |
| 2-138 | H | 1-CN, 2-H | $OCH_3$ | 4-F | O |
| 2-139 | H | 1-CN, 2-H | $CH_3$ | 4-F | O |
| 2-140 | H | 1-H, 2-OH | F | 4-F | O |
| 2-141 | H | 1-H, 2-OH | Cl | 4-F | O |
| 2-142 | H | 1-H, 2-OH | Br | 4-F | O |
| 2-143 | H | 1-H, 2-OH | $CF_3$ | 4-F | O |
| 2-144 | H | 1-H, 2-OH | $OCH_3$ | 4-F | O |
| 2-145 | H | 1-H, 2-OH | $CH_3$ | 4-F | O |
| 2-146 | H | 1-H, 2-OH | Cl | 4-F | O |
| 2-147 | H | 1-H, 2-CN | F | 4-F | O |
| 2-148 | H | 1-H, 2-CN | Cl | 4-F | O |
| 2-149 | H | 1-H, 2-CN | Br | 4-F | O |
| 2-150 | H | 1-H, 2-CN | $CF_3$ | 4-F | O |
| 2-151 | H | 1-H, 2-CN | $OCH_3$ | 4-F | O |
| 2-152 | H | 1-H, 2-CN | $CH_3$ | 4-F | O |
| 2-153 | H | 1-OH, 2-H | F | 5-F | O |
| 2-154 | H | 1-OH, 2-H | Cl | 5-F | O |
| 2-155 | H | 1-OH, 2-H | Br | 5-F | O |
| 2-156 | H | 1-OH, 2-H | $CF_3$ | 5-F | O |
| 2-157 | H | 1-OH, 2-H | $OCH_3$ | 5-F | O |
| 2-158 | H | 1-OH, 2-H | $CH_3$ | 5-F | O |
| 2-159 | H | 1-OH, 2-H | Cl | 5-F | O |
| 2-160 | H | 1-CN, 2-H | F | 5-F | O |
| 2-161 | H | 1-CN, 2-H | Cl | 5-F | O |
| 2-162 | H | 1-CN, 2-H | Br | 5-F | O |
| 2-163 | H | 1-CN, 2-H | $CF_3$ | 5-F | O |
| 2-164 | H | 1-CN, 2-H | $OCH_3$ | 5-F | O |
| 2-165 | H | 1-CN, 2-H | $CH_3$ | 5-F | O |
| 2-166 | H | 1-H, 2-OH | F | 5-F | O |

TABLE 2-1-continued 1-2

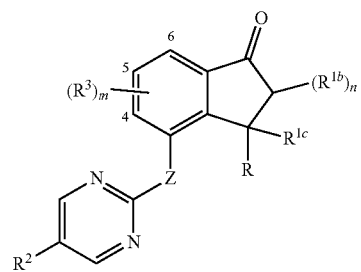

Header Row

| Table | $R^{1a}$ | $(R^{1b})_n$ | $R^2$ | $(R^3)_m$ | Z |
|---|---|---|---|---|---|
| 2-167 | H | 1-H, 2-OH | Cl | 5-F | O |
| 2-168 | H | 1-H, 2-OH | Br | 5-F | O |
| 2-169 | H | 1-H, 2-OH | $CF_3$ | 5-F | O |
| 2-170 | H | 1-H, 2-OH | $OCH_3$ | 5-F | O |
| 2-171 | H | 1-H, 2-OH | $CH_3$ | 5-F | O |
| 2-172 | H | 1-H, 2-OH | Cl | 5-F | O |
| 2-173 | H | 1-H, 2-CN | F | 5-F | O |
| 2-174 | H | 1-H, 2-CN | Cl | 5-F | O |
| 2-175 | H | 1-H, 2-CN | Br | 5-F | O |
| 2-176 | H | 1-H, 2-CN | $CF_3$ | 5-F | O |
| 2-177 | H | 1-H, 2-CN | $OCH_3$ | 5-F | O |
| 2-178 | H | 1-H, 2-CN | $CH_3$ | 5-F | O |
| 2-179 | H | 1-OH, 2-H | F | 6-F | O |
| 2-180 | H | 1-OH, 2-H | Cl | 6-F | O |
| 2-181 | H | 1-OH, 2-H | Br | 6-F | O |
| 2-182 | H | 1-OH, 2-H | $CF_3$ | 6-F | O |
| 2-183 | H | 1-OH, 2-H | $OCH_3$ | 6-F | O |
| 2-184 | H | 1-OH, 2-H | $CH_3$ | 6-F | O |
| 2-185 | H | 1-OH, 2-H | Cl | 6-F | O |
| 2-186 | H | 1-CN, 2-H | F | 6-F | O |
| 2-187 | H | 1-CN, 2-H | Cl | 6-F | O |
| 2-188 | H | 1-CN, 2-H | Br | 6-F | O |
| 2-189 | H | 1-CN, 2-H | $CF_3$ | 6-F | O |
| 2-190 | H | 1-CN, 2-H | $OCH_3$ | 6-F | O |
| 2-191 | H | 1-CN, 2-H | $CH_3$ | 6-F | O |
| 2-192 | H | 1-H, 2-OH | F | 6-F | O |
| 2-193 | H | 1-H, 2-OH | Cl | 6-F | O |
| 2-194 | H | 1-H, 2-OH | Br | 6-F | O |
| 2-195 | H | 1-H, 2-OH | $CF_3$ | 6-F | O |
| 2-196 | H | 1-H, 2-OH | $OCH_3$ | 6-F | O |
| 2-197 | H | 1-H, 2-OH | $CH_3$ | 6-F | O |
| 2-198 | H | 1-H, 2-OH | Cl | 6-F | O |
| 2-199 | H | 1-H, 2-CN | F | 6-F | O |
| 2-200 | H | 1-H, 2-CN | Cl | 6-F | O |
| 2-201 | H | 1-H, 2-CN | Br | 6-F | O |
| 2-202 | H | 1-H, 2-CN | $CF_3$ | 6-F | O |
| 2-203 | H | 1-H, 2-CN | $OCH_3$ | 6-F | O |
| 2-204 | H | 1-H, 2-CN | $CH_3$ | 6-F | O |
| 2-205 | H | 1-OH, 2-H | Cl | H | S |
| 2-206 | H | 1-CN, 2-H | Cl | H | S |
| 2-207 | H | 1-H, 2-OH | Cl | H | S |
| 2-208 | H | 1-H, 2-CN | Cl | H | S |

$R^{1a}$=H, $(R^{1b})_n$=1-H, 2-H, $R^2$=F, $(R^3)_m$=H and Z=O, and each value for R is described in Exhibit 2.

The present disclosure also includes Tables 2-2 through 2-208. Each Table is constructed in the same manner as Table 2-1 above, except that the row heading in Table 2-1 (i.e. "$R^{1a}$=H, $(R^{1b})_n$=1-H, 2-H, $R^2$=F, $(R^3)_m$=H and Z=O") is replaced with the respective row heading shown below. For example, the first entry in Table 2-2 is a compound of Formula 1-2 wherein $R^{1a}$ is F, $(R^{1b})_n$=1-H, 2-H, $R^2$ is F, $(R^3)_m$ is H and Z is O and R is butyl. Tables 2-3 through 2-208 are constructed similarly.

TABLE 3-1

1-3

Header Row

| Table | $R^{1c}$ | $(R^{1b})_n$ | $R^2$ | $(R^3)_m$ | Z |
|---|---|---|---|---|---|
| 3-2 | F | H | F | H | O |
| 3-3 | OH | H | F | H | O |
| 3-4 | CN | H | F | H | O |
| 3-5 | H | H | Cl | H | O |
| 3-6 | F | H | Cl | H | O |
| 3-7 | OH | H | Cl | H | O |
| 3-8 | CN | H | Cl | H | O |
| 3-9 | H | H | Br | H | O |
| 3-10 | F | H | Br | H | O |
| 3-11 | OH | H | Br | H | O |
| 3-12 | CN | H | Br | H | O |
| 3-13 | H | H | $CF_3$ | H | O |
| 3-14 | F | H | $CF_3$ | H | O |
| 3-15 | OH | H | $CF_3$ | H | O |
| 3-16 | CN | H | $CF_3$ | H | O |
| 3-17 | H | H | $OCH_3$ | H | O |
| 3-18 | F | H | $OCH_3$ | H | O |
| 3-19 | OH | H | $OCH_3$ | H | O |
| 3-20 | CN | H | $OCH_3$ | H | O |
| 3-21 | H | H | $CH_3$ | H | O |
| 3-22 | F | H | $CH_3$ | H | O |
| 3-23 | OH | H | $CH_3$ | H | O |
| 3-24 | CN | H | $CH_3$ | H | O |
| 3-25 | H | H | F | 4-F | O |
| 3-26 | F | H | F | 4-F | O |
| 3-27 | OH | H | F | 4-F | O |
| 3-28 | CN | H | F | 4-F | O |
| 3-29 | H | H | Cl | 4-F | O |
| 3-30 | F | H | Cl | 4-F | O |
| 3-31 | OH | H | Cl | 4-F | O |
| 3-32 | CN | H | Cl | 4-F | O |
| 3-33 | H | H | Br | 4-F | O |
| 3-34 | F | H | Br | 4-F | O |
| 3-35 | OH | H | Br | 4-F | O |
| 3-36 | CN | H | Br | 4-F | O |
| 3-37 | H | H | $CF_3$ | 4-F | O |
| 3-38 | F | H | $CF_3$ | 4-F | O |
| 3-39 | OH | H | $CF_3$ | 4-F | O |
| 3-40 | CN | H | $CF_3$ | 4-F | O |
| 3-41 | H | H | $OCH_3$ | 4-F | O |
| 3-42 | F | H | $OCH_3$ | 4-F | O |
| 3-43 | OH | H | $OCH_3$ | 4-F | O |
| 3-44 | CN | H | $OCH_3$ | 4-F | O |
| 3-45 | H | H | $CH_3$ | 4-F | O |
| 3-46 | F | H | $CH_3$ | 4-F | O |
| 3-47 | OH | H | $CH_3$ | 4-F | O |
| 3-48 | CN | H | $CH_3$ | 4-F | O |
| 3-49 | H | H | F | 5-F | O |
| 3-50 | F | H | F | 5-F | O |
| 3-51 | OH | H | F | 5-F | O |
| 3-52 | CN | H | F | 5-F | O |
| 3-53 | H | H | Cl | 5-F | O |
| 3-54 | F | H | Cl | 5-F | O |
| 3-55 | OH | H | Cl | 5-F | O |
| 3-56 | CN | H | Cl | 5-F | O |
| 3-57 | H | H | Br | 5-F | O |
| 3-58 | F | H | Br | 5-F | O |
| 3-59 | OH | H | Br | 5-F | O |
| 3-60 | CN | H | Br | 5-F | O |
| 3-61 | H | H | $CF_3$ | 5-F | O |
| 3-62 | F | H | $CF_3$ | 5-F | O |

TABLE 3-1-continued 1-3

| Table | $R^{1c}$ | $(R^{1b})_n$ | $R^2$ | $(R^3)_m$ | Z |
|---|---|---|---|---|---|
| 3-63 | OH | H | CF$_3$ | 5-F | O |
| 3-64 | CN | H | CF$_3$ | 5-F | O |
| 3-65 | H | H | OCH$_3$ | 5-F | O |
| 3-66 | F | H | OCH$_3$ | 5-F | O |
| 3-67 | OH | H | OCH$_3$ | 5-F | O |
| 3-68 | CN | H | OCH$_3$ | 5-F | O |
| 3-69 | H | H | CH$_3$ | 5-F | O |
| 3-70 | F | H | CH$_3$ | 5-F | O |
| 3-71 | OH | H | CH$_3$ | 5-F | O |
| 3-72 | CN | H | CH$_3$ | 5-F | O |
| 3-73 | H | H | F | 6-F | O |
| 3-74 | F | H | F | 6-F | O |
| 3-75 | OH | H | F | 6-F | O |
| 3-76 | CN | H | F | 6-F | O |
| 3-77 | H | H | Cl | 6-F | O |
| 3-78 | F | H | Cl | 6-F | O |
| 3-79 | OH | H | Cl | 6-F | O |
| 3-80 | CN | H | Cl | 6-F | O |
| 3-81 | H | H | Br | 6-F | O |
| 3-82 | F | H | Br | 6-F | O |
| 3-83 | OH | H | Br | 6-F | O |
| 3-84 | CN | H | Br | 6-F | O |
| 3-85 | H | H | CF$_3$ | 6-F | O |
| 3-86 | F | H | CF$_3$ | 6-F | O |
| 3-87 | OH | H | CF$_3$ | 6-F | O |
| 3-88 | CN | H | CF$_3$ | 6-F | O |
| 3-89 | H | H | OCH$_3$ | 6-F | O |
| 3-90 | F | H | OCH$_3$ | 6-F | O |
| 3-91 | OH | H | OCH$_3$ | 6-F | O |
| 3-92 | CN | H | OCH$_3$ | 6-F | O |
| 3-93 | H | H | CH$_3$ | 6-F | O |
| 3-94 | F | H | CH$_3$ | 6-F | O |
| 3-95 | OH | H | CH$_3$ | 6-F | O |
| 3-96 | CN | H | CH$_3$ | 6-F | O |
| 3-97 | H | H | Cl | H | O |
| 3-98 | F | H | Cl | H | O |
| 3-99 | OH | H | Cl | H | O |
| 3-100 | CN | H | Cl | H | O |
| 3-101 | H | OH | F | H | O |
| 3-102 | H | CN | F | H | O |
| 3-103 | H | OH | Cl | H | O |
| 3-104 | H | CN | Cl | H | O |
| 3-105 | H | OH | Br | H | O |
| 3-106 | H | CN | Br | H | O |
| 3-107 | H | OH | CF$_3$ | H | O |
| 3-108 | H | CN | CF$_3$ | H | O |
| 3-109 | H | OH | OCH$_3$ | H | O |
| 3-110 | H | CN | OCH$_3$ | H | O |
| 3-111 | H | OH | CH$_3$ | H | O |
| 3-112 | H | CN | CH$_3$ | H | O |
| 3-113 | H | OH | F | 4-F | O |
| 3-114 | H | CN | F | 4-F | O |
| 3-115 | H | OH | Cl | 4-F | O |
| 3-116 | H | CN | Cl | 4-F | O |
| 3-117 | H | OH | Br | 4-F | O |
| 3-118 | H | CN | Br | 4-F | O |
| 3-119 | H | OH | CF$_3$ | 4-F | O |
| 3-120 | H | CN | CF$_3$ | 4-F | O |
| 3-121 | H | OH | OCH$_3$ | 4-F | O |
| 3-122 | H | CN | OCH$_3$ | 4-F | O |
| 3-123 | H | OH | CH$_3$ | 4-F | O |
| 3-124 | H | CN | CH$_3$ | 4-F | O |
| 3-125 | H | OH | F | 5-F | O |
| 3-126 | H | CN | F | 5-F | O |
| 3-127 | H | OH | Cl | 5-F | O |
| 3-128 | H | CN | Cl | 5-F | O |
| 3-129 | H | OH | Br | 5-F | O |
| 3-130 | H | CN | Br | 5-F | O |
| 3-131 | H | OH | CF$_3$ | 5-F | O |
| 3-132 | H | CN | CF$_3$ | 5-F | O |
| 3-133 | H | OH | OCH$_3$ | 5-F | O |
| 3-134 | H | CN | OCH$_3$ | 5-F | O |
| 3-135 | H | OH | CH$_3$ | 5-F | O |
| 3-136 | H | CN | CH$_3$ | 5-F | O |
| 3-137 | H | OH | F | 6-F | O |
| 3-138 | H | CN | F | 6-F | O |
| 3-139 | H | OH | Cl | 6-F | O |
| 3-140 | H | CN | Cl | 6-F | O |
| 3-141 | H | OH | Br | 6-F | O |
| 3-142 | H | CN | Br | 6-F | O |
| 3-143 | H | OH | CF$_3$ | 6-F | O |
| 3-144 | H | CN | CF$_3$ | 6-F | O |
| 3-145 | H | OH | OCH$_3$ | 6-F | O |
| 3-146 | H | CN | OCH$_3$ | 6-F | O |
| 3-147 | H | OH | CH$_3$ | 6-F | O |
| 3-148 | H | CN | CH$_3$ | 6-F | O |

$R^{1c}$=H, $(R^{1b})_n$=H, $R^2$=F, $(R^3)_m$=H and Z=O, and each value for R is described in Exhibit 2.

The present disclosure also includes Tables 3-2 through 3-148. Each Table is constructed in the same manner as Table 3-1 above, except that the row heading in Table 3-1 (i.e. "$R^{1c}$=H, $(R^{1b})_n$=H, $R^2$=F, $(R^3)_m$=H and Z=O") is replaced with the respective row heading shown below. For example, the first entry in Table 3-2 is a compound of Formula 1-3 wherein $R^{1c}$ is F, $(R^{1b})_n$=H, $R^2$ is F, $(R^3)_m$ is H and Z is O and R is butyl. Tables 3-3 through 3-148 are constructed similarly.

TABLE 4-1

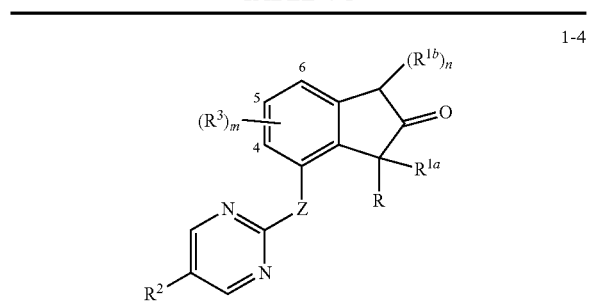

1-4

| Table | $R^{1a}$ | $(R^{1b})_n$ | $R^2$ | $(R^3)_m$ | Z |
|---|---|---|---|---|---|
| 4-2 | F | H | F | H | O |
| 4-3 | OH | H | F | H | O |
| 4-4 | CN | H | F | H | O |
| 4-5 | H | H | Cl | H | O |
| 4-6 | F | H | Cl | H | O |
| 4-7 | OH | H | Cl | H | O |
| 4-8 | CN | H | Cl | H | O |
| 4-9 | H | H | Br | H | O |
| 4-10 | F | H | Br | H | O |
| 4-11 | OH | H | Br | H | O |
| 4-12 | CN | H | Br | H | O |
| 4-13 | H | H | $CF_3$ | H | O |
| 4-14 | F | H | $CF_3$ | H | O |
| 4-15 | OH | H | $CF_3$ | H | O |
| 4-16 | CN | H | $CF_3$ | H | O |
| 4-17 | H | H | $OCH_3$ | H | O |
| 4-18 | F | H | $OCH_3$ | H | O |
| 4-19 | OH | H | $OCH_3$ | H | O |
| 4-20 | CN | H | $OCH_3$ | H | O |
| 4-21 | H | H | $CH_3$ | H | O |
| 4-22 | F | H | $CH_3$ | H | O |
| 4-23 | OH | H | $CH_3$ | H | O |
| 4-24 | CN | H | $CH_3$ | H | O |
| 4-25 | H | H | Cl | H | S |
| 4-26 | H | OH | F | H | O |
| 4-27 | F | OH | F | H | O |
| 4-28 | OH | OH | F | H | O |
| 4-29 | CN | OH | F | H | O |
| 4-30 | H | OH | Cl | H | O |
| 4-31 | F | OH | Cl | H | O |
| 4-32 | OH | OH | Cl | H | O |
| 4-33 | CN | OH | Cl | H | O |
| 4-34 | H | OH | Br | H | O |
| 4-35 | F | OH | Br | H | O |
| 4-36 | OH | OH | Br | H | O |
| 4-37 | CN | OH | Br | H | O |
| 4-38 | H | OH | $CF_3$ | H | O |
| 4-39 | F | OH | $CF_3$ | H | O |
| 4-40 | OH | OH | $CF_3$ | H | O |
| 4-41 | CN | OH | $CF_3$ | H | O |
| 4-42 | H | OH | $OCH_3$ | H | O |
| 4-43 | F | OH | $OCH_3$ | H | O |
| 4-44 | OH | OH | $OCH_3$ | H | O |
| 4-45 | CN | OH | $OCH_3$ | H | O |
| 4-46 | H | OH | $CH_3$ | H | O |
| 4-47 | F | OH | $CH_3$ | H | O |
| 4-48 | OH | OH | $CH_3$ | H | O |
| 4-49 | CN | OH | $CH_3$ | H | O |
| 4-50 | H | OH | Cl | H | S |
| 4-51 | F | OH | Cl | H | S |
| 4-52 | OH | OH | Cl | H | S |
| 4-53 | CN | OH | Cl | H | S |
| 4-54 | H | CN | F | H | O |
| 4-55 | F | CN | F | H | O |
| 4-56 | OH | CN | F | H | O |
| 4-57 | CN | CN | F | H | O |
| 4-58 | H | CN | Cl | H | O |
| 4-59 | F | CN | Cl | H | O |
| 4-60 | OH | CN | Cl | H | O |
| 4-61 | CN | CN | Cl | H | O |
| 4-62 | H | CN | Br | H | O |
| 4-63 | F | CN | Br | H | O |
| 4-64 | OH | CN | Br | H | O |
| 4-65 | CN | CN | Br | H | O |
| 4-66 | H | CN | $CF_3$ | H | O |
| 4-67 | F | CN | $CF_3$ | H | O |
| 4-68 | OH | CN | $CF_3$ | H | O |
| 4-69 | CN | CN | $CF_3$ | H | O |
| 4-70 | H | CN | $OCH_3$ | H | O |
| 4-71 | F | CN | $OCH_3$ | H | O |
| 4-72 | OH | CN | $OCH_3$ | H | O |
| 4-73 | CN | CN | $OCH_3$ | H | O |
| 4-74 | H | CN | $CH_3$ | H | O |
| 4-75 | F | CN | $CH_3$ | H | O |
| 4-76 | OH | CN | $CH_3$ | H | O |
| 4-77 | CN | CN | $CH_3$ | H | O |
| 4-78 | H | H | Cl | 4-F | O |
| 4-79 | H | H | Cl | 5-F | O |
| 4-80 | H | H | Cl | 6-F | O |

$R^{1a}$=H, $(R^{1b})_n$=H, $R^2$=F, $(R^3)_m$=H and Z=O, and each value for R is described in Exhibit 2.

The present disclosure also includes Tables 4-2 through 4-80. Each Table is constructed in the same manner as Table 4-1 above, except that the row heading in Table 4-1 (i.e. "$R^{1a}$=H, $(R^{1b})_n$=H, $R^2$=F, $(R^3)_m$=H and Z=O") is replaced with the respective row heading shown below. For example, the first entry in Table 4-2 is a compound of Formula 1-4 wherein $R^{1a}$ is F, $(R^{1b})_n$=H, $R^2$ is F, $(R^3)_m$ is H and Z is O and R is butyl. Tables 4-3 through 4-80 are constructed similarly.

TABLE 5-1

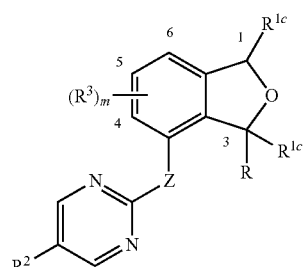

1-5

| Table | $R^{1c}$ | $R^2$ | $(R^3)_m$ | Z |
|---|---|---|---|---|
| 5-2 | 1-H, 3-F | F | H | O |
| 5-3 | 1-H, 3-OH | F | H | O |
| 5-4 | 1-H, 3-CN | F | H | O |
| 5-5 | 1-H, 3-H | Cl | H | O |
| 5-6 | 1-H, 3-F | Cl | H | O |
| 5-7 | 1-H, 3-OH | Cl | H | O |

TABLE 5-1-continued

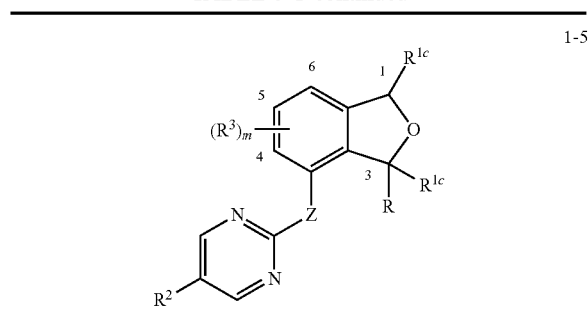

1-5

| Table | R$^{1c}$ | R$^2$ | (R$^3$)$_m$ | Z |
|---|---|---|---|---|
| 5-8 | 1-H, 3-CN | Cl | H | O |
| 5-9 | 1-H, 3-H | Br | H | O |
| 5-10 | 1-H, 3-F | Br | H | O |
| 5-11 | 1-H, 3-OH | Br | H | O |
| 5-12 | 1-H, 3-CN | Br | H | O |
| 5-13 | 1-H, 3-H | CF$_3$ | H | O |
| 5-14 | 1-H, 3-F | CF$_3$ | H | O |
| 5-15 | 1-H, 3-OH | CF$_3$ | H | O |
| 5-16 | 1-H, 3-CN | CF$_3$ | H | O |
| 5-17 | 1-H, 3-H | OCH$_3$ | H | O |
| 5-18 | 1-H, 3-F | OCH$_3$ | H | O |
| 5-19 | 1-H, 3-OH | OCH$_3$ | H | O |
| 5-20 | 1-H, 3-CN | OCH$_3$ | H | O |
| 5-21 | 1-H, 3-H | CH$_3$ | H | O |
| 5-22 | 1-H, 3-F | CH$_3$ | H | O |
| 5-23 | 1-H, 3-OH | CH$_3$ | H | O |
| 5-24 | 1-H, 3-CN | CH$_3$ | H | O |
| 5-25 | 1-H, 3-H | F | 4-F | O |
| 5-26 | 1-H, 3-F | F | 4-F | O |
| 5-27 | 1-H, 3-OH | F | 4-F | O |
| 5-28 | 1-H, 3-CN | F | 4-F | O |
| 5-29 | 1-H, 3-H | Cl | 4-F | O |
| 5-30 | 1-H, 3-F | Cl | 4-F | O |
| 5-31 | 1-H, 3-OH | Cl | 4-F | O |
| 5-32 | 1-H, 3-CN | Cl | 4-F | O |
| 5-33 | 1-H, 3-H | Br | 4-F | O |
| 5-34 | 1-H, 3-F | Br | 4-F | O |
| 5-35 | 1-H, 3-OH | Br | 4-F | O |
| 5-36 | 1-H, 3-CN | Br | 4-F | O |
| 5-37 | 1-H, 3-H | CF$_3$ | 4-F | O |
| 5-38 | 1-H, 3-F | CF$_3$ | 4-F | O |
| 5-39 | 1-H, 3-OH | CF$_3$ | 4-F | O |
| 5-40 | 1-H, 3-CN | CF$_3$ | 4-F | O |
| 5-41 | 1-H, 3-H | OCH$_3$ | 4-F | O |
| 5-42 | 1-H, 3-F | OCH$_3$ | 4-F | O |
| 5-43 | 1-H, 3-OH | OCH$_3$ | 4-F | O |
| 5-44 | 1-H, 3-CN | OCH$_3$ | 4-F | O |
| 5-45 | 1-H, 3-H | CH$_3$ | 4-F | O |
| 5-46 | 1-H, 3-F | CH$_3$ | 4-F | O |
| 5-47 | 1-H, 3-OH | CH$_3$ | 4-F | O |
| 5-48 | 1-H, 3-CN | CH$_3$ | 4-F | O |
| 5-49 | 1-H, 3-H | F | 5-F | O |
| 5-50 | 1-H, 3-F | F | 5-F | O |
| 5-51 | 1-H, 3-OH | F | 5-F | O |
| 5-52 | 1-H, 3-CN | F | 5-F | O |
| 5-53 | 1-H, 3-H | Cl | 5-F | O |
| 5-54 | 1-H, 3-F | Cl | 5-F | O |
| 5-55 | 1-H, 3-OH | Cl | 5-F | O |
| 5-56 | 1-H, 3-CN | Cl | 5-F | O |
| 5-57 | 1-H, 3-H | Br | 5-F | O |
| 5-58 | 1-H, 3-F | Br | 5-F | O |
| 5-59 | 1-H, 3-OH | Br | 5-F | O |
| 5-60 | 1-H, 3-CN | Br | 5-F | O |
| 5-61 | 1-H, 3-H | CF$_3$ | 5-F | O |
| 5-62 | 1-H, 3-F | CF$_3$ | 5-F | O |
| 5-63 | 1-H, 3-OH | CF$_3$ | 5-F | O |
| 5-64 | 1-H, 3-CN | CF$_3$ | 5-F | O |
| 5-65 | 1-H, 3-H | OCH$_3$ | 5-F | O |
| 5-66 | 1-H, 3-F | OCH$_3$ | 5-F | O |
| 5-67 | 1-H, 3-OH | OCH$_3$ | 5-F | O |
| 5-68 | 1-H, 3-CN | OCH$_3$ | 5-F | O |

TABLE 5-1-continued

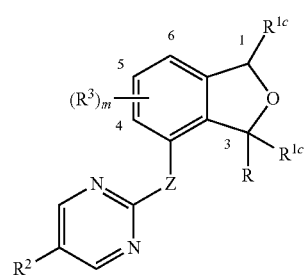

1-5

| Table | R$^{1c}$ | R$^2$ | (R$^3$)$_m$ | Z |
|---|---|---|---|---|
| 5-69 | 1-H, 3-H | CH$_3$ | 5-F | O |
| 5-70 | 1-H, 3-F | CH$_3$ | 5-F | O |
| 5-71 | 1-H, 3-OH | CH$_3$ | 5-F | O |
| 5-72 | 1-H, 3-CN | CH$_3$ | 5-F | O |
| 5-73 | 1-H, 3-H | F | 6-F | O |
| 5-74 | 1-H, 3-F | F | 6-F | O |
| 5-75 | 1-H, 3-OH | F | 6-F | O |
| 5-76 | 1-H, 3-CN | F | 6-F | O |
| 5-77 | 1-H, 3-H | Cl | 6-F | O |
| 5-78 | 1-H, 3-F | Cl | 6-F | O |
| 5-79 | 1-H, 3-OH | Cl | 6-F | O |
| 5-80 | 1-H, 3-CN | Cl | 6-F | O |
| 5-81 | 1-H, 3-H | Br | 6-F | O |
| 5-82 | 1-H, 3-F | Br | 6-F | O |
| 5-83 | 1-H, 3-OH | Br | 6-F | O |
| 5-84 | 1-H, 3-CN | Br | 6-F | O |
| 5-85 | 1-H, 3-H | CF$_3$ | 6-F | O |
| 5-86 | 1-H, 3-F | CF$_3$ | 6-F | O |
| 5-87 | 1-H, 3-OH | CF$_3$ | 6-F | O |
| 5-88 | 1-H, 3-CN | CF$_3$ | 6-F | O |
| 5-89 | 1-H, 3-H | OCH$_3$ | 6-F | O |
| 5-90 | 1-H, 3-F | OCH$_3$ | 6-F | O |
| 5-91 | 1-H, 3-OH | OCH$_3$ | 6-F | O |
| 5-92 | 1-H, 3-CN | OCH$_3$ | 6-F | O |
| 5-93 | 1-H, 3-H | CH$_3$ | 6-F | O |
| 5-94 | 1-H, 3-F | CH$_3$ | 6-F | O |
| 5-95 | 1-H, 3-OH | CH$_3$ | 6-F | O |
| 5-96 | 1-H, 3-CN | CH$_3$ | 6-F | O |
| 5-97 | 1-H, 3-H | Cl | H | S |
| 5-98 | 1-F, 3-H | F | H | O |
| 5-99 | 1-OH, 3-H | F | H | O |
| 5-100 | 1-CN, 3-H | F | H | O |
| 5-101 | 1-F, 3-H | Cl | H | O |
| 5-102 | 1-OH, 3-H | Cl | H | O |
| 5-103 | 1-CN, 3-H | Cl | H | O |
| 5-104 | 1-F, 3-H | Br | H | O |
| 5-105 | 1-OH, 3-H | Br | H | O |
| 5-106 | 1-CN, 3-H | Br | H | O |
| 5-107 | 1-F, 3-H | CF$_3$ | H | O |
| 5-108 | 1-OH, 3-H | CF$_3$ | H | O |
| 5-109 | 1-CN, 3-H | CF$_3$ | H | O |
| 5-110 | 1-F, 3-H | OCH$_3$ | H | O |
| 5-111 | 1-OH, 3-H | OCH$_3$ | H | O |
| 5-112 | 1-CN, 3-H | OCH$_3$ | H | O |
| 5-113 | 1-F, 3-H | CH$_3$ | H | O |
| 5-114 | 1-OH, 3-H | CH$_3$ | H | O |
| 5-115 | 1-CN, 3-H | CH$_3$ | H | O |
| 5-116 | 1-F, 3-H | F | 4-F | O |
| 5-117 | 1-OH, 3-H | F | 4-F | O |
| 5-118 | 1-CN, 3-H | F | 4-F | O |
| 5-119 | 1-F, 3-H | Cl | 4-F | O |
| 5-120 | 1-OH, 3-H | Cl | 4-F | O |
| 5-121 | 1-CN, 3-H | Cl | 4-F | O |
| 5-122 | 1-F, 3-H | Br | 4-F | O |
| 5-123 | 1-OH, 3-H | Br | 4-F | O |
| 5-124 | 1-CN, 3-H | Br | 4-F | O |
| 5-125 | 1-F, 3-H | CF$_3$ | 4-F | O |
| 5-126 | 1-OH, 3-H | CF$_3$ | 4-F | O |
| 5-127 | 1-CN, 3-H | CF$_3$ | 4-F | O |
| 5-128 | 1-F, 3-H | OCH$_3$ | 4-F | O |
| 5-129 | 1-OH, 3-H | OCH$_3$ | 4-F | O |

TABLE 5-1-continued 1-5

| Table | $R^{1c}$ | $R^2$ | $(R^3)_m$ | Z |
|---|---|---|---|---|
| 5-130 | 1-CN, 3-H | OCH₃ | 4-F | O |
| 5-131 | 1-F, 3-H | CH₃ | 4-F | O |
| 5-132 | 1-OH, 3-H | CH₃ | 4-F | O |
| 5-133 | 1-CN, 3-H | CH₃ | 4-F | O |
| 5-134 | 1-F, 3-H | F | 5-F | O |
| 5-135 | 1-OH, 3-H | F | 5-F | O |
| 5-136 | 1-CN, 3-H | F | 5-F | O |
| 5-137 | 1-F, 3-H | Cl | 5-F | O |
| 5-138 | 1-OH, 3-H | Cl | 5-F | O |
| 5-139 | 1-CN, 3-H | Cl | 5-F | O |
| 5-140 | 1-F, 3-H | Br | 5-F | O |
| 5-141 | 1-OH, 3-H | Br | 5-F | O |
| 5-142 | 1-CN, 3-H | Br | 5-F | O |
| 5-143 | 1-F, 3-H | CF₃ | 5-F | O |
| 5-144 | 1-OH, 3-H | CF₃ | 5-F | O |
| 5-145 | 1-CN, 3-H | CF₃ | 5-F | O |
| 5-146 | 1-F, 3-H | OCH₃ | 5-F | O |
| 5-147 | 1-OH, 3-H | OCH₃ | 5-F | O |
| 5-148 | 1-CN, 3-H | OCH₃ | 5-F | O |
| 5-149 | 1-F, 3-H | CH₃ | 5-F | O |
| 5-150 | 1-OH, 3-H | CH₃ | 5-F | O |
| 5-151 | 1-CN, 3-H | CH₃ | 5-F | O |
| 5-152 | 1-F, 3-H | F | 6-F | O |
| 5-153 | 1-OH, 3-H | F | 6-F | O |
| 5-154 | 1-CN, 3-H | F | 6-F | O |
| 5-155 | 1-F, 3-H | Cl | 6-F | O |
| 5-156 | 1-OH, 3-H | Cl | 6-F | O |
| 5-157 | 1-CN, 3-H | Cl | 6-F | O |
| 5-158 | 1-F, 3-H | Br | 6-F | O |
| 5-159 | 1-OH, 3-H | Br | 6-F | O |
| 5-160 | 1-CN, 3-H | Br | 6-F | O |
| 5-161 | 1-F, 3-H | CF₃ | 6-F | O |
| 5-162 | 1-OH, 3-H | CF₃ | 6-F | O |
| 5-163 | 1-CN, 3-H | CF₃ | 6-F | O |
| 5-164 | 1-F, 3-H | OCH₃ | 6-F | O |
| 5-165 | 1-OH, 3-H | OCH₃ | 6-F | O |
| 5-166 | 1-CN, 3-H | OCH₃ | 6-F | O |
| 5-167 | 1-F, 3-H | CH₃ | 6-F | O |
| 5-168 | 1-OH, 3-H | CH₃ | 6-F | O |
| 5-169 | 1-CN, 3-H | CH₃ | 6-F | O |

$R^{1c}$=1-H, 3-H, $R^2$=F, $(R^3)_m$=H and Z=O, and each value for R is described in Exhibit 2.

The present disclosure also includes Tables 5-2 through 5-169. Each Table is constructed in the same manner as Table 5-1 above, except that the row heading in Table 5-1 (i.e. "$R^{1c}$=1-H, 3-H, $R^2$=F, $(R^3)_m$=H and Z=O") is replaced with the respective row heading shown below. For example, the first entry in Table 5-2 is a compound of Formula 1-5 wherein $R^{1c}$=1-H, 3-F, $R^2$ is F, $(R^3)_m$ is H and Z is O and R is butyl. Tables 5-3 through 5-169 are constructed similarly.

TABLE 6-1

1-6

| Table | $R^{1a}$ | $R^{1c}$ | $R^2$ | $(R^3)_m$ | Z |
|---|---|---|---|---|---|
| 6-2 | F | H | F | H | O |
| 6-3 | OH | H | F | H | O |
| 6-4 | CN | H | F | H | O |
| 6-5 | H | H | Cl | H | O |
| 6-6 | F | H | Cl | H | O |
| 6-7 | OH | H | Cl | H | O |
| 6-8 | CN | H | Cl | H | O |
| 6-9 | H | H | Br | H | O |
| 6-10 | F | H | Br | H | O |
| 6-11 | OH | H | Br | H | O |
| 6-12 | CN | H | Br | H | O |
| 6-13 | H | H | CF₃ | H | O |
| 6-14 | F | H | CF₃ | H | O |
| 6-15 | OH | H | CF₃ | H | O |
| 6-16 | CN | H | CF₃ | H | O |
| 6-17 | H | H | OCH₃ | H | O |
| 6-18 | F | H | OCH₃ | H | O |
| 6-19 | OH | H | OCH₃ | H | O |
| 6-20 | CN | H | OCH₃ | H | O |
| 6-21 | H | H | CH₃ | H | O |
| 6-22 | F | H | CH₃ | H | O |
| 6-23 | OH | H | CH₃ | H | O |
| 6-24 | CN | H | CH₃ | H | O |
| 6-25 | H | H | F | 4-F | O |
| 6-26 | F | H | F | 4-F | O |
| 6-27 | OH | H | F | 4-F | O |
| 6-28 | CN | H | F | 4-F | O |
| 6-29 | H | H | Cl | 4-F | O |
| 6-30 | F | H | Cl | 4-F | O |
| 6-31 | OH | H | Cl | 4-F | O |
| 6-32 | CN | H | Cl | 4-F | O |
| 6-33 | H | H | Br | 4-F | O |
| 6-34 | F | H | Br | 4-F | O |
| 6-35 | OH | H | Br | 4-F | O |
| 6-36 | CN | H | Br | 4-F | O |
| 6-37 | H | H | CF₃ | 4-F | O |
| 6-38 | F | H | CF₃ | 4-F | O |
| 6-39 | OH | H | CF₃ | 4-F | O |
| 6-40 | CN | H | CF₃ | 4-F | O |
| 6-41 | H | H | OCH₃ | 4-F | O |
| 6-42 | F | H | OCH₃ | 4-F | O |
| 6-43 | OH | H | OCH₃ | 4-F | O |
| 6-44 | CN | H | OCH₃ | 4-F | O |
| 6-45 | H | H | CH₃ | 4-F | O |
| 6-46 | F | H | CH₃ | 4-F | O |
| 6-47 | OH | H | CH₃ | 4-F | O |
| 6-48 | CN | H | CH₃ | 4-F | O |
| 6-49 | H | H | F | 5-F | O |
| 6-50 | F | H | F | 5-F | O |
| 6-51 | OH | H | F | 5-F | O |
| 6-52 | CN | H | F | 5-F | O |
| 6-53 | H | H | Cl | 5-F | O |
| 6-54 | F | H | Cl | 5-F | O |
| 6-55 | OH | H | Cl | 5-F | O |
| 6-56 | CN | H | Cl | 5-F | O |
| 6-57 | H | H | Br | 5-F | O |
| 6-58 | F | H | Br | 5-F | O |
| 6-59 | OH | H | Br | 5-F | O |
| 6-60 | CN | H | Br | 5-F | O |
| 6-61 | H | H | CF₃ | 5-F | O |
| 6-62 | F | H | CF₃ | 5-F | O |

TABLE 6-1-continued 1-6

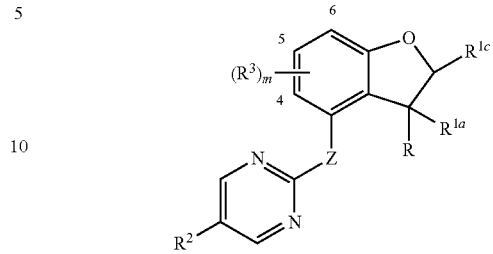

Header Row

| Table | $R^{1a}$ | $R^{1c}$ | $R^2$ | $(R^3)_m$ | Z |
|---|---|---|---|---|---|
| 6-63 | OH | H | CF₃ | 5-F | O |
| 6-64 | CN | H | CF₃ | 5-F | O |
| 6-65 | H | H | OCH₃ | 5-F | O |
| 6-66 | F | H | OCH₃ | 5-F | O |
| 6-67 | OH | H | OCH₃ | 5-F | O |
| 6-68 | CN | H | OCH₃ | 5-F | O |
| 6-69 | H | H | CH₃ | 5-F | O |
| 6-70 | F | H | CH₃ | 5-F | O |
| 6-71 | OH | H | CH₃ | 5-F | O |
| 6-72 | CN | H | CH₃ | 5-F | O |
| 6-73 | H | H | F | 6-F | O |
| 6-74 | F | H | F | 6-F | O |
| 6-75 | OH | H | F | 6-F | O |
| 6-76 | CN | H | F | 6-F | O |
| 6-77 | H | H | Cl | 6-F | O |
| 6-78 | F | H | Cl | 6-F | O |
| 6-79 | OH | H | Cl | 6-F | O |
| 6-80 | CN | H | Cl | 6-F | O |
| 6-81 | H | H | Br | 6-F | O |
| 6-82 | F | H | Br | 6-F | O |
| 6-83 | OH | H | Br | 6-F | O |
| 6-84 | CN | H | Br | 6-F | O |
| 6-85 | H | H | CF₃ | 6-F | O |
| 6-86 | F | H | CF₃ | 6-F | O |
| 6-87 | OH | H | CF₃ | 6-F | O |
| 6-88 | CN | H | CF₃ | 6-F | O |
| 6-89 | H | H | OCH₃ | 6-F | O |
| 6-90 | F | H | OCH₃ | 6-F | O |
| 6-91 | OH | H | OCH₃ | 6-F | O |
| 6-92 | CN | H | OCH₃ | 6-F | O |
| 6-93 | H | H | CH₃ | 6-F | O |
| 6-94 | F | H | CH₃ | 6-F | O |
| 6-95 | OH | H | CH₃ | 6-F | O |
| 6-96 | CN | H | CH₃ | 6-F | O |
| 6-97 | H | H | Cl | H | S |
| 6-98 | F | H | Cl | H | S |
| 6-99 | OH | H | Cl | H | S |
| 6-100 | CN | H | Cl | H | S |
| 6-101 | H | OH | F | H | O |
| 6-102 | H | CN | F | H | O |
| 6-103 | H | OH | Cl | H | O |
| 6-104 | H | CN | Cl | H | O |
| 6-105 | H | OH | Br | H | O |
| 6-106 | H | CN | Br | H | O |
| 6-107 | H | OH | CF₃ | H | O |
| 6-108 | H | CN | CF₃ | H | O |
| 6-109 | H | OH | OCH₃ | H | O |
| 6-110 | H | CN | OCH₃ | H | O |
| 6-111 | H | OH | CH₃ | H | O |
| 6-112 | H | CN | CH₃ | H | O |
| 6-113 | H | OH | F | 4-F | O |
| 6-114 | H | CN | F | 4-F | O |
| 6-115 | H | OH | Cl | 4-F | O |
| 6-116 | H | CN | Cl | 4-F | O |
| 6-117 | H | OH | Br | 4-F | O |
| 6-118 | H | CN | Br | 4-F | O |
| 6-119 | H | OH | CF₃ | 4-F | O |
| 6-120 | H | CN | CF₃ | 4-F | O |
| 6-121 | H | OH | OCH₃ | 4-F | O |
| 6-122 | H | CN | OCH₃ | 4-F | O |
| 6-123 | H | OH | CH₃ | 4-F | O |
| 6-124 | H | CN | CH₃ | 4-F | O |
| 6-125 | H | OH | F | 5-F | O |
| 6-126 | H | CN | F | 5-F | O |
| 6-127 | H | OH | Cl | 5-F | O |
| 6-128 | H | CN | Cl | 5-F | O |
| 6-129 | H | OH | Br | 5-F | O |
| 6-130 | H | CN | Br | 5-F | O |
| 6-131 | H | OH | CF₃ | 5-F | O |
| 6-132 | H | CN | CF₃ | 5-F | O |
| 6-133 | H | OH | OCH₃ | 5-F | O |
| 6-134 | H | CN | OCH₃ | 5-F | O |
| 6-135 | H | OH | CH₃ | 5-F | O |
| 6-136 | H | CN | CH₃ | 5-F | O |
| 6-137 | H | OH | F | 6-F | O |
| 6-138 | H | CN | F | 6-F | O |
| 6-139 | H | OH | Cl | 6-F | O |
| 6-140 | H | CN | Cl | 6-F | O |
| 6-141 | H | OH | Br | 6-F | O |
| 6-142 | H | CN | Br | 6-F | O |
| 6-143 | H | OH | CF₃ | 6-F | O |
| 6-144 | H | CN | CF₃ | 6-F | O |
| 6-145 | H | OH | OCH₃ | 6-F | O |
| 6-146 | H | CN | OCH₃ | 6-F | O |
| 6-147 | H | OH | CH₃ | 6-F | O |
| 6-148 | H | CN | CH₃ | 6-F | O |

$R^{1a}$=H, $R^{1c}$=H, $R^2$=F, $(R^3)_m$=H and Z=O, and each value for R is described in Exhibit 2.

The present disclosure also includes Tables 6-2 through 6-148. Each Table is constructed in the same manner as Table 6-1 above, except that the row heading in Table 6-1 (i.e. "$R^{1a}$=H, $R^{1c}$=H, $R^2$=F, $(R^3)_m$=H and Z=O") is replaced with the respective row heading shown below. For example, the first entry in Table 6-2 is a compound of Formula 1-6 wherein $R^{1a}$ is F, $R^{1c}$=H, $R^2$ is F, $(R^3)_m$ is H and Z is O and R is butyl. Tables 6-3 through 6-148 are constructed similarly.

TABLE 7-1

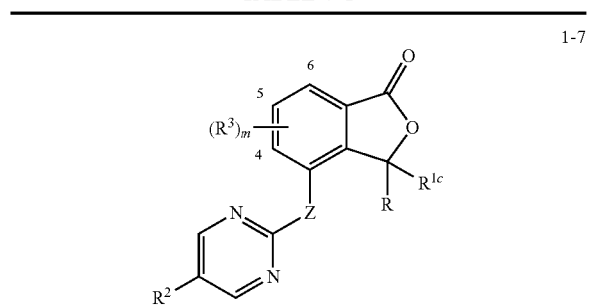

| Table | $R^{1c}$ | $R^2$ | $(R^3)_m$ | Z |
|---|---|---|---|---|
| 7-2 | F | F | H | O |
| 7-3 | OH | F | H | O |
| 7-4 | CN | F | H | O |
| 7-5 | H | Cl | H | O |
| 7-6 | F | Cl | H | O |
| 7-7 | OH | Cl | H | O |
| 7-8 | CN | Cl | H | O |
| 7-9 | H | Br | H | O |
| 7-10 | F | Br | H | O |
| 7-11 | OH | Br | H | O |
| 7-12 | CN | Br | H | O |
| 7-13 | H | $CF_3$ | H | O |
| 7-14 | F | $CF_3$ | H | O |
| 7-15 | OH | $CF_3$ | H | O |
| 7-16 | CN | $CF_3$ | H | O |
| 7-17 | H | $OCH_3$ | H | O |
| 7-18 | F | $OCH_3$ | H | O |
| 7-19 | OH | $OCH_3$ | H | O |
| 7-20 | CN | $OCH_3$ | H | O |
| 7-21 | H | $CH_3$ | H | O |
| 7-22 | F | $CH_3$ | H | O |
| 7-23 | OH | $CH_3$ | H | O |
| 7-24 | CN | $CH_3$ | H | O |
| 7-25 | H | F | 4-F | O |
| 7-26 | F | F | 4-F | O |
| 7-27 | OH | F | 4-F | O |
| 7-28 | CN | F | 4-F | O |
| 7-29 | H | Cl | 4-F | O |
| 7-30 | F | Cl | 4-F | O |
| 7-31 | OH | Cl | 4-F | O |
| 7-32 | CN | Cl | 4-F | O |
| 7-33 | H | Br | 4-F | O |
| 7-34 | F | Br | 4-F | O |
| 7-35 | OH | Br | 4-F | O |
| 7-36 | CN | Br | 4-F | O |
| 7-37 | H | $CF_3$ | 4-F | O |
| 7-38 | F | $CF_3$ | 4-F | O |
| 7-39 | OH | $CF_3$ | 4-F | O |
| 7-40 | CN | $CF_3$ | 4-F | O |
| 7-41 | H | $OCH_3$ | 4-F | O |
| 7-42 | F | $OCH_3$ | 4-F | O |
| 7-43 | OH | $OCH_3$ | 4-F | O |
| 7-44 | CN | $OCH_3$ | 4-F | O |
| 7-45 | H | $CH_3$ | 4-F | O |
| 7-46 | F | $CH_3$ | 4-F | O |
| 7-47 | OH | $CH_3$ | 4-F | O |
| 7-48 | CN | $CH_3$ | 4-F | O |
| 7-49 | H | F | 5-F | O |
| 7-50 | F | F | 5-F | O |
| 7-51 | OH | F | 5-F | O |
| 7-52 | CN | F | 5-F | O |
| 7-53 | H | Cl | 5-F | O |
| 7-54 | F | Cl | 5-F | O |
| 7-55 | OH | Cl | 5-F | O |
| 7-56 | CN | Cl | 5-F | O |
| 7-57 | H | Br | 5-F | O |
| 7-58 | F | Br | 5-F | O |
| 7-59 | OH | Br | 5-F | O |
| 7-60 | CN | Br | 5-F | O |
| 7-61 | H | $CF_3$ | 5-F | O |
| 7-62 | F | $CF_3$ | 5-F | O |
| 7-63 | OH | $CF_3$ | 5-F | O |
| 7-64 | CN | $CF_3$ | 5-F | O |
| 7-65 | H | $OCH_3$ | 5-F | O |
| 7-66 | F | $OCH_3$ | 5-F | O |
| 7-67 | OH | $OCH_3$ | 5-F | O |
| 7-68 | CN | $OCH_3$ | 5-F | O |
| 7-69 | H | $CH_3$ | 5-F | O |
| 7-70 | F | $CH_3$ | 5-F | O |
| 7-71 | OH | $CH_3$ | 5-F | O |
| 7-72 | CN | $CH_3$ | 5-F | O |
| 7-73 | H | F | 6-F | O |
| 7-74 | F | F | 6-F | O |
| 7-75 | OH | F | 6-F | O |
| 7-76 | CN | F | 6-F | O |
| 7-77 | H | Cl | 6-F | O |
| 7-78 | F | Cl | 6-F | O |
| 7-79 | OH | Cl | 6-F | O |
| 7-80 | CN | Cl | 6-F | O |
| 7-81 | H | Br | 6-F | O |
| 7-82 | F | Br | 6-F | O |
| 7-83 | OH | Br | 6-F | O |
| 7-84 | CN | Br | 6-F | O |
| 7-85 | H | $CF_3$ | 6-F | O |
| 7-86 | F | $CF_3$ | 6-F | O |
| 7-87 | OH | $CF_3$ | 6-F | O |
| 7-88 | CN | $CF_3$ | 6-F | O |
| 7-89 | H | $OCH_3$ | 6-F | O |
| 7-90 | F | $OCH_3$ | 6-F | O |
| 7-91 | OH | $OCH_3$ | 6-F | O |
| 7-92 | CN | $OCH_3$ | 6-F | O |
| 7-93 | H | $CH_3$ | 6-F | O |
| 7-94 | F | $CH_3$ | 6-F | O |
| 7-95 | OH | $CH_3$ | 6-F | O |
| 7-96 | CN | $CH_3$ | 6-F | O |
| 7-97 | H | Cl | H | S |
| 7-98 | F | Cl | H | S |
| 7-99 | OH | Cl | H | S |
| 7-100 | CN | Cl | H | S |
| 7-101 | Me | Cl | H | O |
| 7-102 | OMe | Cl | H | O |
| 7-103 | $OCHF_2$ | Cl | H | O |
| 7-104 | $OCF_3$ | Cl | H | O |
| 7-105 | $CF_3$ | Cl | H | O |
| 7-106 | H | Cl | 4-Cl | O |
| 7-107 | H | Cl | 5-Cl | O |
| 7-108 | H | Cl | 6-Cl | O |
| 7-109 | H | Cl | 4-F, 5-F | O |
| 7-110 | H | Cl | 4-F, 6-F | O |
| 7-111 | H | Cl | 5-F, 6-F | O |
| 7-112 | H | Cl | 4-F, 5-Cl | O |
| 7-113 | H | Cl | 4-F, 6-Cl | O |
| 7-114 | H | Cl | 4-Cl, 5-F | O |
| 7-115 | H | Cl | 4-Cl, 6-F | O |
| 7-116 | H | Cl | 5-Cl, 6-F | O |
| 7-117 | H | Cl | 4-Cl, 5-Cl | O |
| 7-118 | H | Cl | 4-Cl, 6-Cl | O |
| 7-119 | H | Cl | 5-Cl, 6-Cl | O |

$R^{1c}$=H, $R^2$=F, $(R^3)_m$=H and Z=O, and each value for R is described in Exhibit 2.

The present disclosure also includes Tables 7-2 through 7-119. Each Table is constructed in the same manner as Table 7-1 above, except that the row heading in Table 7-1 (i.e. "$R^{1c}$=H, $R^2$=F, $(R^3)_m$=H and Z=O") is replaced with the respective row heading shown below. For example, the first entry in Table 7-2 is a compound of Formula 1-7 wherein $R^{1c}$ is F, $R^2$ is F, $(R^3)_m$ is H and Z is O and R is butyl. Tables 7-3 through 7-119 are constructed similarly.

TABLE 8-1

1-8

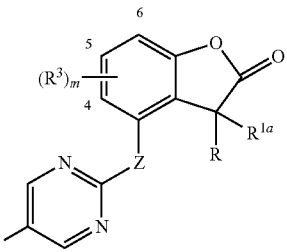

| Table | $R^{1c}$ | $R^2$ | $(R^3)_m$ | Z |
|---|---|---|---|---|
| 8-2 | F | F | H | O |
| 8-3 | OH | F | H | O |
| 8-4 | CN | F | H | O |
| 8-5 | H | Cl | H | O |
| 8-6 | F | Cl | H | O |
| 8-7 | OH | Cl | H | O |
| 8-8 | CN | Cl | H | O |
| 8-9 | H | Br | H | O |
| 8-10 | F | Br | H | O |
| 8-11 | OH | Br | H | O |
| 8-12 | CN | Br | H | O |
| 8-13 | H | $CF_3$ | H | O |
| 8-14 | F | $CF_3$ | H | O |
| 8-15 | OH | $CF_3$ | H | O |
| 8-16 | CN | $CF_3$ | H | O |
| 8-17 | H | $OCH_3$ | H | O |
| 8-18 | F | $OCH_3$ | H | O |
| 8-19 | OH | $OCH_3$ | H | O |
| 8-20 | CN | $OCH_3$ | H | O |
| 8-21 | H | $CH_3$ | H | O |
| 8-22 | F | $CH_3$ | H | O |
| 8-23 | OH | $CH_3$ | H | O |
| 8-24 | CN | $CH_3$ | H | O |
| 8-25 | H | F | 4-F | O |
| 8-26 | F | F | 4-F | O |
| 8-27 | OH | F | 4-F | O |
| 8-28 | CN | F | 4-F | O |
| 8-29 | H | Cl | 4-F | O |
| 8-30 | F | Cl | 4-F | O |
| 8-31 | OH | Cl | 4-F | O |
| 8-32 | CN | Cl | 4-F | O |
| 8-33 | H | Br | 4-F | O |
| 8-34 | F | Br | 4-F | O |
| 8-35 | OH | Br | 4-F | O |
| 8-36 | CN | Br | 4-F | O |
| 8-37 | H | $CF_3$ | 4-F | O |
| 8-38 | F | $CF_3$ | 4-F | O |
| 8-39 | OH | $CF_3$ | 4-F | O |
| 8-40 | CN | $CF_3$ | 4-F | O |
| 8-41 | H | $OCH_3$ | 4-F | O |
| 8-42 | F | $OCH_3$ | 4-F | O |
| 8-43 | OH | $OCH_3$ | 4-F | O |
| 8-44 | CN | $OCH_3$ | 4-F | O |
| 8-45 | H | $CH_3$ | 4-F | O |
| 8-46 | F | $CH_3$ | 4-F | O |
| 8-47 | OH | $CH_3$ | 4-F | O |
| 8-48 | CN | $CH_3$ | 4-F | O |
| 8-49 | H | F | 5-F | O |
| 8-50 | F | F | 5-F | O |
| 8-51 | OH | F | 5-F | O |
| 8-52 | CN | F | 5-F | O |
| 8-53 | H | Cl | 5-F | O |
| 8-54 | F | Cl | 5-F | O |
| 8-55 | OH | Cl | 5-F | O |
| 8-56 | CN | Cl | 5-F | O |
| 8-57 | H | Br | 5-F | O |
| 8-58 | F | Br | 5-F | O |
| 8-59 | OH | Br | 5-F | O |
| 8-60 | CN | Br | 5-F | O |
| 8-61 | H | $CF_3$ | 5-F | O |
| 8-62 | F | $CF_3$ | 5-F | O |
| 8-63 | OH | $CF_3$ | 5-F | O |
| 8-64 | CN | $CF_3$ | 5-F | O |
| 8-65 | H | $OCH_3$ | 5-F | O |
| 8-66 | F | $OCH_3$ | 5-F | O |
| 8-67 | OH | $OCH_3$ | 5-F | O |
| 8-68 | CN | $OCH_3$ | 5-F | O |
| 8-69 | H | $CH_3$ | 5-F | O |
| 8-70 | F | $CH_3$ | 5-F | O |
| 8-71 | OH | $CH_3$ | 5-F | O |
| 8-72 | CN | $CH_3$ | 5-F | O |
| 8-73 | H | F | 6-F | O |
| 8-74 | F | F | 6-F | O |
| 8-75 | OH | F | 6-F | O |
| 8-76 | CN | F | 6-F | O |
| 8-77 | H | Cl | 6-F | O |
| 8-78 | F | Cl | 6-F | O |
| 8-79 | OH | Cl | 6-F | O |
| 8-80 | CN | Cl | 6-F | O |
| 8-81 | H | Br | 6-F | O |
| 8-82 | F | Br | 6-F | O |
| 8-83 | OH | Br | 6-F | O |
| 8-84 | CN | Br | 6-F | O |
| 8-85 | H | $CF_3$ | 6-F | O |
| 8-86 | F | $CF_3$ | 6-F | O |
| 8-87 | OH | $CF_3$ | 6-F | O |
| 8-88 | CN | $CF_3$ | 6-F | O |
| 8-89 | H | $OCH_3$ | 6-F | O |
| 8-90 | F | $OCH_3$ | 6-F | O |
| 8-91 | OH | $OCH_3$ | 6-F | O |
| 8-92 | CN | $OCH_3$ | 6-F | O |
| 8-93 | H | $CH_3$ | 6-F | O |
| 8-94 | F | $CH_3$ | 6-F | O |
| 8-95 | OH | $CH_3$ | 6-F | O |
| 8-96 | CN | $CH_3$ | 6-F | O |
| 8-97 | H | Cl | H | S |
| 8-98 | F | Cl | H | S |
| 8-99 | OH | Cl | H | S |
| 8-100 | CN | Cl | H | S |

$R^{1a}$=H, $R^2$=F, $(R^3)_m$=H and Z=O, and each value for R is described in Exhibit 2.

The present disclosure also includes Tables 8-2 through 8-100. Each Table is constructed in the same manner as Table 8-1 above, except that the row heading in Table 8-1 (i.e. "$R^{1a}$=H, $R^2$=F, $(R^3)_m$=H and Z=O") is replaced with the respective row heading shown below. For example, the first entry in Table 8-2 is a compound of Formula 1-8 wherein $R^{1a}$ is F, $R^2$ is F, $(R^3)_m$ is H and Z is O and R is butyl. Tables 8-3 through 8-100 are constructed similarly.

TABLE 9-1

1-9

|       | Header Row |     |          |     |   |
|-------|-----|-----|----------|-----|---|
| Table | $R^{1c}$ | $R^2$ | $(R^3)_m$ | $R^4$ | Z |
| 9-2   | H   | Cl  | H        | H   | O |
| 9-3   | H   | Br  | H        | H   | O |
| 9-4   | H   | I   | H        | H   | O |
| 9-5   | H   | $CF_3$ | H     | H   | O |
| 9-6   | H   | $OCH_3$ | H    | H   | O |
| 9-7   | H   | $CH_3$ | H     | H   | O |
| 9-8   | H   | F   | H        | $CH_3$ | O |
| 9-9   | H   | Cl  | H        | $CH_3$ | O |
| 9-10  | H   | Br  | H        | $CH_3$ | O |
| 9-11  | H   | I   | H        | $CH_3$ | O |
| 9-12  | H   | $CF_3$ | H     | $CH_3$ | O |
| 9-13  | H   | $OCH_3$ | H    | $CH_3$ | O |
| 9-14  | H   | $CH_3$ | H     | $CH_3$ | O |

$R^{1c}$=H, $R^2$=F, $(R^3)_m$=H, $R^4$=H and Z=O, and each value for R is described in Exhibit 2.

The present disclosure also includes Tables 9-2 through 9-14. Each Table is constructed in the same manner as Table 9-1 above, except that the row heading in Table 9-1 (i.e. "$R^{1c}$=H, $R^2$=F, $(R^3)_m$=H, $R^4$=H and Z=O") is replaced with the respective row heading shown below. For example, the first entry in Table 9-2 is a compound of Formula 1-9 wherein $R^{1c}$ is H, $R^2$ is Cl, $(R^3)_m$ is H, $R^4$=H and Z is O and R is butyl. Tables 9-3 through 9-14 are constructed similarly.

TABLE 10-1

1-10

|       | Header Row |     |     |     |   |
|-------|-----|-----|-----|----------|---|
| Table | $R^{1a}$ | $R^{1c}$ | $R^2$ | $(R^3)_m$ | Z |
| 10-2  | F   | H   | F   | H   | O |
| 10-3  | OH  | H   | F   | H   | O |
| 10-4  | CN  | H   | F   | H   | O |
| 10-5  | H   | H   | Cl  | H   | O |
| 10-6  | F   | H   | Cl  | H   | O |
| 10-7  | OH  | H   | Cl  | H   | O |
| 10-8  | CN  | H   | Cl  | H   | O |
| 10-9  | H   | H   | Br  | H   | O |
| 10-10 | F   | H   | Br  | H   | O |
| 10-11 | OH  | H   | Br  | H   | O |
| 10-12 | CN  | H   | Br  | H   | O |
| 10-13 | H   | H   | $CF_3$ | H | O |
| 10-14 | F   | H   | $CF_3$ | H | O |
| 10-15 | OH  | H   | $CF_3$ | H | O |
| 10-16 | CN  | H   | $CF_3$ | H | O |
| 10-17 | H   | H   | $OCH_3$ | H | O |
| 10-18 | F   | H   | $OCH_3$ | H | O |
| 10-19 | OH  | H   | $OCH_3$ | H | O |
| 10-20 | CN  | H   | $OCH_3$ | H | O |
| 10-21 | H   | H   | $CH_3$ | H | O |
| 10-22 | F   | H   | $CH_3$ | H | O |
| 10-23 | OH  | H   | $CH_3$ | H | O |
| 10-24 | CN  | H   | $CH_3$ | H | O |
| 10-25 | H   | H   | F   | 4-F | O |
| 10-26 | F   | H   | F   | 4-F | O |
| 10-27 | OH  | H   | F   | 4-F | O |
| 10-28 | CN  | H   | F   | 4-F | O |
| 10-29 | H   | H   | Cl  | 4-F | O |
| 10-30 | F   | H   | Cl  | 4-F | O |
| 10-31 | OH  | H   | Cl  | 4-F | O |
| 10-32 | CN  | H   | Cl  | 4-F | O |
| 10-33 | H   | H   | Br  | 4-F | O |
| 10-34 | F   | H   | Br  | 4-F | O |
| 10-35 | OH  | H   | Br  | 4-F | O |
| 10-36 | CN  | H   | Br  | 4-F | O |
| 10-37 | H   | H   | $CF_3$ | 4-F | O |
| 10-38 | F   | H   | $CF_3$ | 4-F | O |
| 10-39 | OH  | H   | $CF_3$ | 4-F | O |
| 10-40 | CN  | H   | $CF_3$ | 4-F | O |
| 10-41 | H   | H   | $OCH_3$ | 4-F | O |
| 10-42 | F   | H   | $OCH_3$ | 4-F | O |
| 10-43 | OH  | H   | $OCH_3$ | 4-F | O |
| 10-44 | CN  | H   | $OCH_3$ | 4-F | O |
| 10-45 | H   | H   | $CH_3$ | 4-F | O |
| 10-46 | F   | H   | $CH_3$ | 4-F | O |
| 10-47 | OH  | H   | $CH_3$ | 4-F | O |
| 10-48 | CN  | H   | $CH_3$ | 4-F | O |
| 10-49 | H   | H   | F   | 5-F | O |
| 10-50 | F   | H   | F   | 5-F | O |
| 10-51 | OH  | H   | F   | 5-F | O |
| 10-52 | CN  | H   | F   | 5-F | O |
| 10-53 | H   | H   | Cl  | 5-F | O |
| 10-54 | F   | H   | Cl  | 5-F | O |
| 10-55 | OH  | H   | Cl  | 5-F | O |
| 10-56 | CN  | H   | Cl  | 5-F | O |
| 10-57 | H   | H   | Br  | 5-F | O |
| 10-58 | F   | H   | Br  | 5-F | O |
| 10-59 | OH  | H   | Br  | 5-F | O |
| 10-60 | CN  | H   | Br  | 5-F | O |
| 10-61 | H   | H   | $CF_3$ | 5-F | O |
| 10-62 | F   | H   | $CF_3$ | 5-F | O |
| 10-63 | OH  | H   | $CF_3$ | 5-F | O |
| 10-64 | CN  | H   | $CF_3$ | 5-F | O |
| 10-65 | H   | H   | $OCH_3$ | 5-F | O |
| 10-66 | F   | H   | $OCH_3$ | 5-F | O |
| 10-67 | OH  | H   | $OCH_3$ | 5-F | O |
| 10-68 | CN  | H   | $OCH_3$ | 5-F | O |
| 10-69 | H   | H   | $CH_3$ | 5-F | O |
| 10-70 | F   | H   | $CH_3$ | 5-F | O |
| 10-71 | OH  | H   | $CH_3$ | 5-F | O |
| 10-72 | CN  | H   | $CH_3$ | 5-F | O |
| 10-73 | H   | H   | F   | 6-F | O |
| 10-74 | F   | H   | F   | 6-F | O |

TABLE 10-1-continued

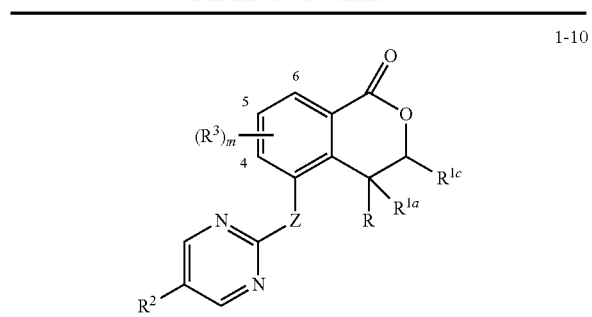

1-10

Header Row

| Table | R$^{1a}$ | R$^{1c}$ | R$^2$ | (R$^3$)$_m$ | Z |
|---|---|---|---|---|---|
| 10-75 | OH | H | F | 6-F | O |
| 10-76 | CN | H | F | 6-F | O |
| 10-77 | H | H | Cl | 6-F | O |
| 10-78 | F | H | Cl | 6-F | O |
| 10-79 | OH | H | Cl | 6-F | O |
| 10-80 | CN | H | Cl | 6-F | O |
| 10-81 | H | H | Br | 6-F | O |
| 10-82 | F | H | Br | 6-F | O |
| 10-83 | OH | H | Br | 6-F | O |
| 10-84 | CN | H | Br | 6-F | O |
| 10-85 | H | H | CF$_3$ | 6-F | O |
| 10-86 | F | H | CF$_3$ | 6-F | O |
| 10-87 | OH | H | CF$_3$ | 6-F | O |
| 10-88 | CN | H | CF$_3$ | 6-F | O |
| 10-89 | H | H | OCH$_3$ | 6-F | O |
| 10-90 | F | H | OCH$_3$ | 6-F | O |
| 10-91 | OH | H | OCH$_3$ | 6-F | O |
| 10-92 | CN | H | OCH$_3$ | 6-F | O |
| 10-93 | H | H | CH$_3$ | 6-F | O |
| 10-94 | F | H | CH$_3$ | 6-F | O |
| 10-95 | OH | H | CH$_3$ | 6-F | O |
| 10-96 | CN | H | CH$_3$ | 6-F | O |
| 10-97 | H | H | Cl | H | S |
| 10-98 | F | H | Cl | H | S |
| 10-99 | OH | H | Cl | H | S |
| 10-100 | CN | H | Cl | H | S |
| 10-101 | H | OH | F | H | O |
| 10-102 | H | CN | F | H | O |
| 10-103 | H | OH | Cl | H | O |
| 10-104 | H | CN | Cl | H | O |
| 10-105 | H | OH | Br | H | O |
| 10-106 | H | CN | Br | H | O |
| 10-107 | H | OH | CF$_3$ | H | O |
| 10-108 | H | CN | CF$_3$ | H | O |
| 10-109 | H | OH | OCH$_3$ | H | O |
| 10-110 | H | CN | OCH$_3$ | H | O |
| 10-111 | H | OH | CH$_3$ | H | O |
| 10-112 | H | CN | CH$_3$ | H | O |
| 10-113 | H | OH | F | 4-F | O |
| 10-114 | H | CN | F | 4-F | O |
| 10-115 | H | OH | Cl | 4-F | O |
| 10-116 | H | CN | Cl | 4-F | O |
| 10-117 | H | OH | Br | 4-F | O |
| 10-118 | H | CN | Br | 4-F | O |
| 10-119 | H | OH | CF$_3$ | 4-F | O |
| 10-120 | H | CN | CF$_3$ | 4-F | O |
| 10-121 | H | OH | OCH$_3$ | 4-F | O |
| 10-122 | H | CN | OCH$_3$ | 4-F | O |
| 10-123 | H | OH | CH$_3$ | 4-F | O |
| 10-124 | H | CN | CH$_3$ | 4-F | O |
| 10-125 | H | OH | F | 5-F | O |
| 10-126 | H | CN | F | 5-F | O |
| 10-127 | H | OH | Cl | 5-F | O |
| 10-128 | H | CN | Cl | 5-F | O |
| 10-129 | H | OH | Br | 5-F | O |
| 10-130 | H | CN | Br | 5-F | O |
| 10-131 | H | OH | CF$_3$ | 5-F | O |
| 10-132 | H | CN | CF$_3$ | 5-F | O |
| 10-133 | H | OH | OCH$_3$ | 5-F | O |
| 10-134 | H | CN | OCH$_3$ | 5-F | O |
| 10-135 | H | OH | CH$_3$ | 5-F | O |

TABLE 10-1-continued

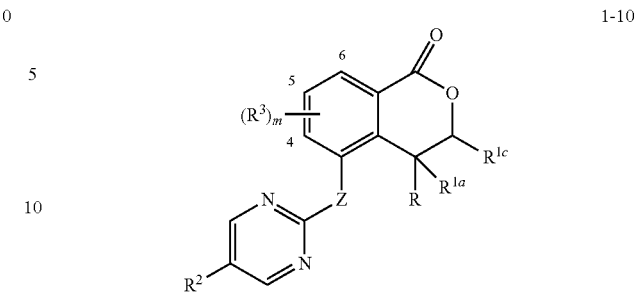

1-10

Header Row

| Table | R$^{1a}$ | R$^{1c}$ | R$^2$ | (R$^3$)$_m$ | Z |
|---|---|---|---|---|---|
| 10-136 | H | CN | CH$_3$ | 5-F | O |
| 10-137 | H | OH | F | 6-F | O |
| 10-138 | H | CN | F | 6-F | O |
| 10-139 | H | OH | Cl | 6-F | O |
| 10-140 | H | CN | Cl | 6-F | O |
| 10-141 | H | OH | Br | 6-F | O |
| 10-142 | H | CN | Br | 6-F | O |
| 10-143 | H | OH | CF$_3$ | 6-F | O |
| 10-144 | H | CN | CF$_3$ | 6-F | O |
| 10-145 | H | OH | OCH$_3$ | 6-F | O |
| 10-146 | H | CN | OCH$_3$ | 6-F | O |
| 10-147 | H | OH | CH$_3$ | 6-F | O |
| 10-148 | H | CN | CH$_3$ | 6-F | O |

R$^{1a}$=H, R$^{1c}$=H, R$^2$=F, (R$^3$)$_m$=H and Z=O, and each value for R is described in Exhibit 2.

The present disclosure also includes Tables 10-2 through 10-148. Each Table is constructed in the same manner as Table 10-1 above, except that the row heading in Table 10-1 (i.e. "R$^{1a}$=H, R$^{1c}$=H, R$^2$=F, (R$^3$)$_m$=H and Z=O") is replaced with the respective row heading shown below. For example, the first entry in Table 10-2 is a compound of Formula 1-10 wherein R$^{1a}$ is F, R$^{1c}$=H, R$^2$ is F, (R$^3$)$_m$ is H and Z is O and R is butyl. Tables 10-3 through 10-148 are constructed similarly.

TABLE 1-11

1-11

Header Row

| Table | (R$^{1b}$)$_n$ | R$^{1c}$ | R$^2$ | (R$^3$)$_m$ | Z |
|---|---|---|---|---|---|
| 11-2 | F | H | F | H | O |
| 11-3 | OH | H | F | H | O |
| 11-4 | CN | H | F | H | O |
| 11-5 | H | H | Cl | H | O |
| 11-6 | F | H | Cl | H | O |
| 11-7 | OH | H | Cl | H | O |
| 11-8 | CN | H | Cl | H | O |
| 11-9 | H | H | Br | H | O |
| 11-10 | F | H | Br | H | O |
| 11-11 | OH | H | Br | H | O |

TABLE 1-11-continued

| | | | | | |
|---|---|---|---|---|---|
| 11-12 | CN | H | Br | H | O |
| 11-13 | H | H | CF$_3$ | H | O |
| 11-14 | F | H | CF$_3$ | H | O |
| 11-15 | OH | H | CF$_3$ | H | O |
| 11-16 | CN | H | CF$_3$ | H | O |
| 11-17 | H | H | OCH$_3$ | H | O |
| 11-18 | F | H | OCH$_3$ | H | O |
| 11-19 | OH | H | OCH$_3$ | H | O |
| 11-20 | CN | H | OCH$_3$ | H | O |
| 11-21 | H | H | CH$_3$ | H | O |
| 11-22 | F | H | CH$_3$ | H | O |
| 11-23 | OH | H | CH$_3$ | H | O |
| 11-24 | CN | H | CH$_3$ | H | O |
| 11-25 | H | H | F | 4-F | O |
| 11-26 | F | H | F | 4-F | O |
| 11-27 | OH | H | F | 4-F | O |
| 11-28 | CN | H | F | 4-F | O |
| 11-29 | H | H | Cl | 4-F | O |
| 11-30 | F | H | Cl | 4-F | O |
| 11-31 | OH | H | Cl | 4-F | O |
| 11-32 | CN | H | Cl | 4-F | O |
| 11-33 | H | H | Br | 4-F | O |
| 11-34 | F | H | Br | 4-F | O |
| 11-35 | OH | H | Br | 4-F | O |
| 11-36 | CN | H | Br | 4-F | O |
| 11-37 | H | H | CF$_3$ | 4-F | O |
| 11-38 | F | H | CF$_3$ | 4-F | O |
| 11-39 | OH | H | CF$_3$ | 4-F | O |
| 11-40 | CN | H | CF$_3$ | 4-F | O |
| 11-41 | H | H | OCH$_3$ | 4-F | O |
| 11-42 | F | H | OCH$_3$ | 4-F | O |
| 11-43 | OH | H | OCH$_3$ | 4-F | O |
| 11-44 | CN | H | OCH$_3$ | 4-F | O |
| 11-45 | H | H | CH$_3$ | 4-F | O |
| 11-46 | F | H | CH$_3$ | 4-F | O |
| 11-47 | OH | H | CH$_3$ | 4-F | O |
| 11-48 | CN | H | CH$_3$ | 4-F | O |
| 11-49 | H | H | F | 5-F | O |
| 11-50 | F | H | F | 5-F | O |
| 11-51 | OH | H | F | 5-F | O |
| 11-52 | CN | H | F | 5-F | O |
| 11-53 | H | H | Cl | 5-F | O |
| 11-54 | F | H | Cl | 5-F | O |
| 11-55 | OH | H | Cl | 5-F | O |
| 11-56 | CN | H | Cl | 5-F | O |
| 11-57 | H | H | Br | 5-F | O |
| 11-58 | F | H | Br | 5-F | O |
| 11-59 | OH | H | Br | 5-F | O |
| 11-60 | CN | H | Br | 5-F | O |
| 11-61 | H | H | CF$_3$ | 5-F | O |
| 11-62 | F | H | CF$_3$ | 5-F | O |
| 11-63 | OH | H | CF$_3$ | 5-F | O |
| 11-64 | CN | H | CF$_3$ | 5-F | O |
| 11-65 | H | H | OCH$_3$ | 5-F | O |
| 11-66 | F | H | OCH$_3$ | 5-F | O |
| 11-67 | OH | H | OCH$_3$ | 5-F | O |
| 11-68 | CN | H | OCH$_3$ | 5-F | O |
| 11-69 | H | H | CH$_3$ | 5-F | O |
| 11-70 | F | H | CH$_3$ | 5-F | O |
| 11-71 | OH | H | CH$_3$ | 5-F | O |
| 11-72 | CN | H | CH$_3$ | 5-F | O |
| 11-73 | H | H | F | 6-F | O |
| 11-74 | F | H | F | 6-F | O |
| 11-75 | OH | H | F | 6-F | O |
| 11-76 | CN | H | F | 6-F | O |
| 11-77 | H | H | Cl | 6-F | O |
| 11-78 | F | H | Cl | 6-F | O |
| 11-79 | OH | H | Cl | 6-F | O |
| 11-80 | CN | H | Cl | 6-F | O |
| 11-81 | H | H | Br | 6-F | O |
| 11-82 | F | H | Br | 6-F | O |
| 11-83 | OH | H | Br | 6-F | O |
| 11-84 | CN | H | Br | 6-F | O |
| 11-85 | H | H | CF$_3$ | 6-F | O |
| 11-86 | F | H | CF$_3$ | 6-F | O |
| 11-87 | OH | H | CF$_3$ | 6-F | O |
| 11-88 | CN | H | CF$_3$ | 6-F | O |
| 11-89 | H | H | OCH$_3$ | 6-F | O |
| 11-90 | F | H | OCH$_3$ | 6-F | O |
| 11-91 | OH | H | OCH$_3$ | 6-F | O |
| 11-92 | CN | H | OCH$_3$ | 6-F | O |
| 11-93 | H | H | CH$_3$ | 6-F | O |
| 11-94 | F | H | CH$_3$ | 6-F | O |
| 11-95 | OH | H | CH$_3$ | 6-F | O |
| 11-96 | CN | H | CH$_3$ | 6-F | O |
| 11-97 | H | H | Cl | H | S |
| 11-98 | F | H | Cl | H | S |
| 11-99 | OH | H | Cl | H | S |
| 11-100 | CN | H | Cl | H | S |
| 11-101 | H | OH | F | H | O |
| 11-102 | H | CN | F | H | O |
| 11-103 | H | OH | Cl | H | O |
| 11-104 | H | CN | Cl | H | O |
| 11-105 | H | OH | Br | H | O |
| 11-106 | H | CN | Br | H | O |
| 11-107 | H | OH | CF$_3$ | H | O |
| 11-108 | H | CN | CF$_3$ | H | O |
| 11-109 | H | OH | OCH$_3$ | H | O |
| 11-110 | H | CN | OCH$_3$ | H | O |
| 11-111 | H | OH | CH$_3$ | H | O |
| 11-112 | H | CN | CH$_3$ | H | O |
| 11-113 | H | OH | F | 4-F | O |
| 11-114 | H | CN | F | 4-F | O |
| 11-115 | H | OH | Cl | 4-F | O |
| 11-116 | H | CN | Cl | 4-F | O |
| 11-117 | H | OH | Br | 4-F | O |
| 11-118 | H | CN | Br | 4-F | O |
| 11-119 | H | OH | CF$_3$ | 4-F | O |
| 11-120 | H | CN | CF$_3$ | 4-F | O |
| 11-121 | H | OH | OCH$_3$ | 4-F | O |
| 11-122 | H | CN | OCH$_3$ | 4-F | O |
| 11-123 | H | OH | CH$_3$ | 4-F | O |
| 11-124 | H | CN | CH$_3$ | 4-F | O |
| 11-125 | H | OH | F | 5-F | O |
| 11-126 | H | CN | F | 5-F | O |
| 11-127 | H | OH | Cl | 5-F | O |
| 11-128 | H | CN | Cl | 5-F | O |
| 11-129 | H | OH | Br | 5-F | O |
| 11-130 | H | CN | Br | 5-F | O |
| 11-131 | H | OH | CF$_3$ | 5-F | O |
| 11-132 | H | CN | CF$_3$ | 5-F | O |
| 11-133 | H | OH | OCH$_3$ | 5-F | O |
| 11-134 | H | CN | OCH$_3$ | 5-F | O |
| 11-135 | H | OH | CH$_3$ | 5-F | O |
| 11-136 | H | CN | CH$_3$ | 5-F | O |
| 11-137 | H | OH | F | 6-F | O |
| 11-138 | H | CN | F | 6-F | O |
| 11-139 | H | OH | Cl | 6-F | O |
| 11-140 | H | CN | Cl | 6-F | O |
| 11-141 | H | OH | Br | 6-F | O |
| 11-142 | H | CN | Br | 6-F | O |
| 11-143 | H | OH | CF$_3$ | 6-F | O |
| 11-144 | H | CN | CF$_3$ | 6-F | O |
| 11-145 | H | OH | OCH$_3$ | 6-F | O |
| 11-146 | H | CN | OCH$_3$ | 6-F | O |
| 11-147 | H | OH | CH$_3$ | 6-F | O |
| 11-148 | H | CN | CH$_3$ | 6-F | O |

$(R^{1b})_n$=H, $R^{1c}$=H, $R^2$=F, $(R^3)_m$=H and Z=O, and each value for R is described in Exhibit 2.

The present disclosure also includes Tables 11-2 through 11-148. Each Table is constructed in the same manner as Table 11-1 above, except that the row heading in Table 11-1 (i.e. "$(R^{1b})_n$=H, $R^{1c}$=H, $R^2$=F, $(R^3)_m$=H and Z=O") is replaced with the respective row heading shown below. For example, the first entry in Table 11-2 is a compound of Formula 1-11 wherein $(R^{1b})_n$ is F, $R^{1c}$=H, $R^2$ is F, $(R^3)_m$ is H and Z is O and R is butyl. Tables 11-3 through 11-148 are constructed similarly.

TABLE 12-1

1-12

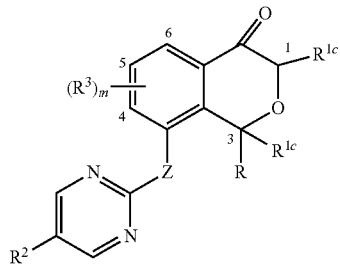

| Table | $R^{1c}$ | R² | $(R^3)_m$ | Z |
|---|---|---|---|---|
| | | Header Row | | |
| 12-2 | 1-F, 3-H | F | H | O |
| 12-3 | 1-OH, 3-H | F | H | O |
| 12-4 | 1-CN, 3-H | F | H | O |
| 12-5 | 1-H, 3-H | Cl | H | O |
| 12-6 | 1-F, 3-H | Cl | H | O |
| 12-7 | 1-OH, 3-H | Cl | H | O |
| 12-8 | 1-CN, 3-H | Cl | H | O |
| 12-9 | 1-H, 3-H | Br | H | O |
| 12-10 | 1-F, 3-H | Br | H | O |
| 12-11 | 1-OH, 3-H | Br | H | O |
| 12-12 | 1-CN, 3-H | Br | H | O |
| 12-13 | 1-H, 3-H | CF₃ | H | O |
| 12-14 | 1-F, 3-H | CF₃ | H | O |
| 12-15 | 1-OH, 3-H | CF₃ | H | O |
| 12-16 | 1-CN, 3-H | CF₃ | H | O |
| 12-17 | 1-H, 3-H | OCH₃ | H | O |
| 12-18 | 1-F, 3-H | OCH₃ | H | O |
| 12-19 | 1-OH, 3-H | OCH₃ | H | O |
| 12-20 | 1-CN, 3-H | OCH₃ | H | O |
| 12-21 | 1-H, 3-H | CH₃ | H | O |
| 12-22 | 1-F, 3-H | CH₃ | H | O |
| 12-23 | 1-OH, 3-H | CH₃ | H | O |
| 12-24 | 1-CN, 3-H | CH₃ | H | O |
| 12-25 | 1-H, 3-H | Cl | H | S |
| 12-26 | 1-H, 3-H | Cl | 4-F | O |
| 12-27 | 1-H, 3-H | Cl | 5-F | O |
| 12-28 | 1-H, 3-H | Cl | 6-F | O |
| 12-29 | 1-H, 3-F | F | H | O |
| 12-30 | 1-H, 3-OH | F | H | O |
| 12-31 | 1-H, 3-CN | F | H | O |
| 12-32 | 1-H, 3-F | Cl | H | O |
| 12-33 | 1-H, 3-OH | Cl | H | O |
| 12-34 | 1-H, 3-CN | Cl | H | O |
| 12-35 | 1-H, 3-F | Br | H | O |
| 12-36 | 1-H, 3-OH | Br | H | O |
| 12-37 | 1-H, 3-CN | Br | H | O |
| 12-38 | 1-H, 3-F | CF₃ | H | O |
| 12-39 | 1-H, 3-OH | CF₃ | H | O |
| 12-40 | 1-H, 3-CN | CF₃ | H | O |
| 12-41 | 1-H, 3-F | OCH₃ | H | O |
| 12-42 | 1-H, 3-OH | OCH₃ | H | O |
| 12-43 | 1-H, 3-CN | OCH₃ | H | O |
| 12-44 | 1-H, 3-F | CH₃ | H | O |
| 12-45 | 1-H, 3-OH | CH₃ | H | O |
| 12-46 | 1-H, 3-CN | CH₃ | H | O |

$R^{1c}$=1-H, 3-H, $R^2$=F, $(R^3)_m$=H and Z=O, and each value for R is described in Exhibit 2.

The present disclosure also includes Tables 12-2 through 12-46. Each Table is constructed in the same manner as Table 12-1 above, except that the row heading in Table 12-1 (i.e. "$R^{1c}$=1-H, 3-H, $R^2$=F, $(R^3)_m$=H and Z=O") is replaced with the respective row heading shown below. For example, the first entry in Table 12-2 is a compound of Formula 1-12 wherein $R^{1c}$=1-F, 3-H, $R^2$ is F, $(R^3)_m$ is H and Z is O and R is butyl. Tables 12-3 through 12-46 are constructed similarly.

TABLE 13-1

1-13

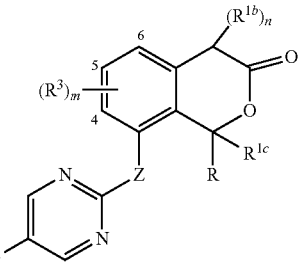

| Table | $R^{1c}$ | $(R^{1b})_n$ | R² | $(R^3)_m$ | Z |
|---|---|---|---|---|---|
| | | Header Row | | | |
| 13-2 | F | H | F | H | O |
| 13-3 | OH | H | F | H | O |
| 13-4 | CN | H | F | H | O |
| 13-5 | H | H | Cl | H | O |
| 13-6 | F | H | Cl | H | O |
| 13-7 | OH | H | Cl | H | O |
| 13-8 | CN | H | Cl | H | O |
| 13-9 | H | H | Br | H | O |
| 13-10 | F | H | Br | H | O |
| 13-11 | OH | H | Br | H | O |
| 13-12 | CN | H | Br | H | O |
| 13-13 | H | H | CF₃ | H | O |
| 13-14 | F | H | CF₃ | H | O |
| 13-15 | OH | H | CF₃ | H | O |
| 13-16 | CN | H | CF₃ | H | O |
| 13-17 | H | H | OCH₃ | H | O |
| 13-18 | F | H | OCH₃ | H | O |
| 13-19 | OH | H | OCH₃ | H | O |
| 13-20 | CN | H | OCH₃ | H | O |
| 13-21 | H | H | CH₃ | H | O |
| 13-22 | F | H | CH₃ | H | O |
| 13-23 | OH | H | CH₃ | H | O |
| 13-24 | CN | H | CH₃ | H | O |
| 13-25 | H | H | Cl | H | S |
| 13-26 | H | OH | F | H | O |
| 13-27 | F | OH | F | H | O |
| 13-28 | OH | OH | F | H | O |
| 13-29 | CN | OH | F | H | O |
| 13-30 | H | OH | Cl | H | O |
| 13-31 | F | OH | Cl | H | O |
| 13-32 | OH | OH | Cl | H | O |
| 13-33 | CN | OH | Cl | H | O |
| 13-34 | H | OH | Br | H | O |
| 13-35 | F | OH | Br | H | O |
| 13-36 | OH | OH | Br | H | O |
| 13-37 | CN | OH | Br | H | O |
| 13-38 | H | OH | CF₃ | H | O |
| 13-39 | F | OH | CF₃ | H | O |
| 13-40 | OH | OH | CF₃ | H | O |
| 13-41 | CN | OH | CF₃ | H | O |
| 13-42 | H | OH | OCH₃ | H | O |
| 13-43 | F | OH | OCH₃ | H | O |
| 13-44 | OH | OH | OCH₃ | H | O |
| 13-45 | CN | OH | OCH₃ | H | O |
| 13-46 | H | OH | CH₃ | H | O |
| 13-47 | F | OH | CH₃ | H | O |
| 13-48 | OH | OH | CH₃ | H | O |
| 13-49 | CN | OH | CH₃ | H | O |
| 13-50 | H | OH | Cl | H | S |
| 13-51 | F | OH | Cl | H | S |
| 13-52 | OH | OH | Cl | H | S |
| 13-53 | CN | OH | Cl | H | S |
| 13-54 | H | CN | F | H | O |
| 13-55 | F | CN | F | H | O |
| 13-56 | OH | CN | F | H | O |
| 13-57 | CN | CN | F | H | O |
| 13-58 | H | CN | Cl | H | O |
| 13-59 | F | CN | Cl | H | O |
| 13-60 | OH | CN | Cl | H | O |
| 13-61 | CN | CN | Cl | H | O |
| 13-62 | H | CN | Br | H | O |

TABLE 13-1-continued

| | | | | | |
|---|---|---|---|---|---|
| 13-63 | F | CN | Br | H | S |
| 13-64 | OH | CN | Br | H | S |
| 13-65 | CN | CN | Br | H | S |
| 13-66 | H | CN | $CF_3$ | H | S |
| 13-67 | F | CN | $CF_3$ | H | O |
| 13-68 | OH | CN | $CF_3$ | H | O |
| 13-69 | CN | CN | $CF_3$ | H | O |
| 13-70 | H | CN | $OCH_3$ | H | O |
| 13-71 | F | CN | $OCH_3$ | H | O |
| 13-72 | OH | CN | $OCH_3$ | H | O |
| 13-73 | CN | CN | $OCH_3$ | H | O |
| 13-74 | H | CN | $CH_3$ | H | O |
| 13-75 | F | CN | $CH_3$ | H | O |
| 13-76 | OH | CN | $CH_3$ | H | O |
| 13-77 | CN | CN | $CH_3$ | H | O |
| 13-78 | H | H | Cl | 4-F | O |
| 13-79 | H | H | Cl | 5-F | O |
| 13-80 | H | H | Cl | 6-F | O |

$R^{1c}$=H, $(R^{1b})_n$=H, $R^2$=F, $(R^3)_m$=H and Z=O, and each value for R is described in Exhibit 2.

The present disclosure also includes Tables 13-2 through 13-80. Each Table is constructed in the same manner as Table 13-1 above, except that the row heading in Table 13-1 (i.e. "$R^{1c}$=H, $(R^{1b})_n$=H, $R^2$=F, $(R^3)_m$=H and Z=O") is replaced with the respective row heading shown below. For example, the first entry in Table 13-2 is a compound of Formula 1-13 wherein $R^{1c}$ is F, $(R^{1b})_n$=H, $R^2$ is F, $(R^3)_m$ is H and Z is O and R is butyl. Tables 13-3 through 13-80 are constructed similarly.

TABLE 14-1

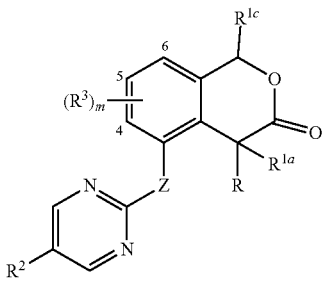

1-14

| | Header Row | | | | |
|---|---|---|---|---|---|
| Table | $R^{1a}$ | $R^{1c}$ | $R^2$ | $(R^3)_m$ | Z |
| 14-2 | F | H | F | H | O |
| 14-3 | OH | H | F | H | O |
| 14-4 | CN | H | F | H | O |
| 14-5 | H | H | Cl | H | O |
| 14-6 | F | H | Cl | H | O |
| 14-7 | OH | H | Cl | H | O |
| 14-8 | CN | H | Cl | H | O |
| 14-9 | H | H | Br | H | O |
| 14-10 | F | H | Br | H | O |
| 14-11 | OH | H | Br | H | O |
| 14-12 | CN | H | Br | H | O |
| 14-13 | H | H | $CF_3$ | H | O |
| 14-14 | F | H | $CF_3$ | H | O |
| 14-15 | OH | H | $CF_3$ | H | O |
| 14-16 | CN | H | $CF_3$ | H | O |
| 14-17 | H | H | $OCH_3$ | H | O |
| 14-18 | F | H | $OCH_3$ | H | O |
| 14-19 | OH | H | $OCH_3$ | H | O |
| 14-20 | CN | H | $OCH_3$ | H | O |
| 14-21 | H | H | $CH_3$ | H | O |
| 14-22 | F | H | $CH_3$ | H | O |
| 14-23 | OH | H | $CH_3$ | H | O |
| 14-24 | CN | H | $CH_3$ | H | O |
| 14-25 | H | H | F | 4-F | O |

TABLE 14-1-continued

| | | | | | |
|---|---|---|---|---|---|
| 14-26 | F | H | F | 4-F | O |
| 14-27 | OH | H | F | 4-F | O |
| 14-28 | CN | H | F | 4-F | O |
| 14-29 | H | H | Cl | 4-F | O |
| 14-30 | F | H | Cl | 4-F | O |
| 14-31 | OH | H | Cl | 4-F | O |
| 14-32 | CN | H | Cl | 4-F | O |
| 14-33 | H | H | Br | 4-F | O |
| 14-34 | F | H | Br | 4-F | O |
| 14-35 | OH | H | Br | 4-F | O |
| 14-36 | CN | H | Br | 4-F | O |
| 14-37 | H | H | $CF_3$ | 4-F | O |
| 14-38 | F | H | $CF_3$ | 4-F | O |
| 14-39 | OH | H | $CF_3$ | 4-F | O |
| 14-40 | CN | H | $CF_3$ | 4-F | O |
| 14-41 | H | H | $OCH_3$ | 4-F | O |
| 14-42 | F | H | $OCH_3$ | 4-F | O |
| 14-43 | OH | H | $OCH_3$ | 4-F | O |
| 14-44 | CN | H | $OCH_3$ | 4-F | O |
| 14-45 | H | H | $CH_3$ | 4-F | O |
| 14-46 | F | H | $CH_3$ | 4-F | O |
| 14-47 | OH | H | $CH_3$ | 4-F | O |
| 14-48 | CN | H | $CH_3$ | 4-F | O |
| 14-49 | H | H | F | 5-F | O |
| 14-50 | F | H | F | 5-F | O |
| 14-51 | OH | H | F | 5-F | O |
| 14-52 | CN | H | F | 5-F | O |
| 14-53 | H | H | Cl | 5-F | O |
| 14-54 | F | H | Cl | 5-F | O |
| 14-55 | OH | H | Cl | 5-F | O |
| 14-56 | CN | H | Cl | 5-F | O |
| 14-57 | H | H | Br | 5-F | O |
| 14-58 | F | H | Br | 5-F | O |
| 14-59 | OH | H | Br | 5-F | O |
| 14-60 | CN | H | Br | 5-F | O |
| 14-61 | H | H | $CF_3$ | 5-F | O |
| 14-62 | F | H | $CF_3$ | 5-F | O |
| 14-63 | OH | H | $CF_3$ | 5-F | O |
| 14-64 | CN | H | $CF_3$ | 5-F | O |
| 14-65 | H | H | $OCH_3$ | 5-F | O |
| 14-66 | F | H | $OCH_3$ | 5-F | O |
| 14-67 | OH | H | $OCH_3$ | 5-F | O |
| 14-68 | CN | H | $OCH_3$ | 5-F | O |
| 14-69 | H | H | $CH_3$ | 5-F | O |
| 14-70 | F | H | $CH_3$ | 5-F | O |
| 14-71 | OH | H | $CH_3$ | 5-F | O |
| 14-72 | CN | H | $CH_3$ | 5-F | O |
| 14-73 | H | H | F | 6-F | O |
| 14-74 | F | H | F | 6-F | O |
| 14-75 | OH | H | F | 6-F | O |
| 14-76 | CN | H | F | 6-F | O |
| 14-77 | H | H | Cl | 6-F | O |
| 14-78 | F | H | Cl | 6-F | O |
| 14-79 | OH | H | Cl | 6-F | O |
| 14-80 | CN | H | Cl | 6-F | O |
| 14-81 | H | H | Br | 6-F | O |
| 14-82 | F | H | Br | 6-F | O |
| 14-83 | OH | H | Br | 6-F | O |
| 14-84 | CN | H | Br | 6-F | O |
| 14-85 | H | H | $CF_3$ | 6-F | O |
| 14-86 | F | H | $CF_3$ | 6-F | O |
| 14-87 | OH | H | $CF_3$ | 6-F | O |
| 14-88 | CN | H | $CF_3$ | 6-F | O |
| 14-89 | H | H | $OCH_3$ | 6-F | O |
| 14-90 | F | H | $OCH_3$ | 6-F | O |
| 14-91 | OH | H | $OCH_3$ | 6-F | O |
| 14-92 | CN | H | $OCH_3$ | 6-F | O |
| 14-93 | H | H | $CH_3$ | 6-F | O |
| 14-94 | F | H | $CH_3$ | 6-F | O |
| 14-95 | OH | H | $CH_3$ | 6-F | O |
| 14-96 | CN | H | $CH_3$ | 6-F | O |
| 14-97 | H | H | Cl | H | S |
| 14-98 | F | H | Cl | H | S |
| 14-99 | OH | H | Cl | H | S |
| 14-100 | CN | H | Cl | H | S |
| 14-101 | H | OH | F | H | O |
| 14-102 | H | CN | F | H | O |
| 14-103 | H | OH | Cl | H | O |
| 14-104 | H | CN | Cl | H | O |
| 14-105 | H | OH | Br | H | O |

TABLE 14-1-continued

| | | | | |
|---|---|---|---|---|
| 14-106 | H | CN | Br | H | O |
| 14-107 | H | OH | CF$_3$ | H | O |
| 14-108 | H | CN | CF$_3$ | H | O |
| 14-109 | H | OH | OCH$_3$ | H | O |
| 14-110 | H | CN | OCH$_3$ | H | O |
| 14-111 | H | OH | CH$_3$ | H | O |
| 14-112 | H | CN | CH$_3$ | H | O |
| 14-113 | H | OH | F | 4-F | O |
| 14-114 | H | CN | F | 4-F | O |
| 14-115 | H | OH | Cl | 4-F | O |
| 14-116 | H | CN | Cl | 4-F | O |
| 14-117 | H | OH | Br | 4-F | O |
| 14-118 | H | CN | Br | 4-F | O |
| 14-119 | H | OH | CF$_3$ | 4-F | O |
| 14-120 | H | CN | CF$_3$ | 4-F | O |
| 14-121 | H | OH | OCH$_3$ | 4-F | O |
| 14-122 | H | CN | OCH$_3$ | 4-F | O |
| 14-123 | H | OH | CH$_3$ | 4-F | O |
| 14-124 | H | CN | CH$_3$ | 4-F | O |
| 14-125 | H | OH | F | 5-F | O |
| 14-126 | H | CN | F | 5-F | O |
| 14-127 | H | OH | Cl | 5-F | O |
| 14-128 | H | CN | Cl | 5-F | O |
| 14-129 | H | OH | Br | 5-F | O |
| 14-130 | H | CN | Br | 5-F | O |
| 14-131 | H | OH | CF$_3$ | 5-F | O |
| 14-132 | H | CN | CF$_3$ | 5-F | O |
| 14-133 | H | OH | OCH$_3$ | 5-F | O |
| 14-134 | H | CN | OCH$_3$ | 5-F | O |
| 14-135 | H | OH | CH$_3$ | 5-F | O |
| 14-136 | H | CN | CH$_3$ | 5-F | O |
| 14-137 | H | OH | F | 6-F | O |
| 14-138 | H | CN | F | 6-F | O |
| 14-139 | H | OH | Cl | 6-F | O |
| 14-140 | H | CN | Cl | 6-F | O |
| 14-141 | H | OH | Br | 6-F | O |
| 14-142 | H | CN | Br | 6-F | O |
| 14-143 | H | OH | CF$_3$ | 6-F | O |
| 14-144 | H | CN | CF$_3$ | 6-F | O |
| 14-145 | H | OH | OCH$_3$ | 6-F | O |
| 14-146 | H | CN | OCH$_3$ | 6-F | O |
| 14-147 | H | OH | CH$_3$ | 6-F | O |
| 14-148 | H | CN | CH$_3$ | 6-F | O |

$R^{1a}$=H, $R^{1c}$=H, $R^2$=F, $(R^3)_m$=H and Z=O, and each value for R is described in Exhibit 2.

The present disclosure also includes Tables 14-2 through 14-148. Each Table is constructed in the same manner as Table 14-1 above, except that the row heading in Table 14-1 (i.e. "$R^{1a}$=H, $R^{1c}$=H, $R^2$=F, $(R^3)_m$=H and Z=O") is replaced with the respective row heading shown below. For example, the first entry in Table 14-2 is a compound of Formula 1-14 wherein $R^{1a}$ is F, $R^{1c}$=H, $R^2$ is F, $(R^3)_m$ is H and Z is O and R is butyl. Tables 14-3 through 14-148 are constructed similarly.

TABLE 15-1

1-15

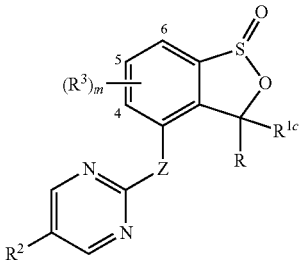

| Table | $R^{1c}$ | $R^2$ | $(R^3)_m$ | Z |
|---|---|---|---|---|
| 15-2 | F | F | H | O |
| 15-3 | OH | F | H | O |
| 15-4 | CN | F | H | O |
| 15-5 | H | Cl | H | O |
| 15-6 | F | Cl | H | O |
| 15-7 | OH | Cl | H | O |
| 15-8 | CN | Cl | H | O |
| 15-9 | H | Br | H | O |
| 15-10 | F | Br | H | O |
| 15-11 | OH | Br | H | O |
| 15-12 | CN | Br | H | O |
| 15-13 | H | CF$_3$ | H | O |
| 15-14 | F | CF$_3$ | H | O |
| 15-15 | OH | CF$_3$ | H | O |
| 15-16 | CN | CF$_3$ | H | O |
| 15-17 | H | OCH$_3$ | H | O |
| 15-18 | F | OCH$_3$ | H | O |
| 15-19 | OH | OCH$_3$ | H | O |
| 15-20 | CN | OCH$_3$ | H | O |
| 15-21 | H | CH$_3$ | H | O |
| 15-22 | F | CH$_3$ | H | O |
| 15-23 | OH | CH$_3$ | H | O |
| 15-24 | CN | CH$_3$ | H | O |
| 15-25 | H | F | 4-F | O |
| 15-26 | F | F | 4-F | O |
| 15-27 | OH | F | 4-F | O |
| 15-28 | CN | F | 4-F | O |
| 15-29 | H | Cl | 4-F | O |
| 15-30 | F | Cl | 4-F | O |
| 15-31 | OH | Cl | 4-F | O |
| 15-32 | CN | Cl | 4-F | O |
| 15-33 | H | Br | 4-F | O |
| 15-34 | F | Br | 4-F | O |
| 15-35 | OH | Br | 4-F | O |
| 15-36 | CN | Br | 4-F | O |
| 15-37 | H | CF$_3$ | 4-F | O |
| 15-38 | F | CF$_3$ | 4-F | O |
| 15-39 | OH | CF$_3$ | 4-F | O |
| 15-40 | CN | CF$_3$ | 4-F | O |
| 15-41 | H | OCH$_3$ | 4-F | O |
| 15-42 | F | OCH$_3$ | 4-F | O |
| 15-43 | OH | OCH$_3$ | 4-F | O |
| 15-44 | CN | OCH$_3$ | 4-F | O |
| 15-45 | H | CH$_3$ | 4-F | O |
| 15-46 | F | CH$_3$ | 4-F | O |
| 15-47 | OH | CH$_3$ | 4-F | O |
| 15-48 | CN | CH$_3$ | 4-F | O |
| 15-49 | H | F | 5-F | O |
| 15-50 | F | F | 5-F | O |
| 15-51 | OH | F | 5-F | O |
| 15-52 | CN | F | 5-F | O |
| 15-53 | H | Cl | 5-F | O |
| 15-54 | F | Cl | 5-F | O |
| 15-55 | OH | Cl | 5-F | O |
| 15-56 | CN | Cl | 5-F | O |
| 15-57 | H | Br | 5-F | O |
| 15-58 | F | Br | 5-F | O |
| 15-59 | OH | Br | 5-F | O |
| 15-60 | CN | Br | 5-F | O |
| 15-61 | H | CF$_3$ | 5-F | O |
| 15-62 | F | CF$_3$ | 5-F | O |

TABLE 15-1-continued

| | | | | |
|---|---|---|---|---|
| 15-63 | OH | $CF_3$ | 5-F | O |
| 15-64 | CN | $CF_3$ | 5-F | O |
| 15-65 | H | $OCH_3$ | 5-F | O |
| 15-66 | F | $OCH_3$ | 5-F | O |
| 15-67 | OH | $OCH_3$ | 5-F | O |
| 15-68 | CN | $OCH_3$ | 5-F | O |
| 15-69 | H | $CH_3$ | 5-F | O |
| 15-70 | F | $CH_3$ | 5-F | O |
| 15-71 | OH | $CH_3$ | 5-F | O |
| 15-72 | CN | $CH_3$ | 5-F | O |
| 15-73 | H | F | 6-F | O |
| 15-74 | F | F | 6-F | O |
| 15-75 | OH | F | 6-F | O |
| 15-76 | CN | F | 6-F | O |
| 15-77 | H | Cl | 6-F | O |
| 15-78 | F | Cl | 6-F | O |
| 15-79 | OH | Cl | 6-F | O |
| 15-80 | CN | Cl | 6-F | O |
| 15-81 | H | Br | 6-F | O |
| 15-82 | F | Br | 6-F | O |
| 15-83 | OH | Br | 6-F | O |
| 15-84 | CN | Br | 6-F | O |
| 15-85 | H | $CF_3$ | 6-F | O |
| 15-86 | F | $CF_3$ | 6-F | O |
| 15-87 | OH | $CF_3$ | 6-F | O |
| 15-88 | CN | $CF_3$ | 6-F | O |
| 15-89 | H | $OCH_3$ | 6-F | S |
| 15-90 | F | $OCH_3$ | 6-F | S |
| 15-91 | OH | $OCH_3$ | 6-F | S |
| 15-92 | CN | $OCH_3$ | 6-F | S |
| 15-93 | H | $CH_3$ | 6-F | O |
| 15-94 | F | $CH_3$ | 6-F | O |
| 15-95 | OH | $CH_3$ | 6-F | O |
| 15-96 | CN | $CH_3$ | 6-F | O |
| 15-97 | H | Cl | H | S |
| 15-98 | F | Cl | H | S |
| 15-99 | OH | Cl | H | S |
| 15-100 | CN | Cl | H | S |
| 15-101 | Me | Cl | H | O |
| 15-102 | OMe | Cl | H | O |
| 15-103 | $OCHF_2$ | Cl | H | O |
| 15-104 | $OCF_3$ | Cl | H | O |
| 15-105 | $CF_3$ | Cl | H | O |

$R^{1c}$=H, $R^2$=F, $(R^3)_m$=H and Z=O, and each value for R is described in Exhibit 2.

The present disclosure also includes Tables 15-2 through 15-105. Each Table is constructed in the same manner as Table 15-1 above, except that the row heading in Table 15-1 (i.e. "$R^{1c}$=H, $R^2$=F, $(R^3)_m$=H and Z=O") is replaced with the respective row heading shown below. For example, the first entry in Table 15-2 is a compound of Formula 1-15 wherein $R^{1c}$ is F, $R^2$ is F, $(R^3)_m$ is H and Z is O and R is butyl. Tables 15-3 through 15-105 are constructed similarly.

A compound of this disclosure will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present disclosure often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this disclosure may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials,* annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present disclosure to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C (i) Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35" and "Compound 36".

Test results indicate that the compounds of the present disclosure are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this disclosure, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this disclosure may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this disclosure can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the disclosure have both preemergent and postemergent herbicidal activity, to control undesired vegetation by killing or injuring the vegetation or reducing its growth, the compounds can be usefully applied by a variety of methods involving contacting a herbicidally effective amount of a compound of the disclosure, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass, Benghal dayflower, blackgrass, black nightshade, broadleaf signalgrass, Canada thistle, cheat, common cocklebur (*Xanthium pensylvanicum*), common ragweed, corn poppies, field violet, giant foxtail, goosegrass, green foxtail, guinea grass, hairy beggarticks, herbicide-resistant black grass, horseweed, Italian rye grass, jimsonweed, Johnson grass (*Sorghum halepense*), large crabgrass, little seed canary grass, morning glory, Pennsylvania smartweed, pitted morning glory, prickly sida, quackgrass, redroot pigweed, shattercane, shepherd's purse, silky windgrass, sunflower (as weed in potato), wild buckwheat (*Polygonum convolvulus*), wild mustard (*Brassica kaber*), wild oat (*Avena fatua*), wild pointsettia, yellow foxtail, and yellow nutsedge (*Cyperus esculentus*).

A herbicidally effective amount of the compounds of this disclosure is determined by a number of factors. These factors include: formulation selected, method of application, amount and type of vegetation present, growing conditions, etc. In general, a herbicidally effective amount of compounds of this disclosure is about 0.001 to 20 kg/ha with a preferred range of about 0.004 to 1 kg/ha. One skilled in the art can easily determine the herbicidally effective amount necessary for the desired level of weed control.

In one common embodiment, a compound of the disclosure is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the disclosure can be directly applied to a plant or a part thereof, particularly of the undesired vegetation, and/or to the growth medium in contact with the plant.

Plant varieties and cultivars of the desired vegetation in the locus treated with a compound of the disclosure can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the disclosure include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
| --- | --- |
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
| --- | --- | --- | --- | --- |
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |

-continued

| Crop | Event Name | Event Code | Trait(s) | Gene(s) |
|---|---|---|---|---|
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | FI117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |

| Crop | Event Name | Event Code | Trait(s) | Gene(s) |
| --- | --- | --- | --- | --- |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |

-continued

| Crop | Event Name | Event Code | Trait(s) | Gene(s) |
| --- | --- | --- | --- | --- |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the disclosure are used to control undesired vegetation, contact of desired vegetation in the treated locus with compounds of the disclosure may result in super-additive or enhanced effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

An embodiment of the present disclosure is a method for controlling the growth of undesired vegetation in genetically modified plants that exhibit traits of glyphosate tolerance, glufosinate tolerance, ALS herbicide tolerance, dicamba tolerance, imidazolinone herbicide tolerance, 2,4-D tolerance, HPPD tolerance and mesotrione tolerance, comprising contacting the vegetation or its environment with a herbicidally effective amount of a compound of Formula 1.

Compounds of this disclosure can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the disclosure with other herbicides can broaden the spectrum of activity against additional weed species, and suppress the proliferation of any resistant biotypes. Thus the present disclosure also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present disclosure, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this disclosure may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron- TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this disclosure can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this disclosure with other biologically active (particularly herbicidal) compounds or agents (i.e. active ingredients) can result in a greater-than-additive (i.e. enhanced) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When the enhanced effects of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the disclosure with at least one other herbicidal active ingredient. Of particular note is such a combination where the other herbicidal active ingredient has different site of action from the compound of the disclosure. In certain instances, a combination with at least one other herbicidal active ingredient having a similar spectrum of control but a different site of action will be particularly advantageous for resistance management. Thus, a composition of the present disclosure can further comprise (in a herbicidally effective amount) at least one additional herbicidal active ingredient having a similar spectrum of control but a different site of action.

Compounds of this disclosure can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this disclosure, or applied as seed treatments. Therefore an aspect of the present disclosure relates to a herbicidal mixture comprising a compound of this disclosure and an antidotally effective amount of a herbicide safener. Seed treatment is particularly useful for selective weed control, because it physically restricts antidoting to the crop plants. Therefore a particularly useful embodiment of the present disclosure is a method for selectively controlling the growth of undesired vegetation in a crop comprising contacting the locus of the crop with a herbicidally effective amount of a compound of this disclosure wherein seed from which the crop is grown is treated with an antidotally effective amount of safener. Antidotally effective amounts of safeners can be easily determined by one skilled in the art through simple experimentation.

Compounds of the disclosure cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the disclosure (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from enhanced effects, broader spectrum of weeds controlled, or enhanced crop safety) or for preventing the development of resistant weeds are mixtures of a compound of this disclosure with a herbicide selected from the group 2,4-D, acetochlor, alachlor, atrazine, bromoxynil, bentazon, bicyclopyrone, carfentrazone-ethyl, cloransulam-methyl, dicamba, dimethenamid-p, florasulam, flufenacet, flumioxazin, flupyrsulfuron-methyl, fluroxypyr-meptyl, glyphosate, halauxifen-methyl, isoxaflutole, MCPA, mesotrione, metolachlor, metsulfuron-methyl, nicosulfuron, pyrasulfotole, pyroxasulfone, pyroxsulam, rimsulfuron, saflufenacil, tembotrione, thifensulfuron-methyl, topramazone and tribenuron.

Table A1 lists specific combinations of a Component (a) with Component (b) illustrative of the mixtures, compositions and methods of the present disclosure. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound 1) | Component (b) | Typical Weight Ratio | More Typical Weight Ratio | Most Typical Weight Ratio |
| --- | --- | --- | --- | --- |
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |

TABLE A1-continued

| Component (a) (Compound 1) | Component (b) | Typical Weight Ratio | More Typical Weight Ratio | Most Typical Weight Ratio |
|---|---|---|---|---|
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |

TABLE A1-continued

| Component (a) (Compound 1) | Component (b) | Typical Weight Ratio | More Typical Weight Ratio | Most Typical Weight Ratio |
|---|---|---|---|---|
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |

TABLE A1-continued

| Component (a) (Compound 1) | Component (b) | Typical Weight Ratio | More Typical Weight Ratio | Most Typical Weight Ratio |
|---|---|---|---|---|
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A15 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |

-continued

| Table Number | Component (a) Column Entries |
|---|---|
| A19 | Compound 19 |
| A20 | Compound 20 |
| A21 | Compound 21 |
| A22 | Compound 22 |
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |

The compounds of the present disclosure are useful for the control of weed species that are resistant to herbicides with the AHAS-inhibitor or (b2) [chemical compound that inhibits acetohydroxy acid synthase (AHAS), also known as acetolactate synthase (ALS)] mode of action.

The following Tests demonstrate the control efficacy of the compounds of this disclosure against specific weeds. The weed control afforded by the compounds is not limited, however, to these species. See Index Tables A-C for compound descriptions. The abbreviation "Cmpd. No." stands for "Compound Number". The abbreviation "Ex." stands for "Example" and is followed by a number indicating in which example the compound is prepared. Mass spectra are reported with an estimated precision within ±0.5 Da as the molecular weight of the highest isotopic abundance parent ion (M+1) formed by addition of H$^+$ (molecular weight of 1) to the molecule or (M−1) formed by the loss of H+ (molecular weight of 1) from the molecule. The presence of molecular ions containing one or more higher atomic weight isotopes of lower abundance (e.g., $^{37}$Cl, $^{81}$Br) is not reported. The alternate molecular ion peaks (e.g., M+2 or M+4) that occur with compounds containing multiple halogens are not reported. The reported M+1 peaks were observed by mass spectrometry using atmospheric pressure chemical ionization (AP$^+$) or electrospray ionization (ES$^+$).

INDEX TABLE A

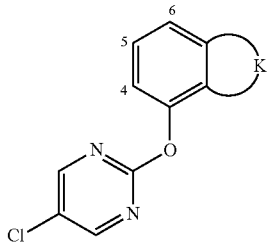

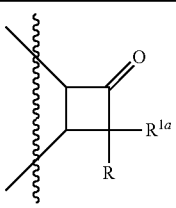

INDEX TABLE A-continued

INDEX TABLE A-continued

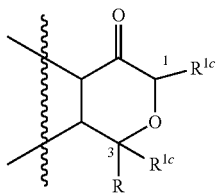 K-12

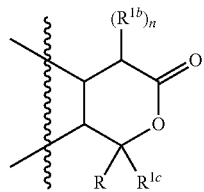 K-13

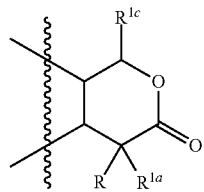 K-14

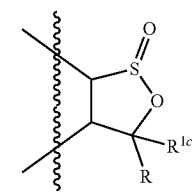 K-15

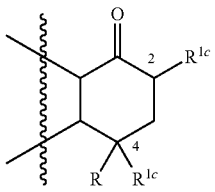 K-16

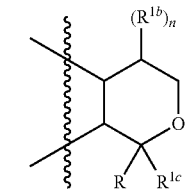 K-17

INDEX TABLE A*

| Cmpd No | K | R | $(R^{1b})_n$ | $R^{1c}$ | $R^{1a}$ or $R^4$ | MP (° C.) | MS (AP+) or (ES+) |
|---|---|---|---|---|---|---|---|
| 1 (Ex. 3) | K-7 | —CH$_2$CH$_2$CH$_2$CF$_3$ | — | H | — | | 373* |
| 2** | K-7 | —CH$_2$CH$_2$CH$_2$CF$_3$ | — | H | — | | 373 |
| 3** | K-7 | —CH$_2$CH$_2$CH$_2$CF$_3$ | — | H | — | | 373 |
| 4 | K-7 | —CH$_2$CH$_2$CF$_3$ | — | H | — | | 359 |
| 5 | K-12 | —CH$_2$CH$_2$CH$_2$CF$_3$ | — | 1-H, 3-H | — | | 387 |
| 6 (Ex. 2) | K-3 | —CH$_2$CH$_2$CH$_2$CF$_3$ | H | H | — | | 371 |
| 7 (Ex. 1) | K-5 | —CH$_2$CH$_2$CH$_2$CF$_3$ | — | 1-H, 3-H | — | | 359 |
| 8 | K-5 | —CH$_2$CH$_2$CF$_3$ | — | 1-H, 3-H | — | | 345 |
| 9 | K-2 | —CH$_2$CH$_2$CH$_2$CF$_3$ | 1-H, 2-H | — | $R^{1a}$=H | | 357 |
| 10 | K-2 | —CH$_2$CH$_2$CH$_2$CF$_3$ | 1-OH, 2-H | — | $R^{1a}$=H | | 373 |
| 11 | K-3 | —CH$_2$CH$_2$CF$_3$ | H | H | — | | 357 |
| 12 | K-9 | —CH$_2$CH$_2$CH$_2$CF$_3$ | — | H | $R^4$=CH$_3$ | | 386 |
| 13 | K-9 | —CH$_2$CH$_2$CH$_2$CF$_3$ | — | H | $R^4$=H | | 372 |
| 14 | K-2 | —CH$_2$CH$_2$CF$_3$ | 1-H, 2-H | — | $R^{1a}$=OH | | *** |
| 15 | K-15 | —CH$_2$CH$_2$CH$_2$CF$_3$ | — | H | — | | 339 |
| 16 | K-10 | —CH$_2$CH$_2$CH$_2$CF$_3$ | — | H | $R^{1a}$=H | | 387 |
| 17 | K-13 | —CH$_2$CH$_2$CH$_2$CF$_3$ | H | H | — | 125-129 | 387 |
| 18** | K-7 | —CH$_2$CH$_2$CF$_3$ | — | H | — | 99-101 | 359 |
| 19** | K-7 | —CH$_2$CH$_2$CF$_3$ | — | H | — | 94-99 | 359 |
| 20** | K-5 | —CH$_2$CH$_2$CF$_3$ | — | 1-H, 3-H | — | | 345 |
| 21** | K-5 | —CH$_2$CH$_2$CF$_3$ | — | 1-H, 3-H | — | | 345 |
| 22 | K-1 | —CH$_2$CH$_2$CH$_2$CF$_3$ | — | — | $R^{1a}$=H | | 357 |
| 23 | K-11 | —CH$_2$CH$_2$CF$_3$ | H | H | — | 117-121 | 373 |
| 24 | K-1 | —CH$_2$CH$_2$CF$_3$ | — | — | $R^{1a}$=H | | 343 |
| 25 | K-10 | —CH$_2$CH$_2$CF$_3$ | — | H | $R^{1a}$=H | | 373 |
| 26 | K-14 | —CH$_2$CH$_2$CH$_2$CF$_3$ | — | H | $R^{1a}$=H | | 387 |
| 27 | K-17 | —CH$_2$CH$_2$CH$_2$CF$_3$ | — | H | — | | 373 |
| 28 | K-13 | —CH$_2$CH$_2$CF$_3$ | H | H | — | 122-126 | 373 |
| 29 | K-14 | —CH$_2$CH$_2$CF$_3$ | — | H | $R^{1a}$=H | | 373 |
| 30 | K-16 | —CH$_2$CH$_2$CH$_2$CF$_3$ | — | 2-H, 4-H | — | | 385 |
| 31 | K-11 | —CH$_2$CH$_2$CH$_2$CH$_2$CF$_3$ | H | H | — | 93-97 | 401 |
| 32 | K-17 | —CH$_2$CH$_2$CF$_3$ | H | H | — | | 359 |
| 33 | K-6 | —CH$_2$CH$_2$CH$_2$CF$_3$ | — | H | $R^{1a}$=H | | 359 |
| 34 | K-14 | —CH$_2$CH$_2$CH$_2$CH$_2$CF$_3$ | — | H | $R^{1a}$=H | | 401 |
| 35 | K-13 | —CH$_2$CH$_2$CH$_3$ | H | H | — | 136-140 | 319 |
| 36 | K-6 | —CH$_2$CH$_2$CF$_3$ | — | H | $R^{1a}$=H | | 345 |

*All compounds are reported as mixtures of enantiomers, unless otherwise indicated.
**Indicates the compound is prepared enantio-enriched.
*** See Index Table B for 1H NMR data.

INDEX TABLE B

| Cmpd | ¹H NMR (CDCl₃ solution unless indicated otherwise) |
|---|---|
| 1 | δ 8.51-8.55 (m, 2H), 7.81-7.87 (m, 1H), 7.61-7.64 (m, 1H), 7.47-7.48 (m, 1H), 5.49-5.51 (m, 1H), 2.17-2.25 (m, 1H), 1.98-2.13 (m, 2H), 1.72-1.81 (m, 1H), 1.61-1.70 (m, 2H). |
| 14 | δ 8.50 (s, 2H), 7.31-7.37 (m, 1H), 7.17-7.21 (m, 1H), 6.93-6.98 (m, 1H), 3.07-3.16 (m, 1H), 2.86-2.95 (m, 1H), 2.74 (s, 1H), 2.14-2.28 (m, 5H), 1.98-2.04 (m, 1H). |

¹H NMR data are in ppm downfield from tetramethylsilane. Couplings are designated by (s)—singlet, (d)—doublet, (t)—triplet, (m)—multiplet, (dd)—doublet of doublets, (dt)—doublet of triplets, (br s)—broad singlet

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), foxtail, giant (giant foxtail, *Setaria faberii*), foxtail, green (green foxtail, *Setaria viridis*) and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| | Compounds | | |
|---|---|---|---|
| 500 g ai/ha Postemergence | 1 | 14 | 15 |
| Barnyardgrass | 80 | 80 | 60 |
| Blackgrass | 100 | 90 | 90 |
| Corn | 60 | 40 | 40 |
| Foxtail, Green | 100 | 50 | 80 |
| Galium | 100 | 90 | 80 |
| Kochia | 100 | 80 | 90 |
| Pigweed | 100 | 100 | 90 |
| Ragweed | 40 | 90 | 60 |
| Ryegrass, Italian | 80 | 90 | 90 |
| Wheat | 80 | 60 | 30 |

| 125 g ai/ha Postemergence | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Barnyardgrass | 70 | 0 | 90 | 90 | 10 | 40 | 60 | 50 | 50 | 40 | 30 | 0 | 0 | 30 |
| Blackgrass | 40 | 0 | 100 | 90 | 10 | 30 | 70 | 100 | 80 | 20 | 20 | 0 | 0 | 40 |
| Corn | 40 | 10 | 80 | 80 | 10 | 20 | 40 | 50 | 30 | 30 | 10 | 10 | 0 | 10 |
| Foxtail, Giant | — | — | — | — | — | — | — | — | — | — | — | — | — | — |
| Foxtail, Green | 90 | 10 | 100 | 90 | 10 | 40 | 90 | 70 | 60 | 50 | 10 | 10 | 0 | 0 |
| Galium | 100 | 10 | 100 | 100 | 30 | 90 | 100 | 80 | 30 | 20 | 40 | 10 | 0 | 50 |
| Kochia | 100 | 10 | 100 | 100 | 10 | 60 | 100 | 90 | 80 | 60 | 50 | 10 | 0 | 80 |
| Pigweed | 100 | 50 | 100 | 100 | 90 | 100 | 100 | 100 | 100 | 90 | 50 | 30 | 10 | 50 |
| Ragweed | 10 | 30 | 60 | 80 | 0 | 0 | 0 | 20 | 10 | 10 | 10 | 20 | 0 | 70 |
| Ryegrass, Italian | 50 | 10 | 100 | 90 | 10 | 30 | 60 | 50 | 30 | 30 | 40 | 0 | 0 | 20 |
| Wheat | 30 | 0 | 90 | 80 | 0 | 10 | 30 | 50 | 20 | 10 | 10 | 0 | 0 | 30 |

| 125 g ai/ha Postemergence | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| Barnyardgrass | 30 | 80 | 70 | 0 | 100 | 100 | 20 | 40 | 20 | 70 | 10 | 100 | 30 | 10 | 30 |
| Blackgrass | 30 | 90 | 50 | 0 | 100 | 100 | 30 | 50 | 30 | 80 | 60 | 0 | 40 | 60 | 30 |
| Corn | 20 | 40 | 20 | 10 | 70 | 50 | 20 | 30 | 20 | 20 | 20 | 20 | 30 | 20 | 30 |
| Foxtail, Giant | — | 90 | 40 | 0 | 90 | 90 | 20 | 40 | 10 | 50 | 30 | 20 | 30 | 20 | 10 |
| Foxtail, Green | 20 | — | — | — | — | — | — | — | — | — | — | — | — | — | — |
| Galium | 80 | 100 | 90 | 10 | 100 | 100 | 30 | 80 | 70 | 80 | 40 | 50 | 80 | 60 | 50 |
| Kochia | 80 | 100 | 70 | 10 | 100 | 100 | 60 | 80 | 70 | 50 | 60 | 60 | 10 | 70 | 60 |
| Pigweed | 70 | 100 | 70 | 20 | 100 | 100 | 50 | 80 | 70 | 70 | 50 | 60 | 70 | 70 | 70 |
| Ragweed | 30 | 50 | 10 | 0 | 70 | 70 | 10 | 20 | 10 | 20 | 30 | 10 | 10 | 20 | 30 |

TABLE A-continued

| Compounds | | | | | | | | | | | | | | |
|---|---|---|---|---|---|---|---|---|---|---|---|---|---|---|
| Ryegrass, Italian | 20 | 80 | 10 | 0 | 100 | 80 | 0 | 20 | 0 | 20 | 0 | 0 | 40 | 0 | 30 |
| Wheat | 10 | 50 | 10 | 0 | 100 | 90 | 0 | 0 | 30 | 0 | 10 | 0 | 10 | 0 | 10 |

| 125 g ai/ha Postemergence | 30 | 31 | 32 | 33 | 34 | 35 | 36 |
|---|---|---|---|---|---|---|---|
| Barnyardgrass | 30 | 0 | 20 | 20 | 10 | 0 | 10 |
| Blackgrass | 60 | 0 | 30 | 20 | 10 | 10 | 0 |
| Corn | 30 | 10 | 20 | 0 | 20 | 0 | 0 |
| Foxtail, Giant | 40 | 0 | 20 | 20 | 20 | — | 20 |
| Foxtail, Green | — | — | — | — | — | 10 | — |
| Galium | 80 | 30 | 20 | 70 | 50 | 30 | 10 |
| Kochia | 30 | 40 | 10 | 40 | 10 | 50 | 50 |
| Pigweed | 90 | 50 | 40 | 30 | 40 | 50 | 10 |
| Ragweed | 10 | 0 | 0 | 10 | 0 | 10 | 0 |
| Ryegrass, Italian | 30 | 0 | 0 | 0 | 0 | 0 | 0 |
| Wheat | 20 | 0 | 10 | 0 | 10 | 0 | 0 |

| 31 g ai/ha Postemergence | 2 | 3 | 4 | 5 | 6 | 7 | 8 | 9 | 10 | 11 | 12 | 13 | 16 | 17 |
|---|---|---|---|---|---|---|---|---|---|---|---|---|---|---|
| Barnyardgrass | 0 | 30 | 30 | 0 | 10 | 20 | 10 | 20 | 10 | 20 | 0 | 0 | 30 | 10 |
| Blackgrass | 0 | 80 | 40 | 10 | 10 | 10 | 30 | 20 | 10 | 0 | 0 | 0 | 80 | 30 |
| Corn | 0 | 50 | 30 | 0 | 0 | 20 | 10 | 20 | 10 | 0 | 0 | 0 | 0 | 20 |
| Foxtail, Giant | — | — | — | — | — | — | — | — | — | — | — | — | 30 | 20 |
| Foxtail, Green | 0 | 40 | 30 | 10 | 10 | 30 | 20 | 20 | 10 | 0 | 0 | 0 | — | — |
| Galium | 0 | 100 | 100 | 0 | 60 | 50 | 30 | 20 | 10 | 10 | 0 | 0 | 90 | 40 |
| Kochia | 0 | 90 | 90 | 0 | 10 | 90 | 80 | 50 | 10 | 20 | 0 | 0 | 80 | 30 |
| Pigweed | 10 | 100 | 90 | 10 | 90 | 80 | 100 | 80 | 50 | 40 | 0 | 0 | 80 | 50 |
| Ragweed | 0 | 10 | 0 | 0 | 0 | 0 | 10 | 0 | 0 | 0 | 0 | 0 | 10 | 10 |
| Ryegrass, Italian | 0 | 40 | 20 | 0 | 0 | 20 | 10 | 10 | 0 | 30 | 0 | 0 | 20 | 0 |
| Wheat | 0 | 60 | 20 | 0 | 0 | 10 | 0 | 10 | 0 | 0 | 0 | 0 | 50 | 0 |

| 31 g ai/ha Postemergence | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| Barnyardgrass | 0 | 50 | 40 | 0 | 20 | 20 | 20 | 0 | 100 | 20 | 0 | 0 | 20 | 20 | 10 |
| Blackgrass | 0 | 100 | 80 | 10 | 0 | 20 | 30 | 20 | 0 | 20 | 10 | 30 | 20 | 0 | 10 |
| Corn | 0 | 40 | 30 | 0 | 20 | 10 | 10 | 20 | 10 | 20 | 10 | 10 | 30 | 0 | 10 |
| Foxtail, Giant | 0 | 60 | 50 | 0 | 0 | 0 | 0 | 0 | 0 | 10 | 10 | 0 | 0 | 0 | 0 |
| Foxtail, Green | — | — | — | — | — | — | — | — | — | — | — | — | — | — | — |
| Galium | 0 | 90 | 90 | 10 | 50 | 40 | 20 | 30 | 20 | 40 | 20 | 20 | 30 | 0 | 10 |
| Kochia | 0 | 80 | 90 | 20 | 40 | 20 | 20 | 30 | 20 | 10 | 20 | 20 | 10 | 10 | 0 |
| Pigweed | 10 | 100 | 100 | 20 | 30 | 60 | 20 | 30 | 30 | 50 | 30 | 30 | 70 | 40 | 20 |
| Ragweed | 0 | 30 | 30 | 0 | 0 | 0 | 0 | 0 | 0 | 0 | 10 | 10 | 10 | 0 | 0 |
| Ryegrass, Italian | 0 | 80 | 30 | 0 | 30 | 0 | 0 | 0 | 0 | 10 | 0 | 0 | 30 | 0 | 0 |
| Wheat | 0 | 20 | 20 | 0 | 0 | 20 | 0 | 0 | 0 | 0 | 0 | 0 | 0 | 0 | 0 |

| 31 g ai/ha Postemergence | 33 | 34 | 35 | 36 |
|---|---|---|---|---|
| Barnyardgrass | 10 | 0 | 0 | 0 |
| Blackgrass | 0 | 0 | 10 | 0 |
| Corn | 0 | 10 | 0 | 0 |
| Foxtail, Giant | 20 | 0 | — | 0 |
| Foxtail, Green | — | — | 10 | — |
| Galium | 50 | 20 | 10 | 10 |
| Kochia | 30 | 20 | 20 | 30 |
| Pigweed | 20 | 10 | 30 | 10 |
| Ragweed | 0 | 0 | 0 | 0 |
| Ryegrass, Italian | 0 | 0 | 0 | 0 |
| Wheat | 0 | 0 | 0 | 0 |

| 500 g ai/ha Preemergence | 1 | 14 | 15 |
|---|---|---|---|
| Barnyardgrass | 100 | 90 | 70 |
| Foxtail, Green | 100 | 100 | 100 |
| Kochia | 100 | 100 | 80 |
| Pigweed | 100 | 100 | 100 |
| Ragweed | 90 | 70 | 20 |
| Ryegrass, Italian | 100 | 60 | 30 |

| 125 g ai/ha Preemergence | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Barnyardgrass | 100 | 0 | 100 | 100 | 0 | 90 | 90 | 100 | 90 | 70 | 50 | 0 | 0 | 20 |
| Foxtail, Giant | — | — | — | — | — | — | — | — | — | — | — | — | — | — |

TABLE A-continued

| Compounds | | | | | | | | | | | | | | | |
|---|---|---|---|---|---|---|---|---|---|---|---|---|---|---|---|
| Foxtail, Green | 100 | 30 | 100 | 100 | 0 | 100 | 100 | 100 | 100 | 90 | 70 | 0 | 0 | 40 | |
| Kochia | 100 | 0 | 100 | 100 | 0 | 80 | 100 | 100 | 50 | 30 | 20 | 0 | 0 | 50 | |
| Pigweed | 100 | 20 | 100 | 100 | 90 | 100 | 100 | 100 | 100 | 100 | 100 | 0 | 0 | 100 | |
| Ragweed | 80 | 0 | 0 | 70 | 0 | 0 | 0 | 10 | 10 | 0 | 0 | 0 | 0 | 40 | |
| Ryegrass, Italian | 80 | 0 | 100 | 100 | 0 | 10 | 50 | 70 | 50 | 30 | 20 | 0 | 0 | 10 | |

| 125 g ai/ha Preemergence | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| Barnyardgrass | 30 | 100 | 50 | 0 | 100 | 100 | 20 | 60 | 30 | 50 | 30 | 30 | 80 | 60 | 10 |
| Foxtail, Giant | — | 100 | 70 | 0 | 100 | 100 | 0 | 70 | 40 | 20 | 90 | 60 | 100 | 100 | 20 |
| Foxtail, Green | 50 | — | — | — | — | — | — | — | — | — | — | — | — | — | — |
| Kochia | 20 | 100 | 60 | 0 | 100 | 100 | 0 | 80 | 60 | 60 | 70 | 20 | 0 | 50 | 10 |
| Pigweed | 70 | 100 | 100 | 0 | 100 | 100 | 0 | 30 | 100 | 30 | 100 | 100 | 50 | 100 | 80 |
| Ragweed | 0 | — | 0 | 0 | 60 | 100 | 0 | 0 | 0 | 0 | 0 | 0 | 0 | 0 | 10 |
| Ryegrass, Italian | 0 | 70 | 10 | 0 | 90 | 60 | 0 | 20 | 0 | 10 | 0 | 10 | 20 | 10 | 0 |

| 125 g ai/ha Preemergence | 30 | 31 | 32 | 33 | 34 | 35 | 36 |
|---|---|---|---|---|---|---|---|
| Barnyardgrass | 40 | 0 | 40 | 50 | 0 | 10 | 0 |
| Foxtail, Giant | 80 | 0 | 50 | 100 | 10 | — | 60 |
| Foxtail, Green | — | — | — | — | — | 10 | — |
| Kochia | 0 | 0 | 0 | 0 | 0 | 0 | 0 |
| Pigweed | 60 | 0 | 60 | 10 | 0 | 10 | 0 |
| Ragweed | 0 | 0 | 0 | — | 0 | 0 | — |
| Ryegrass, Italian | 10 | 0 | 0 | 50 | 0 | 0 | 0 |

| 31 g ai/ha Preemergence | 2 | 3 | 4 | 5 | 6 | 7 | 8 | 9 | 10 | 11 | 12 | 13 | 16 | 17 |
|---|---|---|---|---|---|---|---|---|---|---|---|---|---|---|
| Barnyardgrass | 0 | 90 | 70 | 0 | 0 | 20 | 80 | 10 | 10 | 0 | 0 | 0 | 60 | 10 |
| Foxtail, Giant | — | — | — | — | — | — | — | — | — | — | — | — | 80 | 10 |
| Foxtail, Green | 0 | 100 | 100 | 0 | 20 | 80 | 80 | 70 | 60 | 10 | 0 | 0 | — | — |
| Kochia | 0 | 80 | 90 | 0 | 0 | 0 | 20 | 10 | 0 | 0 | 0 | 0 | 10 | 0 |
| Pigweed | 0 | 100 | 100 | 0 | 0 | 20 | 100 | 10 | 100 | 10 | 0 | 0 | 100 | 60 |
| Ragweed | 0 | 0 | 20 | 0 | 0 | 0 | 0 | 0 | 0 | 0 | 0 | 0 | — | 0 |
| Ryegrass, Italian | 0 | 70 | 20 | 0 | 0 | 0 | 10 | 10 | 10 | 0 | 0 | 0 | 10 | 0 |

| 31 g ai/ha Preemergence | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| Barnyardgrass | 0 | 80 | 70 | 0 | 0 | 0 | 0 | 0 | 0 | 10 | 0 | 0 | 0 | 0 | 0 |
| Foxtail, Giant | 0 | 100 | 100 | 0 | 10 | 0 | 0 | 20 | 0 | 50 | 10 | 0 | 10 | 0 | 0 |
| Foxtail, Green | — | — | — | — | — | — | — | — | — | — | — | — | — | — | — |
| Kochia | 0 | 90 | 100 | 0 | 20 | 0 | 20 | 0 | 0 | 0 | 0 | 0 | 0 | 0 | 0 |
| Pigweed | 0 | 100 | 100 | 0 | 0 | 20 | 0 | 10 | 20 | 30 | 10 | 0 | 10 | 0 | 0 |
| Ragweed | 0 | 0 | 30 | 0 | 0 | 0 | — | 0 | 0 | 0 | 0 | 0 | 0 | 0 | 0 |
| Ryegrass, Italian | 0 | 10 | 10 | 0 | 0 | 0 | 0 | 0 | 0 | 0 | 0 | 0 | 0 | 0 | 0 |

| 31 g ai/ha Preemergence | 33 | 34 | 35 | 36 |
|---|---|---|---|---|
| Barnyardgrass | 0 | 0 | 0 | 0 |
| Foxtail, Giant | 10 | 0 | 0 | 0 |
| Foxtail, Green | — | — | 0 | — |
| Kochia | 0 | 0 | 0 | 0 |
| Pigweed | 0 | 0 | 0 | 0 |
| Ragweed | — | 0 | 0 | — |
| Ryegrass, Italian | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| | Compounds | | | | | | | | | | | | | |
|---|---|---|---|---|---|---|---|---|---|---|---|---|---|---|
| 250 g ai/ha Flood | 1 | 2 | 3 | 4 | 5 | 6 | 7 | 8 | 9 | 10 | 12 | 13 | 14 | 15 |
| Barnyardgrass | 0 | 0 | 60 | 35 | 0 | 40 | 40 | 35 | 70 | 45 | 0 | 0 | 0 | 0 |
| Ducksalad | 20 | 0 | 90 | 100 | 60 | 100 | 100 | 100 | 100 | 95 | 0 | 0 | 40 | 0 |
| Rice | 0 | 0 | 60 | 45 | 40 | 20 | 40 | 20 | 50 | 25 | 0 | 0 | 0 | 0 |
| Sedge, Umbrella | 70 | 0 | 100 | 100 | 70 | 100 | 100 | 100 | 100 | 95 | 0 | 0 | 50 | 0 |
| 250 g ai/ha Flood | 16 | 17 | 18 | 19 | 20 | 21 | 22 | 23 | 24 | 25 | 27 | 28 | 29 | 30 |
| Barnyardgrass | 75 | 0 | 0 | 60 | 90 | 0 | 35 | 0 | 25 | 0 | 0 | 0 | 0 | 20 |
| Ducksalad | 100 | 0 | 0 | 100 | 100 | 70 | 80 | 0 | 90 | 0 | 95 | 0 | 0 | 85 |
| Rice | 15 | 0 | 0 | 50 | 30 | 0 | 0 | 0 | 0 | 0 | 0 | 0 | 0 | 0 |
| Sedge, Umbrella | 90 | 0 | 0 | 100 | 100 | 0 | 90 | 0 | 80 | 0 | 95 | 0 | 0 | 95 |
| 250 g ai/ha Flood | 31 | | 32 | | 33 | | 34 | | 35 | | 36 | | | |
| Barnyardgrass | 0 | | 0 | | 0 | | 0 | | 0 | | 0 | | | |
| Ducksalad | 0 | | 95 | | 70 | | 0 | | 0 | | 50 | | | |
| Rice | 0 | | 0 | | 0 | | 0 | | 0 | | 0 | | | |
| Sedge, Umbrella | 0 | | 98 | | 75 | | 0 | | 0 | | 20 | | | |

What is claimed is:

1. A compound selected from Formula 1, N-oxides and salts thereof,

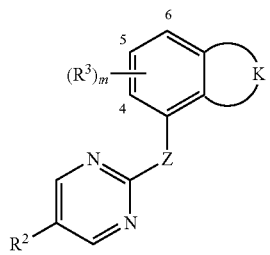

1

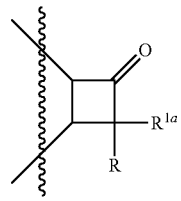

K-1

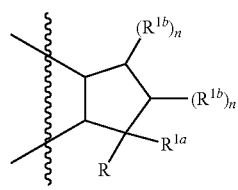

K-2

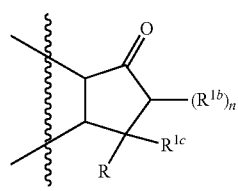

K-3 wherein
  K together with the two contiguous linking carbon atoms forms a 4-, 5- or 6-membered ring selected from the group consisting of K-1, K-2, K-3, K-4, K-5, K-6, K-7, K-8, K-9, K-10, K-11, K-12, K-13, K-14, K-15, K-16 and K-17:

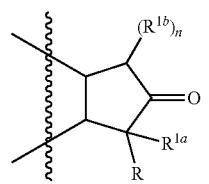
K-4

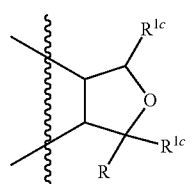
K-5

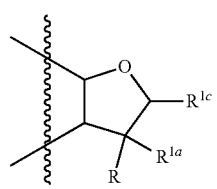
K-6

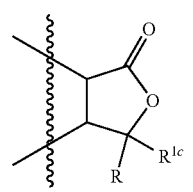
K-7

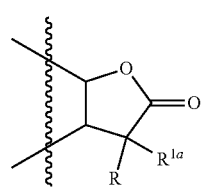
K-8

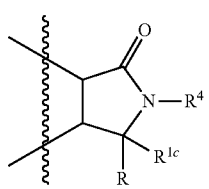
K-9

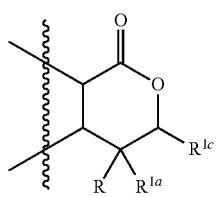
K-10

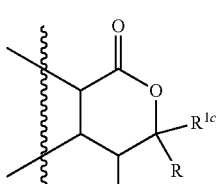
K-11

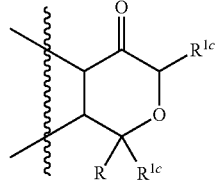
K-12

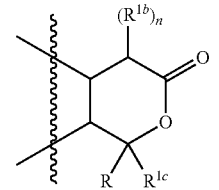
K-13

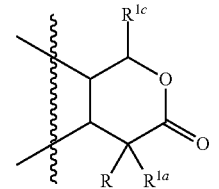
K-14

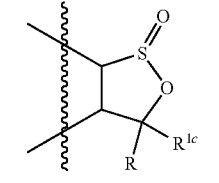
K-15

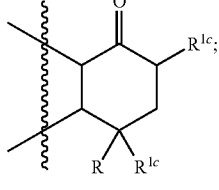
K-16

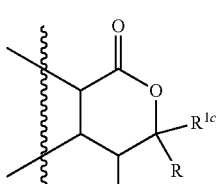
K-17

R is $C_2$-$C_5$ haloalkyl;

each $R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano or $S(O)_p R^8$;

each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_p R^8$;

each $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_p R^8$;

$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_q R^9$;

each $R^3$ is independently halogen, cyano, nitro, CHO, C(=O)NH$_2$, C(=S)NH$_2$, SO$_2$NH$_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_4$ alkoxy, $C_3$-$C_4$ alkenyloxy, $C_3$-$C_4$ alkynyloxy, $C_1$-$C_4$ haloalkoxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy or $C_2$-$C_4$ alkylthioalkyl;

m is 0, 1, 2 or 3;
each n is independently selected from 0 and 1;
p is 0, 1 or 2;
q is 0, 1 or 2;
r is 0, 1 or 2;
Z is O or S;
$R^4$ is nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_rR^9$;
$R^5$ is $C_1$-$C_6$ alkyl or $C_1$-$C_6$ haloalkyl;
$R^6$ is H, $C_1$-$C_6$ alkyl, $C_1$-$C_6$ haloalkyl, $C_2$-$C_6$ alkoxyalkyl, $C_2$-$C_6$ haloalkoxyalkyl or $C_2$-$C_6$ cyanoalkyl;
each $R^{7a}$ and $R^{7b}$ is independently H, $C_1$-$C_6$ alkyl or $C_1$-$C_6$ haloalkyl;
$R^8$ is $C_1$-$C_6$ alkyl or $C_1$-$C_6$ haloalkyl; and
$R^9$ is independently $C_1$-$C_6$ alkyl, $C_1$-$C_6$ haloalkyl, $C_1$-$C_6$ alkylamino or $C_2$-$C_{10}$ dialkylamino.

2. The compound of claim 1 wherein
K is K-2, K-3, K-4, K-5, K-6, K-7, K-10, K-11, K-12, K-13, K-14 or K-15;
Z is O;
$R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy or cyano;
each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano;
each $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy and cyano;
$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl or $C_3$-$C_6$ cycloalkyl;
$R^3$ is halogen, cyano, $C_1$-$C_4$ alkyl or $C_1$-$C_4$ haloalkyl; and
m is 0 or 1.

3. The compound of claim 2 wherein
K is K-2, K-3, K-4, K-5, K-6, K-7, K-8 or K-10;
$R^{1a}$ is hydrogen, halogen, $C_1$-$C_2$ alkyl, $C_1$-$C_2$ haloalkyl, hydroxy or cyano;
each $R^{1b}$ is independently selected from halogen, $C_1$-$C_2$ alkyl, $C_1$-$C_2$ haloalkyl, hydroxy and cyano;
each $R^{1c}$ is independently selected from hydrogen, F, $C_1$-$C_2$ alkyl, $C_1$-$C_2$ haloalkyl, hydroxy and cyano;
$R^2$ is halogen, cyano, $C_1$-$C_2$ alkyl or $C_1$-$C_2$ haloalkyl; and
$R^3$ is at the 5- or 6-position and selected from halogen or cyano.

4. The compound of claim 3 wherein
K is K-2, K-3, K-4, K-5, K-6, K-7 or K-8.

5. The compound of claim 4 wherein K is K-3, K-5 or K-7;
R is $C_3$-$C_4$ haloalkyl;
$R^{1a}$ is H, F, OH, $CF_3$ or CN;
$R^{1b}$ is independently selected from F, OH, $CF_3$ and CN;
$R^{1c}$ is independently selected from H, F, OH, $CF_3$ and CN;

$R^2$ is halogen; and
$R^3$ is F or cyano.

6. The compound of claim 5 wherein
R is —$CH_2CH_2CF_3$ or —$CH_2CH_2CH_2CF_3$;
$R^{1a}$ is hydrogen;
each $R^{1c}$ is hydrogen;
$R^2$ is Cl; and
each n is 0.

7. The compound of claim 1 selected from the group consisting of
4-[(5-Chloro-2-pyrimidinyl)oxy]-3-(4,4,4-trifluorobutyl)-1(3H)-isobenzofuranone;
(3S)-4-[(5-Chloro-2-pyrimidinyl)oxy]-3-(4,4,4-trifluorobutyl)-1-(3H)-isobenzofuranone;
(3R)-4-[(5-Chloro-2-pyrimidinyl)oxy]-3-(4,4,4-trifluorobutyl)-1-(3H)-isobenzofuranone;
4-[(5-Chloro-2-pyrimidinyl)oxy]-3-(3,3,3-trifluoropropyl)-1(3H)-isobenzofuranone;
8-[(5-Chloro-2-pyrimidinyl)oxy]-1-(4,4,4-trifluorobutyl)-1H-2-benzopyran-4(3H)-one;
4-[(5-Chloro-2-pyrimidinyl)oxy]-2,3-dihydro-3-(4,4,4-trifluorobutyl)-1H-inden-1-one;
5-Chloro-2-[[1,3-dihydro-3-(4,4,4-trifluorobutyl)-4-isobenzofuranyl]oxy]pyrimidine;
5-Chloro-2-[[1,3-dihydro-3-(3,3,3-trifluoropropyl)-4-isobenzofuranyl]oxy]pyrimidine;
5-Chloro-2-[[2,3-dihydro-3-(4,4,4-trifluorobutyl)-1H-inden-4-yl]oxy]pyrimidine;
4-[(5-Chloro-2-pyrimidinyl)oxy]-2,3-dihydro-3-(4,4,4-trifluorobutyl)-1H-inden-1-ol;
4-[(5-Chloro-2-pyrimidinyl)oxy]-2,3-dihydro-3-(3,3,3-trifluoropropyl)-1H-inden-1-one;
4-[(5-Chloro-2-pyrimidinyl)oxy]-2,3-dihydro-2-methyl-3-(4,4,4-trifluorobutyl)-1H-isoindol-1-one;
4-[(5-Chloro-2-pyrimidinyl)oxy]-2,3-dihydro-3-(4,4,4-trifluorobutyl)-1H-isoindol-1-one;
7-[(5-Chloro-2-pyrimidinyl)oxy]-2,3-dihydro-1-(3,3,3-trifluoropropyl)-1H-inden-1-ol;
5-Chloro-2-[[1-oxido-3-(4,4,4-trifluorobutyl)-3H-2,1-benzoxathiol-4-yl]oxy]pyrimidine;
5-[(5-Chloro-2-pyrimidinyl)oxy]-3,4-dihydro-4-(4,4,4,-trifluorobutyl)-1H-2benzopyran-1-one;
8-[(5-Chloro-2-pyrimidinyl)oxy]-1,4-dihydro-1-(4,4,4-trifluorobutyl)-3H-2-benzopyran-3-one;
(3S)-4-[(5-Chloro-2-pyrimidinyl)oxy]-3-(3,3,3-trifluoropropyl)-1(3H)-isobenzofuranone;
(3R)-4-[(5-Chloro-2-pyrimidinyl)oxy]-3-(3,3,3-trifluoropropyl)-1(3H)-isobenzofuranone;
5-Chloro-2-[[(3R)-1,3-dihydro-3-(3,3,3-trifluoropropyl)-4-isobenzofuranyl]oxy]-pyrimidine;
5-Chloro-2-[[(3S)-1,3-dihydro-3-(3,3,3-trifluoropropyl)-4-isobenzofuranyl]oxy]-pyrimidine;
2-[(5-Chloro-2-pyrimidinyl)oxy]-8-(4,4,4-trifluorobutyl)bicyclo[4.2.0]octa-1,3,5-trien-7-one;
5-[(5-Chloro-2-pyrimidinyl)oxy]-3,4-dihydro-3-(3,3,3-trifluoropropyl)-1H-2-benzopyran-1-one;
2-[(5-Chloro-2-pyrimidinyl)oxy]-8-(3,3,3-trifluoropropyl)bicyclo[4.2.0]octa-1,3,5-trien-7-one;
5-[(5-Chloro-2-pyrimidinyl)oxy]-3,4-dihydro-4-(3,3,3-trifluoropropyl)-1H-2-benzopyran-1-one;
5-[(5-Chloro-2-pyrimidinyl)oxy]-1,4-dihydro-4-(4,4,4-trifluorobutyl)-3H-2-benzopyran-3-one;
5-Chloro-2-[[3,4-dihydro-1-(4,4,4-trifluorobutyl)-1H-2-benzopyran-8-yl]oxy]pyrimidine;
8-[(5-Chloro-2-pyrimidinyl)oxy]-1,4-dihydro-1-(3,3,3-trifluoropropyl)-3H-2-benzopyran-3-one;

5-[(5-Chloro-2-pyrimidinyl)oxy]-1,4-dihydro-4-(3,3,3-trifluoropropyl)-3H-2-benzopyran-3-one;

5-[(5-Chloro-2-pyrimidinyl)oxy]-3,4-dihydro-4-(4,4,4-trifluorobutyl)-1(2H)-naphthalenone;

5-[(5-Chloro-2-pyrimidinyl)oxy]-3,4-dihydro-3-(5,5,5-trifluoropentyl)-1H-2-benzopyran-1-one;

5-Chloro-2-[[3,4-dihydro-1-(3,3,3-trifluoropropyl)-1H-2-benzopyran-8-yl]oxy]pyrimidine;

5-Chloro-2-[[2,3-dihydro-3-(4,4,4-trifluorobutyl)-4-benzofuranyl]oxy]pyrimidine;

5-[(5-Chloro-2-pyrimidinyl)oxy]-1,4-dihydro-4-(5,5,5-trifluoropentyl)-3H-2-benzopyran-3-one;

8-[(5-Chloro-2-pyrimidinyl)oxy]-1,4-dihydro-1-propyl-3H-2-benzopyran-3-one; and

5-Chloro-2-[[2,3-dihydro-3-(3,3,3-trifluoropropyl)-4-benzofuranyl]oxy]pyrimidine.

8. A herbicidal composition comprising a compound of claim 1 and at least one component selected from the group consisting of surfactants, solid diluents and liquid diluents.

9. A herbicidal composition comprising a compound of claim 1, at least one additional active ingredient selected from the group consisting of other herbicides and herbicide safeners, and at least one component selected from the group consisting of surfactants, solid diluents and liquid diluents.

10. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

11. A herbicidal mixture comprising (a) a compound of claim 1, and (b) at least one additional active ingredient selected from (b1) photosystem II inhibitors, (b2) acetohydroxy acid synthase (AHAS) inhibitors, (b4) auxin mimics, (b5) 5-enol-pyruvylshikimate-3-phosphate (EPSP) synthase inhibitors, (b7) protoporphyrinogen oxidase (PPO) inhibitors, (b9) very long chain fatty acid (VLCFA) elongase inhibitors and (b12) 4-hydroxyphenyl-pyruvate dioxygenase (HPPD) inhibitors.

12. A herbicidal mixture comprising (a) a compound of claim 1, and (b) at least one additional active ingredient selected from the group consisting of 2,4-D, acetochlor, alachlor, atrazine, bromoxynil, bentazon, bicyclopyrone, carfentrazone-ethyl, cloransulam-methyl, dicamba, dimethenamid-p, florasulam, flufenacet, flumioxazin, flupyrsulfuron-methyl, fluroxypyr-meptyl, glyphosate, halauxifen-methyl, isoxaflutole, MCPA, mesotrione, metolachlor, metsulfuron-methyl, nicosulfuron, pyrasulfotole, pyroxasulfone, pyroxsulam, rimsulfuron, saflufenacil, tembotrione, thifensulfuron-methyl, topramazone and tribenuron.

13. A method for controlling the growth of undesired vegetation comprising contacting the vegetation or its environment with a herbicidally effective amount of a compound of claim 1.

14. A method for controlling the growth of undesired vegetation in genetically modified plants that exhibit traits of glyphosate tolerance, glufosinate tolerance, ALS herbicide tolerance, dicamba tolerance, imidazolinone herbicide tolerance, 2,4-D tolerance, HPPD tolerance and mesotrione tolerance, comprising contacting the vegetation or its environment with a herbicidally effective amount of a compound selected from Formula 1, N-oxides and salts thereof,

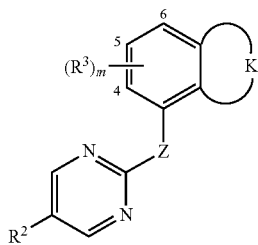

wherein

K together with the two contiguous linking carbon atoms forms a 4-, 5- or 6-membered ring selected from the group consisting of K-1, K-2, K-3, K-4, K-5, K-6, K-7, K-8, K-9, K-10, K-11, K-12, K-13, K-14, K-15, K-16 and K-17:

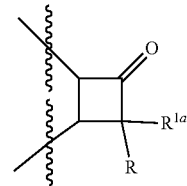

K-1

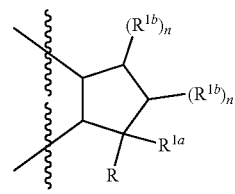

K-2

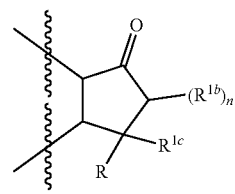

K-3

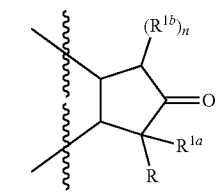

K-4

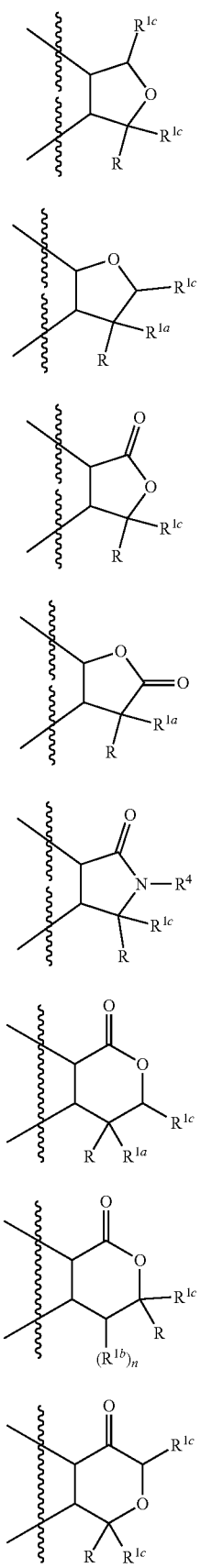
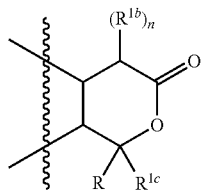
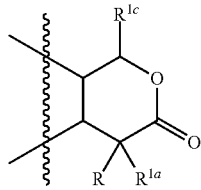
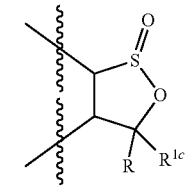
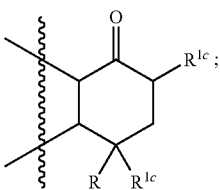
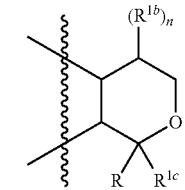

R is $C_1$-$C_6$ alkyl, $C_2$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, alkylsulfonyl, haloalkylsulfonyl, $C_3$-$C_8$ cycloalkylsulfonyl, $C_2$-$C_6$ alkylthioalkyl, $C_2$-$C_6$ haloalkylthioalkyl, benzyl, —N($R^5$)(O$R^6$), —ON($R^{7a}$)($R^{7b}$) or —N($R^5$)N($R^{7a}$)($R^{7b}$);

each $R^{1a}$ is hydrogen, halogen, $C_1$-$C_4$ alkyl, $C_1$-$C_4$ haloalkyl, $C_2$-$C_6$ alkenyl, $C_2$-$C_6$ alkynyl, hydroxy, alkoxy, $C_1$-$C_4$ haloalkoxy, cyano or S(O) $R^8$;

each $R^{1b}$ is independently selected from halogen, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_p R^8$;

each $R^{1c}$ is independently selected from hydrogen, F, $C_1$-$C_4$ alkyl, $C_1$-$C_4$ haloalkyl, $C_2$-$C_6$ alkenyl, $C_2$-$C_6$ alkynyl, hydroxy, $C_1$-$C_4$ alkoxy, $C_1$-$C_4$ haloalkoxy, cyano and $S(O)_p R^8$;

$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_q R^1$;

each $R^3$ is independently halogen, cyano, nitro, CHO, C(=O)NH$_2$, C(=S)NH$_2$, SO$_2$NH$_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_4$ alkoxy, $C_3$-$C_4$ alkenyloxy, $C_3$-$C_4$ alkynyloxy, haloalkoxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy or $C_2$-$C_4$ alkylthioalkyl;

m is 0, 1, 2 or 3;

each n is independently selected from 0 and 1;

p is 0, 1 or 2;

q is 0, 1 or 2;

r is 0, 1 or 2;

Z is O or S;

$R^4$ is nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or $S(O)_r R^9$;

$R^5$ is $C_1$-$C_6$ alkyl or $C_1$-$C_6$ haloalkyl;

$R^6$ is H, alkyl, haloalkyl, $C_2$ alkoxyalkyl, $C_2$ haloalkoxyalkyl or $C_2$-$C_6$ cyanoalkyl;

each $R^{7a}$ and $R^{7b}$ is independently H, $C_1$-$C_6$ alkyl or $C_1$-$C_6$ haloalkyl;

$R^8$ is $C_1$-$C_6$ alkyl or $C_1$-$C_6$ haloalkyl; and $R^9$ is independently $C_1$-$C_6$ alkyl, $C_1$-$C_6$ haloalkyl, $C_1$-$C_6$ alkylamino or $C_2$-$C_{10}$ dialkylamino.

* * * * *